(12) United States Patent
Ohta et al.

(10) Patent No.: US 7,825,127 B2
(45) Date of Patent: Nov. 2, 2010

(54) METHOD FOR TREATING CANCER

(75) Inventors: Yoshikazu Ohta, Tsukuba (JP); Shinji Takagi, Tsukuba (JP)

(73) Assignee: Takeda Pharmaceutical Company, Limited, Osaka (JP)

( * ) Notice: Subject to any disclaimer, the term of this patent is extended or adjusted under 35 U.S.C. 154(b) by 212 days.

(21) Appl. No.: 12/005,883

(22) Filed: Dec. 27, 2007

(65) Prior Publication Data

US 2008/0214584 A1   Sep. 4, 2008

Related U.S. Application Data

(60) Provisional application No. 60/877,460, filed on Dec. 28, 2006.

(51) Int. Cl.
*A61K 31/519* (2006.01)
(52) U.S. Cl. .................................................. 514/265.1
(58) Field of Classification Search ................ 514/265.1
See application file for complete search history.

(56) References Cited

U.S. PATENT DOCUMENTS

| | | | |
|---|---|---|---|
| 7,507,740 B2 * | 3/2009 | Ishikawa et al. | ......... 514/265.1 |
| 2004/0138160 A1 | 7/2004 | Naito et al. | |
| 2006/0121044 A1 | 6/2006 | Amler et al. | |
| 2007/0244132 A1 | 10/2007 | Ishikawa et al. | |

FOREIGN PATENT DOCUMENTS

WO    WO 2007/064045    6/2007

OTHER PUBLICATIONS

Sausville et al. Cancer Research, 2006, vol. 66, pp. 3351-3354.*
Johnson et al. British J. of Cancer, 2001, 84(10):1424-1431.*

* cited by examiner

*Primary Examiner*—James D Anderson
(74) *Attorney, Agent, or Firm*—Hamre, Schumann, Mueller & Larson, P.C.

(57) ABSTRACT

The present invention provides a method for treating cancer, which includes selecting a patient coexpressing HER2 and HER3, and administering an effective amount of a HER2 inhibitor to the patient.

2 Claims, 2 Drawing Sheets

METHOD FOR TREATING CANCER

TECHNICAL FIELD

The present invention relates to a method for treating cancer.

BACKGROUND ART

The NEU oncogene obtained from rat neuroblastoma induced by a chemical carcinogenic substance was found to encode a protein belonging to the EGF receptor family, and the relationship with which was suggested. Thereafter, an NEU human homologue was isolated and named as ERBB2 or HER2 based on the similarity to an EGF receptor (ERBB). Expression of HER2 in breast cancer, prostate cancer, lung cancer, gastric cancer and the like has been reported and HER2 is considered to be involved in the growth of these cancers.

For example, it has been reported that about 25% of primary prostate cancer is HER2 expression positive, and the percentage increases along with the progression of the cancer (Journal of the National Cancer Institute, Vol. 92, No. 23, pp. 1918-1925 (2000)).

In addition, it is known that the prognosis of patients with HER2 expression is poor in comparison with patients without HER2 expression.

HER2 hardly expresses in normal tissues. Therefore, an HER2 selective therapeutic drug would be cancer selective, with the reduced toxicity or extremely few side effects. This means that an extreme safe and highly versatile treatment method can be provided, which is strikingly different from conventional cancer chemotherapeutic agents. Examples of the HER2 selective therapeutic drug include a tyrosine kinase (phosphorylation enzyme) inhibitor having high selectivity to HER2 and the like.

As a compound inhibiting a receptor-type tyrosine kinase including HER2/EGFR kinase, fused heterocyclic compounds (see, for example, WO97/13771, WO98/02437 and WO00/44728), quinazoline derivatives (see, for example, WO02/02552, WO01/98277, WO03/049740 and WO03/050108), thienopyrimidine derivatives (see, for example, WO03/053446), aromatic azole derivatives (see, for example, WO98/03648, WO01/77107 and WO03/031442), and the like are known. However, there has not been any HER2 kinase inhibitory substance placed on the market heretofore as a therapeutic drug for cancer.

In addition, to use such pharmaceutical agents more effectively for the treatment, it is preferable that the efficacy prediction in patients be available.

DISCLOSURE OF THE INVENTION

The present inventors have conducted intensive studies in an attempt to solve the above-described problem, and unexpectedly found that cancer can be efficiently treated by selecting patients coexpressing HER2 and HER3 and administrating an effective amount of a HER2 inhibitor to the patients, which resulted in the completion of the present invention. Accordingly, the present invention relates to

[1] a method for treating cancer, which comprises selecting a patient coexpressing HER2 and HER3 and administering an effective amount of a HER2 inhibitor to the patient;

[2] the method of the above-mentioned [1], wherein the HER2 inhibitor is lapatinib;

[3] the method of the above-mentioned [1], wherein the HER2 inhibitor is a compound represented by the formula:

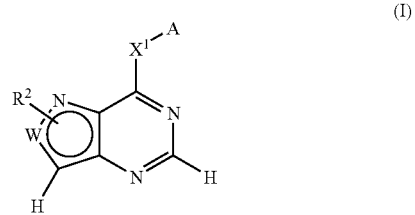

wherein W is C(R$^1$) or N,

A is an optionally substituted aryl group or an optionally substituted heteroaryl group, X$^1$ is —NR$^3$—Y$^1$—, —O—, —S—, —SO—, —SO$_2$— or —CHR$^3$— wherein R$^3$ is a hydrogen atom or an optionally substituted aliphatic hydrocarbon group, or R$^3$ is optionally bonded to a carbon atom or a hetero atom on the aryl group or the heteroaryl group represented by A to form an optionally substituted ring structure, and Y$^1$ is a single bond or an optionally substituted C$_{1-4}$ alkylene or an optionally substituted —O—(C$_{1-4}$ alkylene)-, R$^1$ is a hydrogen atom or an optionally substituted group bonded via a carbon atom, a nitrogen atom or an oxygen atom, and R$^2$ is a hydrogen atom or an optionally substituted group bonded via a carbon atom or a sulfur atom, or R$^1$ and R$^2$, or R$^2$ and R$^3$ are optionally bonded to form an optionally substituted ring structure, provided that the compounds represented by the formulas:

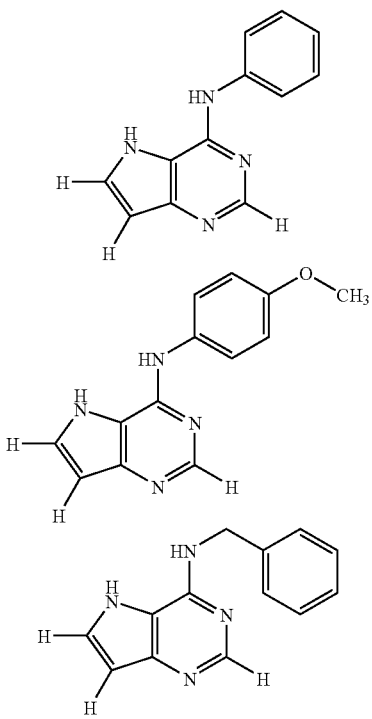

-continued

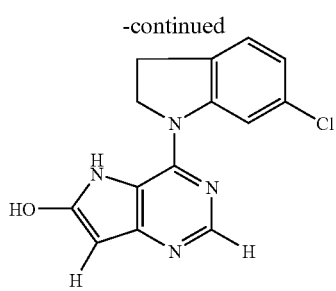

are excluded (sometimes referred to as compound (I) in the present specification), or a salt thereof or a prodrug thereof;

[4] the method of the above-mentioned [1], wherein the HER2 inhibitor is a compound represented by formula:

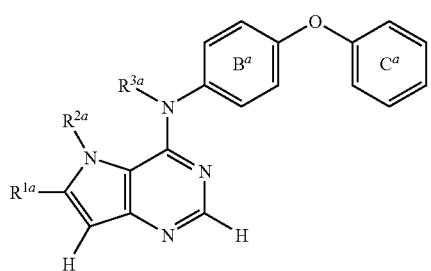

wherein $R^{1a}$ is a hydrogen atom or an optionally substituted group bonded via a carbon atom, a nitrogen atom or an oxygen atom, $R^{2a}$ is an optionally substituted group bonded via a carbon atom or a sulfur atom, or $R^{1a}$ and $R^{2a}$, or $R^{2a}$ and $R^{3a}$ are optionally bonded to form an optionally substituted ring structure, $R^{3a}$ is a hydrogen atom or an optionally substituted aliphatic hydrocarbon group, or $R^{3a}$ is optionally bonded to a carbon atom of the adjacent phenyl group to form an optionally substituted ring structure, $B^a$ is an optionally substituted benzene ring, and $C^a$ is an optionally substituted $C_{6-18}$ aryl group, (sometimes referred to as compound (Ia) in the present specification) or a salt thereof or a prodrug thereof;

[5] the method of the above-mentioned [1], wherein the HER2 inhibitor is N-{2-[4-({3-chloro-4-[3-(trifluoromethyl) phenoxy]phenyl}amino)-5H-pyrrolo[3,2-d]pyrimidin-5-yl] ethyl}-3-hydroxy-3-methylbutanamide or a salt thereof or a prodrug thereof;

[6] the method of the above-mentioned [1], wherein the cancer is breast cancer, prostate cancer, lung cancer, pancreatic cancer, kidney cancer, colorectal cancer, small intestinal cancer, esophagus cancer or gastric cancer;

[7] a method for diagnosis of expression of (1) HER2 and (2) at least one marker selected from the group consisting of (a) HER3, (b) HER4, (c) PTEN, (d) IGF-1R and (e) EGFR;

[8] a kit for the diagnosis method of the above-mentioned [7];

[9] a therapeutic agent for cancer for a patient showing high expression of HER2 and HER3, which comprises a HER2 inhibitor; and the like.

In addition, the present invention relates to

[10] the method of the above-mentioned [1], wherein the HER2 inhibitor is a compound represented by the formula:

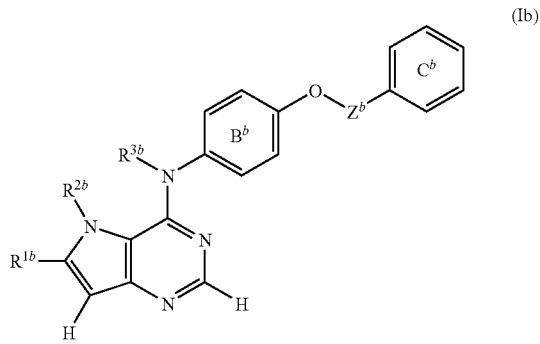

wherein $R^{1b}$ is a hydrogen atom or an optionally substituted group bonded via a carbon atom, a nitrogen atom or an oxygen atom, $R^{2b}$ is an optionally substituted group bonded via a carbon atom or a sulfur atom, or $R^{1b}$ and $R^{2b}$, or $R^{2b}$ and $R^{3b}$ are optionally bonded to form an optionally substituted ring structure, $R^{3b}$ is a hydrogen atom or an optionally substituted aliphatic hydrocarbon group, or $R^{3b}$ is optionally bonded to a carbon atom of the adjacent phenyl group to form an optionally substituted ring structure, $B^b$ is an optionally substituted benzene ring, $C^b$ is an optionally substituted $C_{6-18}$ aryl group, and $Z^b$ is an optionally substituted $C_{1-3}$ alkylene group (hereinafter sometimes to be referred to as compound (Ib) in the present specification) or a salt thereof or a prodrug thereof;

[11] the method of the above-mentioned [1], wherein the HER2 inhibitor is a compound represented by the formula:

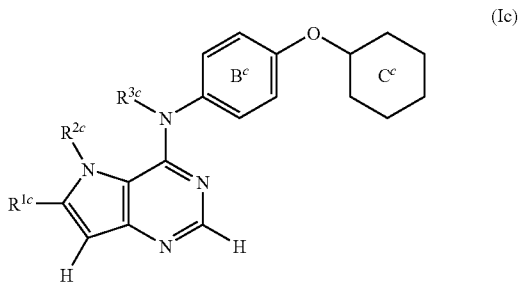

wherein $R^{1c}$ is a hydrogen atom or an optionally substituted group bonded via a carbon atom, a nitrogen atom or an oxygen atom, $R^{2c}$ is an optionally substituted group bonded via a carbon atom or a sulfur atom, or $R^{1c}$ and $R^{2c}$, or $R^{2c}$ and $R^{3c}$ are optionally bonded to form an optionally substituted ring structure, $R^{3c}$ is a hydrogen atom or an optionally substituted aliphatic hydrocarbon group, or $R^{3c}$ is optionally bonded to a carbon atom of the adjacent phenyl group to form an optionally substituted ring structure, $B^c$ is an optionally substituted benzene ring, and $C^c$ is an optionally substituted heterocyclic group (hereinafter sometimes to be referred to as compound (Ic) in the present specification) or a salt thereof or a prodrug thereof;

[12] the method of the above-mentioned [1], wherein the HER2 inhibitor is a compound represented by the formula:

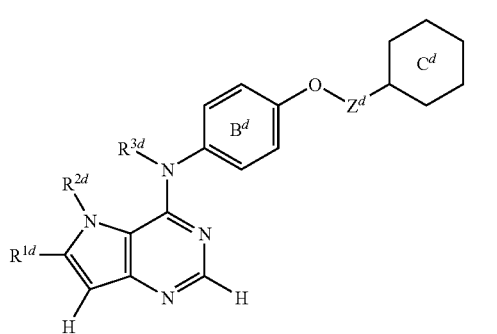

(Id)

wherein $R^{1d}$ is a hydrogen atom or an optionally substituted group bonded via a carbon atom, a nitrogen atom or an oxygen atom, $R^{2d}$ is an optionally substituted group bonded via a carbon atom or a sulfur atom, or $R^{1d}$ and $R^{2d}$, or $R^{2d}$ and $R^{3d}$ are optionally bonded to form an optionally substituted ring structure, $R^{3d}$ is a hydrogen atom or an optionally substituted aliphatic hydrocarbon group, or $R^{3d}$ is optionally bonded to a carbon atom of the adjacent phenyl group to form an optionally substituted ring structure, $B^d$ is an optionally substituted benzene ring, $C^d$ is an optionally substituted heterocyclic group, and $Z^d$ is an optionally substituted $C_{1-3}$ alkylene group, (hereinafter sometimes to be referred to as compound (Id) in the present specification) or a salt thereof or a prodrug thereof;

[13] the method of the above-mentioned [1], wherein the HER2 inhibitor is a compound represented by the formula:

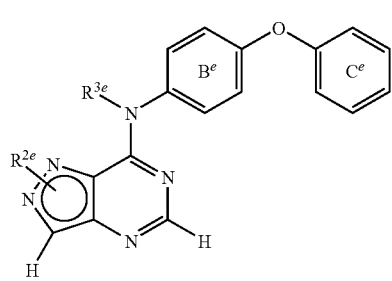

(Ie)

wherein $R^{2e}$ is an optionally substituted group bonded via a carbon atom or a sulfur atom, or $R^{2e}$ and $R^{3e}$ are optionally bonded to form an optionally substituted ring structure, $R^{3e}$ is a hydrogen atom or an optionally substituted aliphatic hydrocarbon group, or $R^{3e}$ is optionally bonded to a carbon atom of the adjacent phenyl group to form an optionally substituted ring structure, $B^e$ is an optionally substituted benzene ring, and $C^e$ is an optionally substituted $C_{6-18}$ aryl group, (hereinafter sometimes to be referred to as compound (Ie) in the present specification) or a salt thereof or a prodrug thereof;

[14] the method of the above-mentioned [1], wherein the HER2 inhibitor is a compound represented by the formula:

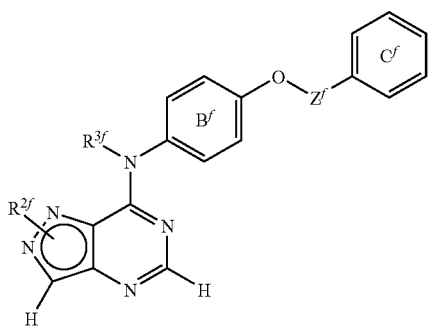

(If)

wherein $R^{2f}$ is an optionally substituted group bonded via a carbon atom or a sulfur atom, or $R^{2f}$ and $R^{3f}$ are optionally bonded to form an optionally substituted ring structure, $R^{3f}$ is a hydrogen atom or an optionally substituted aliphatic hydrocarbon group, or $R^{3f}$ is optionally bonded to a carbon atom of the adjacent phenyl group to form an optionally substituted ring structure, $B^f$ is an optionally substituted benzene ring, $C^f$ is an optionally substituted $C_{6-18}$ aryl group, and $Z^f$ is an optionally substituted $C_{1-3}$ alkylene group, (hereinafter sometimes to be referred to as compound (If) in the present specification) or a salt thereof or a prodrug thereof;

[15] the method of the above-mentioned [1], wherein the HER2 inhibitor is a compound represented by the formula:

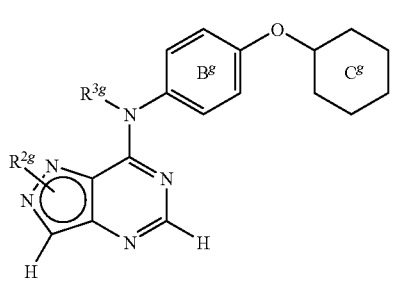

(Ig)

wherein $R^{2g}$ is an optionally substituted group bonded via a carbon atom or a sulfur atom, or $R^{2g}$ and $R^{3g}$ are optionally bonded to form an optionally substituted ring structure, $R^{3g}$ is a hydrogen atom or an optionally substituted aliphatic hydrocarbon group, or $R^{3g}$ is optionally bonded to a carbon atom of the adjacent phenyl group to form an optionally substituted ring structure, $B^g$ is an optionally substituted benzene ring, and $C^g$ is an optionally substituted heterocyclic group, (hereinafter sometimes to be referred to as compound (Ig) in the present specification) or a salt thereof or a prodrug thereof; and the like.

Figure 1:
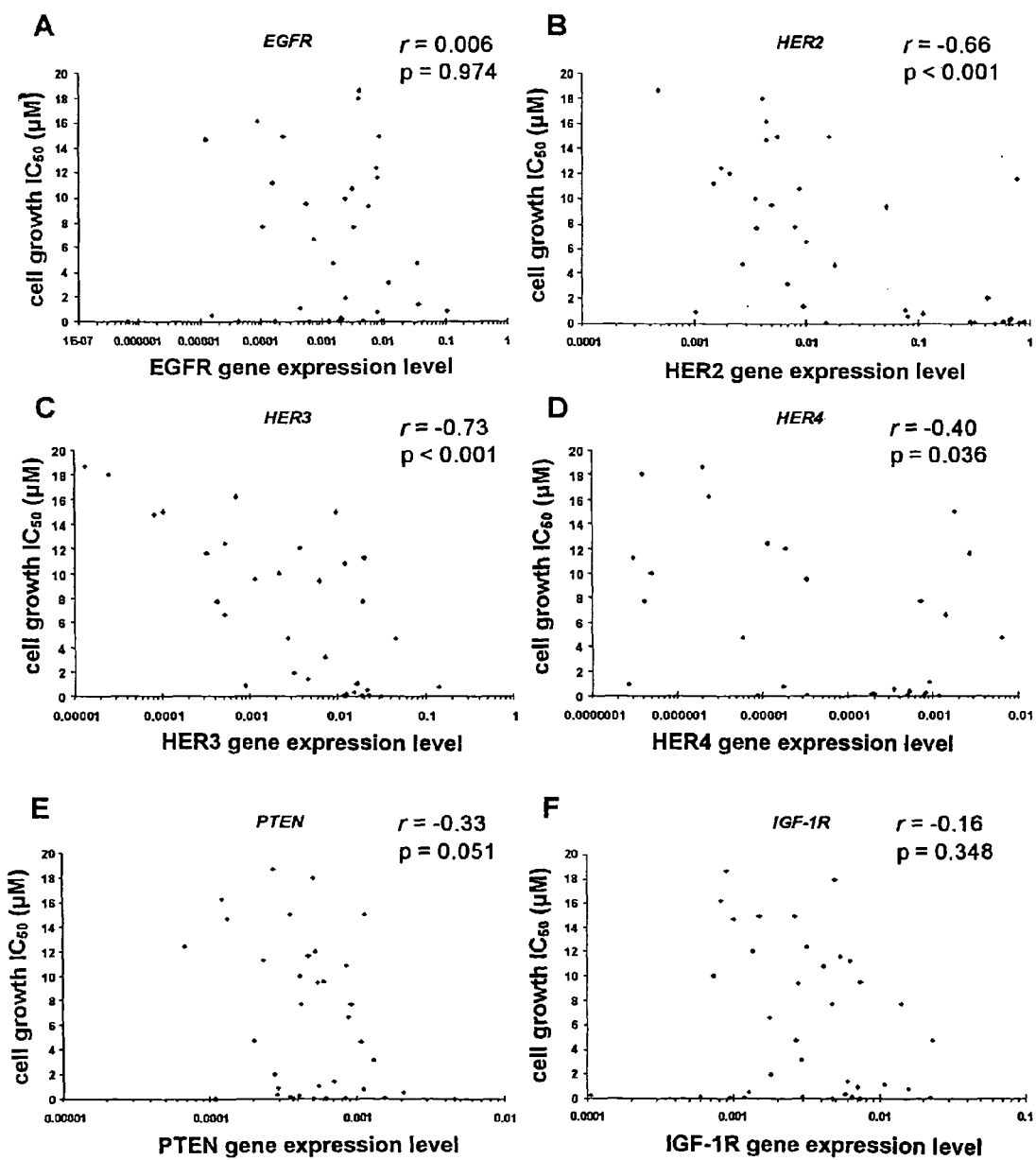
FIG. 1 shows a plot of cell growth inhibitory $IC_{50}$ value of compound X against cultured cell lines and the amount of (A) EGFR, (B) HER2, (c) HER3, (D) HER4, (E) PTEN or (F) IGF-1R gene expression of each cell, wherein the vertical axis shows $IC_{50}$ value (μM) of the cell growth inhibition, and the transverse axis shows expression amount of each gene.

The present invention is explained in detail in the following.

The present invention comprises selecting patients coexpressing HER2 and HER3 and administering an effective amount of a HER2 inhibitor to the patients.

The "patients coexpressing HER2 and HER3" means those showing expression of these proteins in a cancer tissue.

Examples of the method for selecting patients coexpressing HER2 and HER3 include methods including detection of the expression of HER2 and HER3 by immunostaining method using a tissue from cancer patient, in situ hybridization method, mRNA assay, detection of protein by Western blot method and the like.

As a method for determining the expression of HER2 and HER3, for example, gene diagnosis, diagnosis using an antibody and the like can be employed. In the following description, HER2 and HER3 are sometimes to be referred to as a "growth factor receptor" or "receptor".

The gene diagnosis includes DNA diagnosis and mRNA diagnosis. In both cases, DNA or RNA encoding the aforementioned receptor can be used as a probe.

As the aforementioned probe, any of genome DNA, genome DNA library, cDNAs derived from various cells/tissues, DNAs derived from cDNA libraries derived from various cells/tissues or RNA produced from these, synthetic DNA and synthetic RNA can be used. The vector to be used for the library may be any of bacteriophage, plasmid, cosmid, phagemid and the like. In addition, total RNA or mRNA fraction may be prepared from cell/tissue and directly amplified by Reverse Transcriptase Polymerase Chain Reaction (hereinafter to be abbreviated as RT-PCR method).

As the probe of the aforementioned receptor, specifically, a DNA encoding HER2 (Nature, vol. 319, pages 230-234, 1986) and a DNA encoding HER3 (Proceedings of the National Academy of Sciences of the United States of America, vol. 86, pages 9193-9197, 1989) can be used. In addition, the expression of HER4 can also be measured using a DNA encoding HER4 (Proceedings of the National Academy of Sciences of the United States of America, vol. 90, pages 1746-1750, 1993).

Since a probe of a receptor can detect abnormality of DNA or mRNA (gene abnormality) encoding a receptor expressed in a cancer cell, for example, gene diagnosis such as deletion, amplification, recombination (gene fusion), damage, decreased expression, overexpression and the like of the DNA or mRNA can be performed.

The gene diagnosis can be performed, for example, by Southern hybridization, FISH (fluorescence in situ hybridization), Northern hybridization, PCR-SSCP method (Genomics, vol. 5, pages 874-879, 1989; Proceedings of the National Academy of Sciences of the United States of America, vol. 86, pages 2766-2770, 1989), DNA chip method, DNA array method and the like known per se.

The diagnosis by an antibody can be performed using an antibody to the aforementioned receptor. The antibody may be any of polyclonal antibody and monoclonal antibody as long as it can recognize the aforementioned receptor. Since an antibody can recognize amino acid sequence, protein modification, steric structure and the like, for example, an antibody that can recognize change in the protein modification of growth factor receptor such as phosphorylation, acetylation, sugar chain addition and the like, or a structural change of the growth factor receptor, which is free of protein modification, such as change of steric structure etc., and the like can also be used.

As the antibody, a known antibody (e.g., trastuzumab of anti-HER2 antibody) can also be used, or produced using the aforementioned receptor as an antigen according to a production method of antibody or antiserum known per se.

The diagnosis by antibody can be performed, for example, by Western blotting, immunohistological staining method, ELISA method and the like, which are known per se.

[Preparation of Monoclonal Antibody]

(a) Preparation of Monoclonal Antibody Producing Cell

The growth factor can be administered as it is or together with a carrier or a diluent to a site of a mammal which can produce an antibody. In order to enhance the antibody producing ability upon administration, complete Freund's adjuvant or incomplete Freund's adjuvant may be administered. Administration may be performed usually once every 2 to 6 weeks at total times of around 2 to 10. Examples of a mammal to be used include monkey, rabbit, dog, guinea pig, mouse, rat, sheep and gout. Mouse and rat are preferably used.

Upon preparation of a monoclonal antibody producing cell, an individual for which antibody titer was recognized is selected from a warm-blooded animal immunized with an antigen, for example, mouse, spleen or lymph node is taken 2 to 5 days after final immunization, and an antibody producing cell contained therein can be used with a myeloma cell to prepare a monoclonal antibody producing hybridoma. Measurement of an antibody titer in an antiserum can be performed, for example, by reacting the labeled growth factor described below with an antiserum and, thereafter, measuring the activity of a labeling agent bound to an antibody. The fusion procedure can be performed by the known method, for example, a method of Kohler and Milstein [Nature, vol. 256, page 495 (1975)]. As a fusion promoting agent, for example, there are polyethylene glycol (PEG) and Sendaivirus. Preferably, PEG is used.

Examples of the myeloma cell include NS-1, P3U1, SP2/0 and the like. P3U1 is preferably used. A preferable ratio of the number of an antibody producing cell (spleen) and the number of myeloma cell to be used is around 1:1 to 20:1. Cell fusion can be performed effectively by adding PEG (preferably PEG 1000 to PEG 6000) at the concentration of around 10 to 80% and incubating at about 20 to 40° C., preferably 30 to 37° C., for about 1 to 10 min.

For screening a monoclonal antibody producing hybridoma, a number of methods can be used. For example, there are a method of adding a hybridoma culturing supernatant to a solid phase (for example, microplate) onto which the growth factor is adsorbed directly or together with a carrier, adding an anti-immunoglobulin antibody (when a cell used for cell fusion is a murine cell, an anti-mouse immunoglobulin antibody is used) labeled with an radioactive substance or an enzyme, or protein A, and detecting a monoclonal antibody bound to the solid phase, and a method of adding a hybridoma culturing supernatant to a solid phase onto which an anti-immunoglobulin antibody or protein A is absorbed, adding the growth factor labeled with a radioactive substance or an enzyme, and detecting a monoclonal antibody bound to the solid phase.

Although selection of a monoclonal antibody can be performed by method known per se or similar method, it can be usually performed on a medium for an animal cell to which HAT (hypoxanthine, aminopterin, thymidine) has been added. As a medium for selection and growth, any medium can be used as long as a hybridoma can grow on the medium. For example, RPMI 1640 medium containing 1 to 20%, preferably 10 to 20% bovine fetal serum, GIT medium containing 1 to 10% bovine fatal serum (Wako Pure Chemical Industries, Ltd.) or serum free medium for culturing hybridoma (SFM-101, Nissui Pharmaceutical Co., Ltd.) can be used. A culturing temperature is usually 20 to 40° C., preferably about 37° C. A culturing time is usually 5 days to 3 weeks, preferably 1 week to 2 weeks. Culturing can be performed usually under 5% carbonic acid gas. An antibody titer in a hybridoma culturing supernatant can be measured as in the aforementioned measurement of an antibody titer in an antiserum.

(b) Purification of Monoclonal Antibody

Separation and purification of a monoclonal antibody can be performed according to a method for separating and purifying an immunoglobulin [for example, salting out method, alcohol precipitation method, isoelectric precipitation method, electrophoresis method, adsorption and desorption method using an ion exchanger (for example DEAE), ultracentrifugation method, gel filtration method, and specific purifying method by taking only an antibody with an antigen-bound solid phase or an active adsorbing agent such as protein A or protein G, and dissociating a bond to obtain antibody] as in the conventional separation and purification of a polyclonal antibody.

[Preparation of Polyclonal Antibody]

The polyclonal antibody used in the present invention can be prepared by the method known per se or similar method. For example, the polyclonal antibody can be prepared by forming a complex of an immunogen (growth factor) and a carrier protein, immunizing a mammal as in the aforementioned preparation of a monoclonal antibody, taking a material containing an antibody to the growth factor from the immunized animal, and separating and purifying an antibody.

Regarding a complex of an immunogen and a carrier protein for immunizing a mammal, a kind of carrier protein and a mixing ratio of carrier and hapten may be any ones so long as an antibody can be effectively bound to a hapten immunized by cross-linking with carrier. For example, a method is used in which bovine serum albumin, bovine thyroglobulin, keyhole limpet hemocyanin and the like is coupled to a hapten at a rate by weight of about 0.1 to 20, preferably about 1 to 5 relative to hapten.

In addition, a variety of condensing agents can be used for coupling a hapten and a carrier, and glutaraldehyde and carbodiimide, maleimide active ester, and active ester regent containing a thiol group or a dithiopyridyl group are used.

A condensed product is administered to a warm-blooded animal at a site which can produce an antibody as it is or together with a carrier or a diluent. In order to enhance the antibody producing ability upon administration, complete Freund's adjuvant and incomplete Freund's adjuvant may be administered. Administration can be performed usually once every about 2 to 6 weeks at a total of 3 to 10 times.

A polyclonal antibody can be taken from blood or ascites, preferably blood of a mammal immunized by the above-mentioned method.

A polyclonal antibody titer in antiserum can be measured as in the aforementioned measurement of an antibody titer in serum. Separation and purification of a polyclonal antibody can be performed according to the similar method for separating and purifying immunoglobulin to the above-mentioned separation and purification of a monoclonal antibody.

Since an antibody can specifically recognize the aforementioned growth factor, a growth factor in a test solution can be quantified according to sandwich immunoassay and the like. For example, a growth factor is quantified by (i) competitively reacting an antibody with a test solution and a labeled growth factor and measuring the rate of the labeled growth factor bound with the antibody, or (ii) simultaneously or continuously reacting a test solution with an antibody insolubilized on a carrier and a labeled antibody, and determining the activity of the labeling agent on the insolubilized carrier.

In the above (ii), it is preferable that one of antibodies is an antibody which recognizes an N-terminal of the growth factor and the other of the antibodies is an antibody which reacts with a C-terminal of the growth factor.

Not only measurement of the growth factor can be performed using a monoclonal antibody against the growth factor (hereinafter, referred to as the monoclonal antibody in some cases), but also detection by tissue staining can be performed. For these purposes, an antibody molecule itself may be used, or, alternatively, $F(ab')_2$, Fab' or Fab fraction of an antibody molecule may be used. A method for measurement using the antibody against the growth factor is not particularly limited but any measuring methods may be used as long as they are a method for measurement by detecting an amount of an antibody, an antigen or an antibody-antigen complex corresponding to an amount of an antigen in a test solution (for example, a protein amount of the growth factor) by chemical or physical means, and calculating this amount from a standard curve made using a standard solution containing the known amount of an antigen. Although, for example, nephrometery, competitive method, immunometric method and sandwich method are suitably used, it is particularly preferable to use a sandwich method described below in respect of the sensitivity and the specificity.

As a labeling agent used for a measuring method using a labeled substance, for example, radioisotopes, enzymes, fluorescent substances and luminescent substances are used. As the radioisotope, for example, $[^{125}I]$, $[^{131}I]$, $[^{3}H]$, $[^{14}C]$ are used. As the above enzyme, an enzyme which is stable and has large specific activity is preferable and, for example, β-galactosidase, β-glucosidase, alkaline phosphatase, peroxidase and malate dehydrogenase are used. As the fluorescent substance, for example, fluorescamine and fluorescein isothiocyanate are used. As the luminescent substance, for example, luminol, luminol derivative, luciferin and lucigenin are used. Further, the biotin-avidin system can be used for binding an antibody or an antigen with a labeling agent.

Upon insolubilization of an antigen or an antibody, physical adsorption may be used, or chemical bonding normally used for insolubilizing or immobilizing a protein or an enzyme may be used. As the carrier, for example, insoluble polysaccharides such as agarose, dextran and cellulose, synthetic resins such as polystyrene, polyacrylamide and silicone, and glass are used.

In a sandwich method, the protein amount of the growth factor in a test solution can be quantified by reacting a test solution with the insolubilized monoclonal antibody (primary reaction), further reacting with another monoclonal antibody labeled (secondary reaction), and measuring the activity of a labeling agent on the insolubilized carrier. The primary reaction and the secondary reaction may be performed in a reverse order, or, alternatively, they may be performed simultaneously or at different times. The labeling agent and the insolubilizing method can be according to those described above.

In addition, in an immunoassay by a sandwich method, an antibody used for a solid phase antibody or a labeling antibody is not necessarily one kind, and a mixture of two or more kinds of antibodies may be used for the purpose of enhancing the measuring sensitivity.

In a method for measuring the growth factor by the sandwich method, as the monoclonal antibodies used for the primary reaction and the secondary reaction, antibodies having a different site to which the growth factor is bound are preferably used. That is, in antibodies used for the primary reaction and the secondary reaction, for example, when an antibody used for secondary reaction recognizes a C-terminal of the growth factor, as an antibody used for the primary reaction, an antibody which preferably recognizes a part other than a C-terminal, for example, an N-terminal is used.

The monoclonal antibody can be used for a measuring system other than the sandwich method, for example, a competitive method, an immunometric method or nephrometry. In the competitive method, after an antigen in a test solution and a labeled antigen are reacted with an antibody competitively, an unreacted labeled antigen (F) and a labeled antigen bound to an antibody (B) are separated (B/F separation), a labeled amount of either of B or F is measured and an antigen in the test solution is quantified. In the present reaction method, there are used a solution method in which a soluble antibody is used as an antibody and polyethylene glycol and the second antibody to the above antibody are used for B/F separation, and a solid phase immobilization method in which a solid-phase immobilized antibody is used as the first antibody, or a soluble antibody is used as the first antibody and a solid-phase immobilized antibody is used as the second antibody.

In the immunometric method, an antigen in a test solution and a solid-phase immobilized antigen are reacted competitively with a predetermined amount of a labeled antibody, then a solid phase and a solution phase are separated, or an antigen in a test solution and an excessive amount of a labeled antibody are reacted, then a solid-phase immobilized antigen is added to bind an unreacted labeled antibody to a solid phase, and a solid phase and a solution phase are separated. Then, a labeled amount of either phase is measured to quantify an antigen in a test solution.

In addition, in nephrometry, an amount of insoluble precipitates produced as a result of an antigen-antibody reaction in a gel or a solution is measured. Even when an amount of an antigen in a test solution is small and only a small of amount of precipitates are obtained, laser nephrometry utilizing laser scattering is suitably used.

When these individual immunoassays are applied to the present measuring method, setting of the special conditions and operations is not required. The system for measuring the epithelial growth factor may be constructed by adding the normal technical consideration of a person skilled in the art to the normal conditions and operations in respective methods. For the details of these general technical means, review and books may be referenced [for example, see "Radioimmunoassay" ed. by Hiroshi Irie (published by Kodansha in 1974), "Radioimmunoassay, Second Series" ed. by Hiroshi Irie (published by Kodansha in 1979), "Enzyme Immunoassay" ed. by Eiji Ishikawa et al. (published by Igakushoin in 1978), "Enzyme Immunoassay" ed. by Eiji Ishikawa et al. (2nd edition) (published by Igakushoin in 1982), "Enzyme Immunoassay" ed. by Eiji Ishikawa et al. (3rd edition) (published by Igakushoin in 1987), "Methods in ENZYMOLOGY" Vol. 70 (Immunochemical Techniques (Part A)), ibid. Vol. 73 (Immunochemical Techniques (Part B)), ibid. Vol. 74 (Immunochemical Techniques (Part C)), ibid. Vol. 84 (Immunochemical Techniques (Part D: Selected Immunoassays)), ibid. Vol. 92 (Immunochemical Techniques (Part E: Monoclonal Antibodies and General Immunoassay Methods)), ibid. Vol. 121 (Immunochemical Techniques (Part I: Hybridoma Technology and Monoclonal Antibodies)) all published by Academic Press Inc.].

As mentioned above, using an antibody, the expression level of HER2 and HER3 can be quantified with high sensitivity.

In addition, using the above-mentioned selection method, the expression of (1) HER2 and (2) at least one marker selected from the group consisting of (a) HER3, (b) HER4, (c) PTEN, (d) IGF-1R and (e) EGFR can be diagnosed.

The diagnosis method of the present invention includes measuring the expression of (1) HER2 and (2) at least one marker selected from the group consisting of (a) HER3, (b) HER4, (c) PTEN, (d) IGF-1R and (e) EGFR in a sample obtained from a test subject.

The diagnosis method of the present invention preferably includes measuring the expression of HER2 and HER3 in a sample obtained from a test subject. Furthermore, it may include measuring the expression of at least one marker selected from the group consisting of HER4, PTEN, IGF-1R and EGFR in the sample.

The present invention also provides a method of examining the sensitivity to a HER2 inhibitor, which comprises measuring the expression of (1) HER2 and (2) at least one marker selected from the group consisting of (a) HER3, (b) HER4, (c) PTEN, (d) IGF-1R and (e) EGFR in the sample obtained from a test subject.

The examination method of the present invention preferably includes measuring the expression of HER2 and HER3 in a sample obtained from a test subject. Furthermore, it may include measuring the expression of at least one marker selected from the group consisting of HER4, PTEN, IGF-1R and EGFR in a sample obtained from a test subject.

As the sample, a biological sample such as a tumor cell and the like can be used.

As the test subject, a cancer patient can be mentioned.

For the assay of the expression of HER2, HER3, HER4, PTEN, IGF-1R and/or EGFR, the aforementioned gene diagnosis or diagnosis by antibody and the like can be employed.

The assay results of the expression level of HER2 and the expression level of at least one marker selected from the group consisting of (a) HER3, (b) HER4, (c) PTEN, (d)

IGF-1R and (e) EGFR (preferably HER3) are compared with the standard level employed, and when the expression levels of HER2 and HER3 are higher than the standard level, the test subject is judged as being sensitive to a HER2 inhibitor.

The present invention also provides a kit to be used for the above-mentioned diagnosis method.

The kit of the present invention contains (1) a reagent for assaying the expression of HER2, and a reagent for assaying the expression of at least one marker selected from the group consisting of (2) (a) HER3, (b) HER4, (c) PTEN, (d) IGF-1R and (e) EGFR.

The kit of the present invention preferably contains (1) a reagent for assaying the expression of HER2, and (2) a reagent for assaying the expression of HER3. Furthermore, it may contain a reagent for assaying the expression of at least one marker selected from the group consisting of HER4, PTEN, IGF-1R and EGFR.

The kit of the present invention can be used as a kit for examining the sensitivity to a HER2 inhibitor.

The present invention also provides a therapeutic agent for cancer for patients showing high expression of HER2 and HER3, which comprises a HER2 inhibitor.

The "patients showing high expression of HER2 and HER3" means those wherein the expression of these proteins (or mRNA) is elevated as compared with normal tissues.

In the specification, the HER2 inhibitor is not particularly limited as long as it inhibits HER2. Examples of the HER2 inhibitor include lapatinib

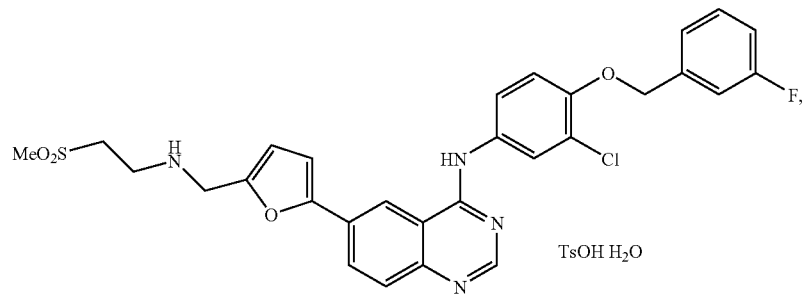

TsOH H$_2$O a compound represented by the formula

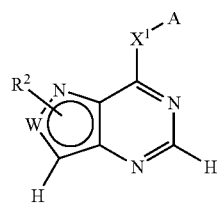

(I)

wherein W is C(R$^1$) or N,

A is an optionally substituted aryl group or an optionally substituted heteroaryl group, X$^1$ is —NR$^3$—Y$^1$—, —O—, —S—, —SO—, —SO$_2$— or —CHR$^3$— wherein R$^3$ is a hydrogen atom or an optionally substituted aliphatic hydrocarbon group, or R$^3$ is optionally bonded to a carbon atom or a hetero atom on the aryl group or the heteroaryl group represented by A to form an optionally substituted ring structure, and Y$^1$ is a single bond or an optionally substituted C$_{1-4}$ alkylene or an optionally substituted —O—(C$_{1-4}$ alkylene)-, R$^1$ is a hydrogen atom or an optionally substituted group bonded via a carbon atom, a nitrogen atom or an oxygen atom, and R$^2$ is a hydrogen atom or an optionally substituted group bonded via a carbon atom or a sulfur atom, or R$^1$ and R$^2$, or R$^2$ and R$^3$ are optionally bonded to form an optionally substituted ring structure, provided that the compounds represented by the formulas

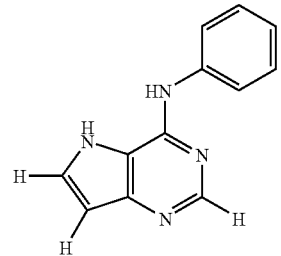

-continued

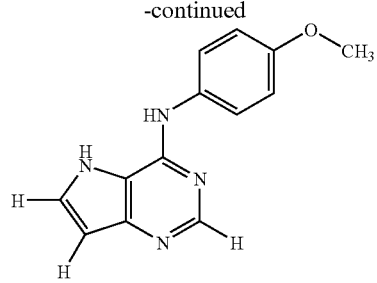

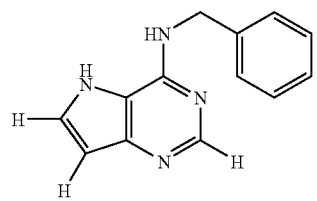

-continued

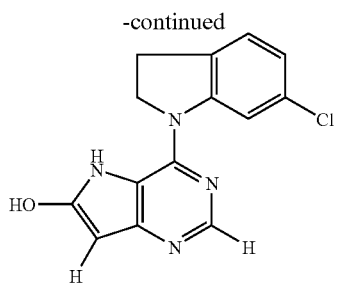

are excluded, or a salt thereof or a prodrug thereof and the like.

The definitions of the substituents in the structural formulas are described in the following.

In the present specification, unless otherwise specified, the "aryl" in the "aryl group" and the substituents includes a monocyclic aryl group and a fused polycyclic aryl group. As the "aryl group", for example, a $C_{6-18}$ aryl group can be mentioned. As the "$C_{6-18}$ aryl group", for example, phenyl, biphenylyl, naphthyl, anthryl, phenanthryl and acenaphthylenyl can be mentioned.

In the present specification, as the "heterocyclic group" (and "heterocyclyl-" in the substituents), for example, a 5- to 8-membered heteroaryl group or a saturated or unsaturated aliphatic heterocyclic group containing, as an atom (ring atom) constituting a ring system, one or more (preferably 1 to 4, more preferably 1 or 2) hetero atoms selected from an oxygen atom, an optionally oxidized sulfur atom and a nitrogen atom and the like (preferably, an oxygen atom, a sulfur atom and a nitrogen atom etc.) can be mentioned.

In the present specification, unless otherwise specified, as the "aliphatic hydrocarbon group", a linear or branched aliphatic hydrocarbon group having 1 to 15 carbon atoms (preferably, 1 to 8 carbon atoms) can be mentioned. As such "aliphatic hydrocarbon group", for example, a $C_{1-6}$ alkyl group, a $C_{2-8}$ alkenyl group, a $C_{2-8}$ alkynyl group, a $C_{3-8}$ cycloalkyl group and the like can be mentioned.

In the present specification, unless otherwise specified, as the "heteroaryl group", an aromatic monocyclic heterocyclic group (e.g., 5- or 6-membered aromatic monocyclic heterocyclic group such as furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, triazinyl and the like) and an aromatic fused heterocyclic group (e.g., 8- to 12-membered aromatic fused heterocyclic group such as benzofuranyl, isobenzofuranyl, benzothienyl, indolyl, isoindolyl, 1H-indazolyl, benzindazolyl, benzoxazolyl, 1,2-benzisoxazolyl, benzothiazolyl, benzopyranyl, 1,2-benzisothiazolyl, 1H-benzotriazolyl, quinolyl, isoquinolyl, cinnolinyl, quinazolinyl, quinoxalinyl, phthalazinyl, naphthyridinyl, purinyl, pteridinyl, carbazolyl, α-carbolinyl, β-carbolinyl, γ-carbolinyl, acridinyl, phenoxazinyl, phenothiazinyl, phenazinyl, phenoxathiinyl, thianthrenyl, phenanthridinyl, phenanthrolinyl, indolizinyl, pyrrolo[1,2-b]pyridazinyl, pyrazolo[1,5-a]pyridyl, imidazo[1,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl, 1,2,4-triazolo[4,3-b]pyridazinyl and the like) and the like can be mentioned. As the aromatic fused heterocyclic group, a heterocycle wherein the aforementioned 5- or 6-membered aromatic monocyclic heterocyclic group is fused with a benzene ring and a heterocycle wherein the same or different two heterocycles of the aforementioned 5- or 6-membered aromatic monocyclic heterocyclic group are fused are preferable.

In the present specification, unless otherwise specified, as the "aliphatic heterocyclic group", for example, a 3- to 8-membered (preferably 5- or 6-membered) saturated or unsaturated (preferably saturated) aliphatic heterocyclic group such as oxiranyl, azetidinyl, oxetanyl, thietanyl, pyrrolidinyl, tetrahydrofuryl, thiolanyl, piperidyl, tetrahydropyranyl, morpholinyl, thiomorpholinyl, piperazinyl, dihydro-1,2,4-oxadiazolyl and the like, and the like can be mentioned.

In the present specification, unless otherwise specified, as the "$C_{1-8}$ alkyl group", for example, methyl, ethyl, n-propyl, i-propyl, n-butyl, i-butyl, s-butyl, t-butyl, n-pentyl, i-pentyl, t-pentyl, neopentyl, n-hexyl, i-hexyl, n-heptyl and n-octyl and the like can be mentioned, with preference given to a $C_{1-6}$ alkyl group. In the present specification, moreover, unless otherwise specified, as the "$C_{1-4}$ alkyl group", for example, methyl, ethyl, n-propyl, i-propyl, n-butyl and i-butyl can be mentioned.

In the present specification, unless otherwise specified, as the "$C_{2-8}$ alkenyl group", for example, vinyl, (1- or 2-)propenyl, (1-, 2- or 3-)butenyl, pentenyl, octenyl and (1,3-)butadienyl can be mentioned, with preference given to a $C_{2-4}$ alkenyl group.

In the present specification, unless otherwise specified, as the "$C_{2-8}$ alkynyl group", for example, ethynyl, (1- or 2-)propynyl, (1-, 2- or 3-)butynyl, pentynyl and octynyl can be mentioned, with preference given to a $C_{2-4}$ alkynyl group.

In the present specification, unless otherwise specified, as the "$C_{3-8}$ cycloalkyl group", for example, cyclopropyl, cyclobutyl, cyclopentyl, cyclohexyl, cycloheptyl and cyclooctyl can be mentioned, with preference given to a $C_{3-6}$ cycloalkyl group.

In the present specification, unless otherwise specified, as the "$C_{1-4}$ alkylene", for example, methylene, ethylene, trimethylene, tetramethylene and propylene and the like can be mentioned.

In the present specification, unless otherwise specified, as the "—O—($C_{1-4}$ alkylene)-", for example, —OCH$_2$—, —OCH$_2$CH$_2$—, —O(CH$_2$)$_3$—, —O(CH$_2$)$_4$—, —OCH(CH$_3$)—, —OC(CH$_3$)$_2$—, —OCH(CH$_3$)$_2$CH$_2$—, —OCH$_2$CH(CH$_3$)—, —OC(CH$_3$)$_2$CH$_2$— and —OCH$_2$C(CH$_3$)$_2$— and the like can be mentioned.

In the present specification, unless otherwise specified, as the "$C_{6-18}$ aryl-carbonyl group", for example, benzoyl, naphthoyl, anthrylcarbonyl, phenanthrylcarbonyl and acenaphthylenylcarbonyl and the like can be mentioned.

In the present specification, unless otherwise specified, as the "$C_{6-18}$ aryl-$C_{1-4}$ alkyl-carbonyl group", for example, benzylcarbonyl, 3-phenylpropionyl, 2-phenylpropionyl, 4-phenylbutyryl and 5-phenylpentanoyl and the like can be mentioned.

In the present specification, unless otherwise specified, as the "halogen", fluorine, chlorine, bromine and iodine can be mentioned.

As the "5- to 8-membered heterocyclyl-carbonyl group containing 1 to 3 hetero atoms selected from a nitrogen atom, an oxygen atom and a sulfur atom", "a 5- to 8-membered cyclic amino-carbonyl group optionally having 1 or 2 hetero atoms selected from a nitrogen atom, an oxygen atom and a sulfur atom" is preferable, for example, pyrrolidin-1-ylcarbonyl, piperidin-1-ylcarbonyl, piperazin-1-ylcarbonyl, morpholin-4-ylcarbonyl, thiomorpholin-4-ylcarbonyl and the like can be mentioned.

In the above-mentioned formula, as the "aryl group" for A, a $C_{6-18}$ aryl group is preferable, and phenyl is more preferable.

The "aryl group" for A is optionally substituted by a group represented by the formula —$Y^2$—B wherein $Y^2$ is a single bond, —O—, —O—($C_{1-3}$ alkylene)- (preferably —OCH$_2$—), —NH— or —S—, and B is an aryl group, a heterocyclic group, a $C_{3-8}$ cycloalkyl group, a carbamoyl group, a ureido group, a $C_{6-18}$ aryl-carbonyl group or a $C_{6-18}$ aryl-$C_{1-4}$ alkyl-carbonyl group, each of which is optionally substituted.

As $Y^2$, a single bond, —O— or —OCH$_2$— is preferable, and —O— or —OCH$_2$— is more preferable. Particularly —O— is preferable.

As the "aryl group" for B, a $C_{6-18}$ aryl group is preferable, and phenyl is more preferable.

As the "heterocyclic group" for B, the aforementioned "5- or 6-membered aromatic monocyclic heterocyclic group" is preferable, and pyridyl is more preferable.

The "aryl group", "heterocyclic group", "$C_{6-18}$ aryl-carbonyl group" or "$C_{6-18}$ aryl-$C_{1-4}$ alkyl-carbonyl group" for B may have, for example, 1 to 5, the same or different substituents selected from halogen, optionally halogenated $C_{1-4}$ alkyl, hydroxy, optionally halogenated $C_{1-4}$ alkyloxy, $C_{1-4}$ alkyloxymethyl, hydroxyl-$C_{1-4}$ alkyl, $C_{1-4}$ alkyl-carbonyl, carboxy, $C_{1-4}$ alkoxy-carbonyl, cyano, carbamoyl, sulfamoyl, nitro, amino, $C_{1-4}$ alkyl-carbonylamino, $C_{1-4}$ alkoxy-carbonylamino and $C_{1-4}$ alkyl-sulfonylamino, at any substitutable position(s). As the substituent of the "aryl group" for B, halogen, optionally halogenated $C_{1-4}$ alkyl, optionally halogenated $C_{1-4}$ alkyloxy and the like are preferable and, for example, fluorine, chlorine, trifluoromethyl, trifluoromethoxy and the like can be mentioned. Of these, optionally halogenated $C_{1-4}$ alkyl (e.g., trifluoromethyl) and the like are preferable.

The "aryl group" for A may further have, besides the above-mentioned a group represented by the formula —$Y^2$—B, 1 to 5, the same or different substituents at substitutable optional position(s). As such substituent, substituents similar to those exemplified for the "aryl group" or "heterocyclic group" for B can be mentioned. As such substituent, halogen, optionally halogenated $C_{1-4}$ alkyl and the like are preferable, such as chlorine, methyl and the like can be mentioned. Of these, halogen (e.g., chlorine) is preferable.

As A, for example, 3-chloro-4-[3-(trifluoromethyl)phenoxy]phenyl, 3-chloro-4-[(3-fluorobenzyl)oxy]phenyl, 3-methyl-4-[3-(trifluoromethoxy)phenoxy]phenyl, 3-chloro-4-(3-chlorophenoxy)phenyl, 3-chloro-4-[3-(trifluoromethoxy)phenoxy]phenyl and the like can be mentioned. Of these, 3-chloro-4-[3-(trifluoromethyl)phenoxy]phenyl and the like are preferable.

As the "aliphatic hydrocarbon group" for $R^3$, a $C_{1-8}$ alkyl group, a $C_{2-8}$ alkenyl group, a $C_{2-8}$ alkynyl group and a $C_{3-8}$ cycloalkyl group are preferable.

The "aliphatic hydrocarbon group" for $R^3$ is optionally substituted by 1 to 3 substituents selected from halogen, hydroxy, $C_{1-4}$ alkyloxy, $C_{1-4}$ alkyl-carbonyl, carboxy, $C_{1-4}$ alkoxy-carbonyl, cyano, carbamoyl, sulfamoyl, nitro, amino, $C_{1-4}$ alkyl-carbonylamino, $C_{1-4}$ alkoxy-carbonylamino and $C_{1-4}$ alkyl-sulfonylamino.

The "$C_{1-4}$ alkylene" and "—O—($C_{1-4}$ alkylene)-" for $Y^1$ are optionally substituted by 1 to 3 substituents selected from halogen, hydroxy, $C_{1-4}$ alkyloxy, $C_{1-4}$ alkyl-carbonyl, carboxy, $C_{1-4}$ alkoxy-carbonyl, cyano, carbamoyl, sulfamoyl, nitro, amino, $C_{1-4}$ alkyl-carbonylamino, $C_{1-4}$ alkoxy-carbonylamino and $C_{1-4}$ alkyl-sulfonylamino.

As $X^1$, —NR$^3$— wherein $R^3$ is as defined above is preferable.

As $R^3$, a hydrogen atom is preferable.

As W, C($R^1$) is preferable.

As $R^1$, a hydrogen atom is preferable.

As the "optionally substituted group bonded via a carbon atom, a nitrogen atom or an oxygen atom" for $R^1$, a group of the formula —$X^2$—$R^4$ can be mentioned, wherein $X^2$ is a single bond, —NH— or —O—, and $R^4$ is a hydrogen atom, a cyano group, or a $C_{1-8}$ alkyl group, a $C_{2-8}$ alkenyl group, a $C_{2-8}$ alkynyl group, a carbamoyl group, a $C_{1-6}$ alkyl-carbonyl group, a $C_{3-8}$ cycloalkyl group, a $C_{6-18}$ aryl group, a $C_{6-18}$ aryl-$C_{1-4}$ alkyl group, a $C_{6-18}$ aryl-carbonyl group, a $C_{6-18}$ aryl-$C_{1-4}$ alkyl-carbonyl group, a heterocyclic group, a heterocyclyl-$C_{1-4}$ alkyl group, a heterocyclyl-carbonyl group or a heterocyclyl-$C_{1-4}$ alkyl-carbonyl group, each of which is optionally substituted.

The "$C_{1-8}$ alkyl group", "$C_{2-8}$ alkenyl group", "$C_{2-8}$ alkynyl group", "$C_{1-8}$ alkyl-carbonyl group", "$C_{3-8}$ cycloalkyl group", "$C_{6-18}$ aryl group", "$C_{6-18}$ aryl-$C_{1-4}$ alkyl group", "$C_{6-18}$ aryl-carbonyl group", "$C_{6-18}$ aryl-$C_{1-4}$ alkyl-carbonyl group", "heterocyclic group", "heterocyclyl-$C_{1-4}$ alkyl group", "heterocyclyl-carbonyl group" and "heterocyclyl-$C_{1-4}$ alkyl-carbonyl group" are, for example, optionally substituted by one or more (preferably 1 to 5, more preferably 1 to 3) substituent(s) selected from the group consisting of (a) halogen, (b) oxo, (c) optionally halogenated $C_{1-4}$ alkyl, (d) —(CH$_2$)$_m$-Q, (e) —(CH$_2$)$_m$—$Z^1$— (optionally halogenated $C_{1-4}$ alkyl), (f) —(CH$_2$)$_m$—$Z^1$—$C_{3-8}$ cycloalkyl, (g) —(CH$_2$)$_m$—$Z^2$ (CH$_2$)$_n$-Q, (h) —(CH$_2$)$_m$—$Z^2$—(CH$_2$)$_n$—$Z^1$— (optionally halogenated $C_{1-4}$ alkyl), (i) —(CH$_2$)$_m$—$Z^2$—(CH$_2$)$_n$—$Z^1$—$C_{3-8}$ cycloalkyl, (j) —(CH$_2$)$_m$—$Z^1$— (optionally substituted heterocyclic group)

(preferably, said heterocyclic group is a 5- to 8-membered heterocyclic group having 1 to 3 hetero atoms selected from a nitrogen atom, an oxygen atom and an optionally oxidized sulfur atom)

(k) —(CH$_2$)$_m$—$Z^2$—$C_{1-4}$ alkoxy, and (l) —(CH$_2$)$_m$—$Z^2$—(CH$_2$)$_n$—$Z^1$—(CH$_2$)$_n$—$Z^1$—$C_{1-4}$ alkyl (hereinafter to be sometimes to be referred to as substituent group T).

In these formulas, m is an integer of 0 to 4, n is an integer of 1 to 4,

Q is hydroxy, carboxy, cyano, nitro, —NR$^6$R$^7$, —CONR$^6$R$^7$ or —SO$_2$NR$^6$R$^7$, $Z^1$ is —O—, —CO—, —C(OH)R$^8$—, —C(=N—OR$^8$)—, —S—, —SO—, —SO$_2$—, —N(COR$^8$)—, —N(CO$_2$R$^9$)—, —N(SO$_2$R$^8$)—, —CO—O—, —O—CO—, —CO—NR$^8$—, —NR$^8$—CO—, —NR$^8$—CO$_2$—, —NR$^8$—CO—NH—, —NR$^8$—SO$_2$—, or —NR$^8$—C(=NH)—NH—, and $Z^2$ is —O—, —CO—, —C(OH)R$^8$—, —C(=N—OR$^8$)—, —S—, —SO—, —SO$_2$—, —NR$^8$—, —N(COR$^8$)—, —N(CO$_2$R$^9$)—, —N(SO$_2$R$^9$)—, —CO—O—, —O—CO—, —CO—NR$^8$—, —NR$^8$—CO—, —NR$^8$—

$CO_2$—, —$NR^8$—CO—NH—, —$NR^8$—C(=NH)—NH—, —$NR^8$—$SO_2$—, or —$SO_2$—$NR^8$—. In these formulas, $(CH_2)_m$ and $(CH_2)_n$ are optionally substituted by one or more (preferably 1 to 5, more preferably 1 to 3) substituents selected from, for example, halogen, optionally halogenated $C_{1-4}$ alkyl and hydroxy, and when m or n is not less than 2, a subset —$CH_2CH_2$— of $(CH_2)_m$ and $(CH_2)_n$ is optionally replaced by —CH=CH— or —C≡C—.

In these formulas, $R^6$ and $R^7$ are the same or different and each is a hydrogen atom or $C_{1-4}$ alkyl, or $R^6$ and $R^7$ form a ring together with a nitrogen atom. In these formulas, moreover, $R^8$ is a hydrogen atom or $C_{1-4}$ alkyl and $R^9$ is $C_{1-4}$ alkyl. When $R^6$ and $R^7$ form a ring together with a nitrogen atom, as the nitrogen-containing heterocyclic group, for example, a 3- to 8-membered (preferably 5- or 6-membered) saturated or unsaturated (preferably saturated) aliphatic heterocyclic group such as azetidinyl, pyrrolidinyl, piperidinyl, homopiperidinyl, heptamethyleneimino, morpholinyl, thiomorpholinyl, piperazinyl, homopiperazinyl and the like, and the like can be mentioned.

As $X^2$, a single bond is preferable.

As $R^4$, a hydrogen atom or a $C_{1-8}$ alkyl group, a $C_{2-8}$ alkenyl group, a $C_{6-18}$ aryl group or heterocyclic group, each of which is optionally substituted is preferable. As the "$C_{6-18}$ aryl group" for $R^4$, phenyl is preferable. As the "heterocyclic group" for $R^4$, the aforementioned "5- or 6-membered aromatic monocyclic heterocyclic group" is preferable, and furyl is more preferable.

As the "optionally substituted group bonded via a carbon atom or a sulfur atom" for $R^2$, a $C_{1-8}$ alkyl group, a $C_{2-8}$ alkenyl group, a $C_{2-8}$ alkynyl group, a carbamoyl group, a $C_{1-8}$ alkyl-carbonyl group, a $C_{1-8}$ alkyl-sulfonyl group, a $C_{3-8}$ cycloalkyl group, a $C_{6-18}$ aryl group, a $C_{6-18}$ aryl-$C_{1-4}$ alkyl group, a $C_{6-18}$ aryl-carbonyl group, a $C_{6-18}$ aryl-$C_{1-4}$ alkyl-carbonyl group, a $C_{6-18}$ aryl-sulfonyl group, a heterocyclic group, a heterocyclyl-$C_{1-4}$ alkyl group, a heterocyclyl-carbonyl group or a heterocyclyl-$C_{1-4}$ alkyl-carbonyl group, each of which is optionally substituted, can be mentioned.

The "$C_{1-8}$ alkyl group", "$C_{2-8}$ alkenyl group", "$C_{2-8}$ alkynyl group", "$C_{1-8}$ alkyl-carbonyl group", "$C_{1-8}$ alkyl-sulfonyl group", "$C_{3-8}$ cycloalkyl group", "$C_{6-18}$ aryl group", "$C_{6-18}$ aryl-$C_{1-4}$ alkyl group", "$C_{6-18}$ aryl-carbonyl group", "$C_{6-18}$ aryl-$C_{1-4}$ alkyl-carbonyl group", "$C_{6-18}$ aryl-sulfonyl group", "heterocyclic group", "heterocyclyl-$C_{1-4}$ alkyl group", "heterocyclyl-carbonyl group" and "heterocyclyl-$C_{1-4}$ alkyl-carbonyl group" are optionally substituted by, for example, one or more (preferably 1 to 5, more preferably 1 to 3) substituents selected from the above-mentioned substituent group T.

As $R^2$, a hydrogen atom or a $C_{1-8}$ alkyl group, a $C_{6-18}$ aryl group, a $C_{6-18}$ aryl-$C_{1-4}$ alkyl group, a $C_{6-18}$ aryl-carbonyl group, a $C_{6-18}$ aryl-sulfonyl group or heterocyclyl-$C_{1-4}$ alkyl group, each of which is optionally substituted, is preferable. Particularly, optionally substituted $C_{1-8}$ alkyl group and the like are preferable and, for example, ethyl substituted at the 2-position and the like can be mentioned. As the substituent of the optionally substituted $C_{1-8}$ alkyl group, (g) —$(CH_2)_m$—$Z^2$—$(CH_2)_n$-Q in the above-mentioned substituent group T and the like are preferable, particularly that wherein m is 0, $Z^2$ is —$NR^8$—CO— or —O— and Q is hydroxy, namely, —O—$(CH_2)_n$—OH or —$NR^8$—CO—$(CH_2)_n$—OH(($CH_2)_n$ is optionally substituted by $C_{1-4}$ alkyl (e.g., methyl)) and the like are preferable. Particularly, —$NR^8$—CO—$(CH_2)_n$—OH (($CH_2)_n$ is optionally substituted by $C_{1-4}$ alkyl (e.g., methyl)) is preferable. In these formulas, $R^8$ is preferably a hydrogen atom and n is preferably 2. As the $(CH_2)_n$ moiety, —$CH_2$—$C(CH_3)_2$—, —$CH_2$—$CH_2$— and the like can be mentioned and —$CH_2$—$C(CH_3)_2$— and the like are preferable.

As the substituent of the optionally substituted $C_{1-8}$ alkyl group for $R^2$, (h) —$(CH_2)_m$—$Z^2$—$(CH_2)_n$—$Z^1$— (optionally halogenated $C_{1-4}$ alkyl) of the above-mentioned substituent group T and the like are preferable, particularly that wherein m is 0, $Z_2$ is —$NR^8$—CO— or —O—, and $Z_1$ is —$SO_2$—, namely, —O—$(CH_2)_n$—$SO_2$— (optionally halogenated $C_{1-4}$ alkyl) or —$NR^8$—CO—$(CH_2)_n$—$SO_2$— (optionally halogenated $C_{1-4}$ alkyl) (($CH_2)_n$ is optionally substituted by $C_{1-4}$ alkyl (e.g., methyl)) and the like are preferable. In these formulas, $R^8$ is preferably a hydrogen atom, and n is preferably 1 or 2. As the $(CH_2)_n$ moiety, —$CH_2$—, —$CH_2$—$CH_2$—, —$C(CH_3)_2$— and the like can be mentioned. As the optionally halogenated $C_{1-4}$ alkyl moiety, for example, methyl, tert-butyl and the like can be mentioned.

As the substituent of the optionally substituted $C_{1-8}$ alkyl group for $R^2$, for example, —NH—CO—$CH_2$—$C(CH_3)_2$—OH, —O—$CH_2$—$CH_2$—OH, —NH—CO—$CH_2$—$SO_2$—$CH_3$, —NH—CO—$C(CH_3)_2$—$SO_2$—$CH_3$, —O—$CH_2$—$CH_2$—$SO_2$—$C(CH_3)_3$ and the like can be mentioned, and —NH—CO—$CH_2$—$C(CH_3)_2$—OH and the like are preferable.

As the "$C_{6-18}$ aryl group" for $R^2$, phenyl is preferable. As the "$C_{6-18}$ aryl-$C_{1-4}$ alkyl group" for $R^2$, benzyl is preferable. As the "$C_{6-18}$ aryl-carbonyl group" for $R^2$, benzoyl is preferable. As the "$C_{6-18}$ aryl-sulfonyl group" for $R^2$, phenylsulfonyl is preferable. As the "heterocyclic group" or "heterocyclyl-" of "heterocyclyl-$C_{1-4}$ alkyl group", "heterocyclyl-carbonyl group" and "heterocyclyl-$C_{1-4}$ alkyl-carbonyl group" for $R^2$, the aforementioned "5- or 6-membered aromatic monocyclic heterocyclic group" or the aforementioned "aliphatic heterocyclic group" is preferable, and furyl or tetrahydrofuryl is more preferable.

In the substituents that a group represented by $R^2$ may have, when $R^6$ and $R^7$ form a ring together with a nitrogen atom, the "ring" optionally further has 1 to 5 (preferably 1 to 3) the same or different substituents. As such substituents, substituents similar to those exemplified for "aryl group" or "heterocyclic group" for B can be mentioned.

The aforementioned "carbamoyl group" and "ureido group" optionally have 1 or 2 optionally substituted $C_{1-8}$ alkyl group (s). Alternatively, the "carbamoyl group" and "ureido group" may have two substituents and they may form an optionally substituted ring, together with the adjacent nitrogen atom. As the "ring" of the "optionally substituted ring", rings similar to those formed by $R^6$ and $R^7$ together with a nitrogen atom as exemplified above can be mentioned. As the "substituent" of the "optionally substituted $C_{1-8}$ alkyl group" and as the "substituent" of the "optionally substituted ring", groups similar to the substituents of the above-mentioned substituent group T can be mentioned.

As the "optionally substituted carbamoyl group", carbamoyl, $C_{1-8}$ alkylcarbamoyl, di($C_{1-8}$ alkyl)carbamoyl, $C_{6-18}$ aryl-$C_{1-4}$ alkylcarbamoyl, azetidin-1-ylcarbonyl, pyrrolidin-1-ylcarbonyl, piperidin-1-ylcarbonyl, piperazin-1-ylcarbonyl, morpholin-4-ylcarbonyl, thiomorpholin-4-ylcarbonyl, ($C_{1-4}$ alkyl)piperidin-1-ylcarbonyl, ($C_{6-18}$ aryl-$C_{1-4}$ alkyl)piperidin-1-ylcarbonyl and the like can be mentioned.

As the "optionally substituted ureido group", ureido, 3-($C_{1-8}$ alkyl)ureido, 3,3-di($C_{1-8}$ alkyl)ureido, 3-($C_{6-18}$ aryl-$C_{1-4}$ alkyl)ureido, azetidin-1-ylcarbonylamino, pyrrolidin-1-ylcarbonylamino, piperidin-1-ylcarbonylamino, piperazin-1-ylcarbonylamino, morpholin-4-ylcarbonylamino, thiomorpholin-4-ylcarbonylamino, ($C_{1-4}$ alkyl)piperidin-1-ylcarbonylamino, ($C_{6-18}$ aryl-$C_{1-4}$ alkyl)piperidin-1-ylcarbonylamino and the like can be mentioned.

As the "ring structure" of the optionally substituted ring structure formed by $R^3$ bonded to a carbon atom or a hetero atom on the aryl group or the heteroaryl group represented by A, a saturated or unsaturated (preferably saturated) 4- to 8-membered (preferably 5- or 6-membered) nitrogen-containing heterocycle can be mentioned. Specifically,

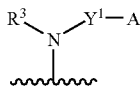

is

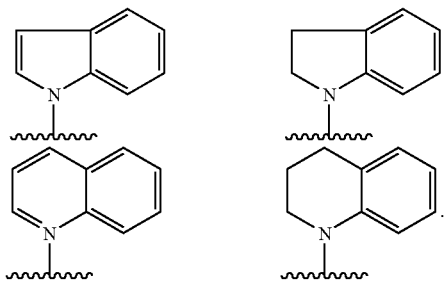

The "ring structure" may have 1 to 5 (preferably 1 to 3, more preferably 1 or 2), the same or different substituents at any substitutable position(s). As such substituents, substituents similar to those exemplified for "aryl group" or "heterocyclic group" for B can be mentioned.

As the "ring structure" of the optionally substituted ring structure formed by $R^1$ and $R^2$ bonded to each other, a saturated or unsaturated (preferably saturated) 4- to 8-membered (preferably 5- or 6-membered) heterocycle can be mentioned. When $R^1$ and $R^2$ are bonded to form an optionally substituted ring structure, for example,

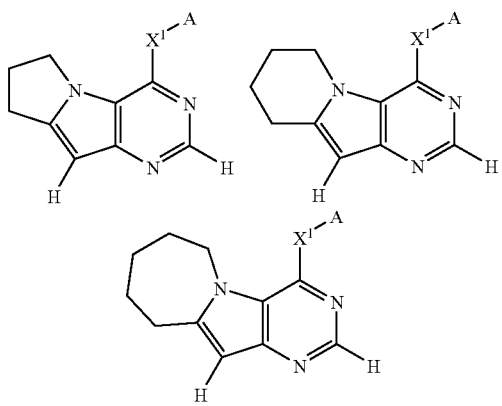

wherein each symbol is as defined above, and the like can be mentioned.

As the "ring structure" of the optionally substituted ring structure formed by $R^2$ and $R^3$ bonded to each other, a saturated or unsaturated (preferably saturated) 4- to 8-membered (preferably 5- to 7-membered) heterocycle can be mentioned. When $R^2$ and $R^3$ are bonded to form an optionally substituted ring structure, for example,

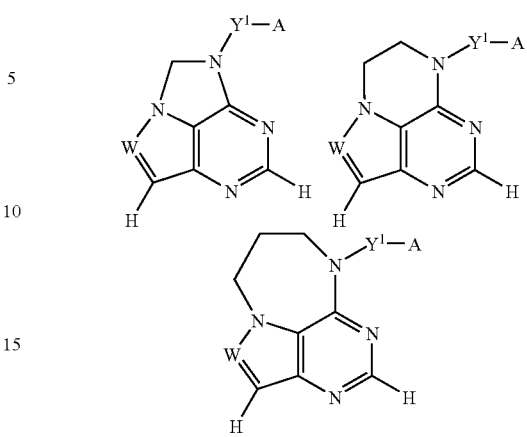

wherein each symbol is as defined above, and the like can be mentioned. The "ring structure" formed by $R^1$ and $R^2$, or $R^2$ and $R^3$ bonded to each other may have 1 to 5 (preferably 1 to 3, more preferably 1 or 2), the same or different substituents selected from the above-mentioned substituent group T at any substitutable position(s).

When W is $C(R^1)$, compound (I) is represented by the following formula (IA):

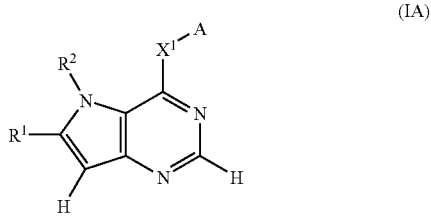

(IA)

wherein each symbol is as defined above.

When W is N, compound (I) is represented by the following formula (IB) or (IC):

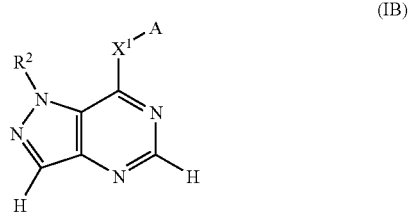

(IB)

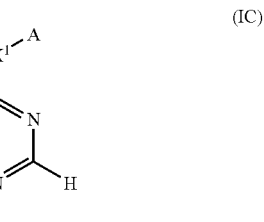

(IC)

wherein each symbol is as defined above.

Specifically, as compound (I) or a salt thereof or a prodrug thereof, the following compounds (Ia)-(Ik) or a salt thereof or a prodrug thereof and the like are preferably used.

[Compound (Ia)]

A compound represented by the formula:

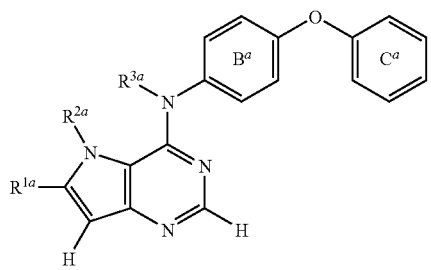

(Ia)

wherein $R^{1a}$ is a hydrogen atom or an optionally substituted group bonded via a carbon atom, a nitrogen atom or an oxygen atom, $R^{2a}$ is an optionally substituted group bonded via a carbon atom or a sulfur atom, or $R^{1a}$ and $R^{2a}$, or $R^{2a}$ and $R^{3a}$ are optionally bonded to form an optionally substituted ring structure, $R^{3a}$ is a hydrogen atom or an optionally substituted aliphatic hydrocarbon group, or $R^{3a}$ is optionally bonded to a carbon atom of the adjacent phenyl group to form an optionally substituted ring structure, $B^a$ is an optionally substituted benzene ring, and $C^a$ is an optionally substituted $C_{6-18}$ aryl group.

As the "optionally substituted group bonded via a carbon atom, a nitrogen atom or an oxygen atom" for $R^{1a}$, those similar to the "optionally substituted group bonded via a carbon atom, a nitrogen atom or an oxygen atom" for $R^1$ can be used.

As $R^{1a}$, a hydrogen atom is preferable.

As the "optionally substituted group bonded via a carbon atom or a sulfur atom" for $R^{2a}$, those similar to the "optionally substituted group bonded via a carbon atom or a sulfur atom" for $R^2$ can be used.

As the "optionally substituted ring structure" constructed by $R^{1a}$ and $R^{2a}$, or $R^{2a}$ and $R^{3a}$ bonded to each other, those similar to the "optionally substituted ring structure" constructed by $R^1$ and $R^2$, or $R^2$ and $R^3$ bonded to each other can be used.

As the "optionally substituted aliphatic hydrocarbon group" for $R^{3a}$, those similar to the "optionally substituted aliphatic hydrocarbon group" for $R^3$ can be used.

As the "optionally substituted ring structure" constructed by $R^{3a}$ bonded to a carbon atom of the adjacent phenyl group, "optionally substituted ring structure" constructed by $R^3$ bonded to a carbon atom of the adjacent phenyl group can be used.

As $R^{3a}$, a hydrogen atom is preferable.

As the substituent of the "optionally substituted benzene ring" for $B^a$, for example, 1 to 5, the same or different substituents selected from halogen, optionally halogenated $C_{1-4}$ alkyl, hydroxy, optionally halogenated $C_{1-4}$ alkyloxy, $C_{1-4}$ alkyloxymethyl, hydroxyl-$C_{1-4}$ alkyl, $C_{1-4}$ alkyl-carbonyl, carboxy, $C_{1-4}$ alkoxy-carbonyl, cyano, carbamoyl, sulfamoyl, nitro, amino, $C_{1-4}$ alkyl-carbonylamino, $C_{1-4}$ alkoxy-carbonylamino and $C_{1-4}$ alkyl-sulfonylamino are used.

As the substituent of the "optionally substituted benzene ring" for $B^a$, halogen, optionally halogenated $C_{1-4}$ alkyl and the like are preferable and, for example, chlorine, methyl and the like can be mentioned. Of these, halogen (e.g., chlorine) is preferable. As $B^a$, a benzene ring wherein the 1-position of the ring is the carbon atom bonded to N and the 3-position is substituted by chlorine or methyl (preferably chlorine) and the like can be mentioned.

As the "$C_{6-18}$ aryl group" of the "optionally substituted $C_{6-18}$ aryl group" for $C^a$, for example, phenyl, biphenylyl, naphthyl, anthryl, phenanthryl, acenaphthylenyl and the like are used. Of these, a phenyl group is preferable.

As the "substituent" of the "optionally substituted $C_{6-18}$ aryl group" for $C^a$, those similar to the "optionally substituted benzene ring" for $B^a$ can be used.

As the "substituent" of the "optionally substituted $C_{6-18}$ aryl group" for $C^a$, halogen, optionally halogenated $C_{1-4}$ alkyl, optionally halogenated $C_{1-4}$ alkyloxy and the like are preferable and, for example, chlorine, trifluoromethyl, trifluoromethoxy and the like can be mentioned. Of these, optionally halogenated $C_{1-4}$ alkyl (e.g., trifluoromethyl) and the like are preferable.

As $C^a$, for example, 3-(trifluoromethyl)phenyl, 3-(trifluoromethoxy)phenyl, 3-chlorophenyl and the like can be mentioned. Of these, 3-(trifluoromethyl)phenyl and the like are preferable.

As $R^{2a}$, a $C_{1-8}$ alkyl group, a $C_{2-8}$ alkenyl group, a $C_{2-8}$ alkynyl group, a carbamoyl group, a $C_{1-8}$ alkyl-carbonyl group, a $C_{1-8}$ alkyl-sulfonyl group, a $C_{3-8}$ cycloalkyl group, a $C_{6-18}$ aryl group, a $C_{6-18}$ aryl-$C_{1-4}$ alkyl group, a $C_{6-18}$ aryl-carbonyl group, a $C_{6-18}$ aryl-$C_{1-4}$ alkyl-carbonyl group, a $C_{6-18}$ aryl-sulfonyl group, a heterocyclic group, a heterocyclyl-$C_{1-4}$ alkyl group, a heterocyclyl-carbonyl group or a heterocyclyl-$C_{1-4}$ alkyl-carbonyl group, each optionally substituted by 1 to 5 substituents selected from the group consisting of (a) halogen, (b) oxo, (c) optionally halogenated $C_{1-4}$ alkyl, (d) —$(CH_2)_m$—Q, (e) —$(CH_2)_m$—$Z^1$— (optionally halogenated $C_{1-4}$ alkyl), (f) —$(CH_2)_m$—$Z^1$—$C_{3-8}$ cycloalkyl, (g) —$(CH_2)_m$—$Z^2$—$(CH_2)_n$-Q, (h) —$(CH_2)_m$—$Z^2$ $(CH_2)_n$—$Z^1$— (optionally halogenated $C_{1-4}$ alkyl), (i) —$(CH_2)_m$—$Z^2$—$(CH_2)_n$—$Z^1$—$C_{3-8}$ cycloalkyl, (j) —$(CH_2)_m$—$Z^1$— (optionally substituted heterocyclic group)

(preferably, 5- to 8-membered heterocyclic group having 1 to 3 hetero atoms selected from a nitrogen atom, an oxygen atom and an optionally oxidized sulfur atom), (k) —$(CH_2)_m$—$Z^2$—$C_{1-4}$ alkoxy, and (l) —$(CH_2)_m$—$Z^2$—$(CH_2)_n$—$Z^1$—$(CH_2)_n$—$Z^1$—$C_{1-4}$ alkyl wherein m is an integer of 0 to 4, n is an integer of 1 to 4, Q is hydroxy, carboxy, cyano, nitro, —$NR^6$—$R^7$, —$CONR^6R^7$, —$OCONH_2$ or —$SO_2NR^6R^7$, $Z^1$ is —O—, —CO—, —C(OH)$R^8$—, —C(=N—O$R^8$)—, —S—, —SO—, —SO$_2$—, —N(CO$R^8$)—, —N(CO$_2R^9$)—, —N(SO$_2R^9$)—, —CO—O—, —O—CO—, —CO—$NR^8$—, —$NR^8$—CO—, —$NR^8$—CO$_2$—, —$NR^8$—CO—NH—, —$NR^8$—SO$_2$— or —$NR^8$—C(=NH)—NH—, $Z^2$ is —O—, —CO—, —C(OH)R$^8$—, —C(=N—OR$^8$)—, —S—, —SO—, —SO$_2$—, —NR$^8$—, —N(COR$^8$)—, —N(CO$_2$R$^9$)—, —N(SO$_2$R$^9$)—, —CO—O—, —O—CO—, —CO—NR$^8$—, —NR$^8$—CO—, —NR$^8$—CO$_2$—, —NR$^8$—CO—NH—, —NR$^8$—C(=NH)—NH—, —NR$^8$—SO$_2$— or —SO$_2$—NR$^8$—, (CH$_2$)$_m$ and (CH$_2$)$_n$ is optionally substituted by 1 to 5 substituents selected from halogen, optionally halogenated C$_{1-4}$ alkyl and hydroxy, when m or n is not less than 2, a subset —CH$_2$CH$_2$— of (CH$_2$)$_m$ and (CH$_2$)$_n$ may be replaced by —CH=CH— or —C≡C—, R$^6$ and R$^7$ are the same or different and each is a hydrogen atom or a C$_{1-4}$ alkyl group, or R$^6$ and R$^7$ are bond to form, together with a nitrogen atom, a 3- to 8-membered saturated or unsaturated aliphatic heterocyclic group, R$^8$ is a hydrogen atom or C$_{1-4}$ alkyl and R$^9$ is C$_{1-4}$ alkyl, is preferable.

As R$^{2a}$, optionally substituted C$_{1-8}$ alkyl group and the like are preferable and, for example, ethyl substituted at the 2-position and the like can be mentioned. As the substituent of the optionally substituted C$_{1-8}$ alkyl group, (g) —(CH$_2$)$_m$—Z$^2$—(CH$_2$)$_n$-Q in the above-mentioned substituent group and the like are preferable, particularly that wherein m is 0, Z$^2$ is —NR$^8$—CO— or —O— and Q is hydroxy, namely, —O—(CH$_2$)$_n$—OH or —NR$^8$—CO—(CH$_2$)$_n$—OH((CH$_2$)$_n$ is optionally substituted by C$_{1-4}$ alkyl (e.g., methyl)) and the like are preferable. Particularly, —NR$^8$—CO—(CH$_2$)$_n$—OH ((CH$_2$)$_n$ is optionally substituted by C$_{1-4}$ alkyl (e.g., methyl)) is preferable. In these formulas, R$^8$ is preferably a hydrogen atom and n is preferably 2. As the (CH$_2$)$_n$ moiety, —CH$_2$—C(CH$_3$)$_2$—, —CH$_2$—CH$_2$— and the like can be mentioned and —CH$_2$—C(CH$_3$)$_2$— and the like are preferable.

As the substituent of the optionally substituted C$_{1-8}$ alkyl group for R$^{2a}$, (h) —(CH$_2$)$_m$—Z$^2$—(CH$_2$)$_n$—Z$^1$— (optionally halogenated C$_{1-4}$ alkyl) of the above-mentioned substituent group and the like are preferable, particularly that wherein m is 0, Z$_2$ is —NR$^8$—CO— or —O—, and Z$^1$ is —SO$_2$—, namely, —O—(CH$_2$)$_n$—SO$_2$— (optionally halogenated C$_{1-4}$ alkyl) or —NR$^8$—CO—(CH$_2$)$_n$—SO$_2$— (optionally halogenated C$_{1-4}$ alkyl) ((CH$_2$)$_n$ is optionally substituted by C$_{1-4}$ alkyl (e.g., methyl)) and the like are preferable. In these formulas, R$^8$ is preferably a hydrogen atom, and n is preferably 1 or 2. As the (CH$_2$)$_n$ moiety, —CH$_2$—, —CH$_2$—CH$_2$—, —C(CH$_3$)$_2$— and the like can be mentioned. As the optionally halogenated C$_{1-4}$ alkyl moiety, for example, methyl, tert-butyl and the like can be mentioned.

As the substituent of the optionally substituted C$_{1-8}$ alkyl group for R$^{2a}$, for example, —NH—CO—CH$_2$—C(CH$_3$)$_2$—OH, —O—CH$_2$—CH$_2$—OH, —NH—CO—CH$_2$—SO$_2$—CH$_3$, —NH—CO—C(CH$_3$)$_2$—SO$_2$—CH$_3$, —O—CH$_2$—CH$_2$—SO$_2$—C(CH$_3$)$_3$ and the like can be mentioned, and —NH—CO—CH$_2$—C(CH$_3$)$_2$—OH and the like are preferable.

As compound (Ia), a compound wherein

B$^a$ is a benzene ring optionally substituted by 1 to 4 substituents selected from halogen, C$_{1-4}$ alkyl, hydroxy-C$_{1-4}$ alkyl and C$_{1-4}$ alkyloxy;

C$^a$ is a phenyl group optionally substituted by 1 to 5 substituents selected from (i) halogen, (ii) optionally halogenated C$_{1-4}$ alkyl, (iii) hydroxy-C$_{1-4}$ alkyl, (iv) heterocyclyl-C$_{1-4}$ alkyl (preferably, 5- to 8-membered heterocyclyl-C$_{1-4}$ alkyl, said 5- to 8-membered heterocycle has 1 to 3 hetero atoms selected from a nitrogen atom, an oxygen atom and an optionally oxidized sulfur atom, such as imidazolyl, triazolyl and the like), (v) optionally halogenated C$_{1-4}$ alkyloxy, (vi) C$_{1-4}$ alkyl-carbonyl, (vii) cyano, (viii) carbamoyl optionally substituted by C$_{1-8}$ alkyl and (ix) C$_{1-4}$ alkoxy-carbonyl;

R$^{1a}$ is (i) a hydrogen atom, (ii) a cyano group, or (iii) a C$_{1-4}$ alkyl group or a C$_{2-4}$ alkenyl group, each of which is optionally substituted by —NR$^8$—CO—(CH$_2$)$_n$—NR$^6$R$^7$ wherein n is an integer of 1 to 4, R$^6$ and R$^7$ are the same or different and each is a hydrogen atom or a C$_{1-4}$ alkyl group, R$^8$ is a hydrogen atom or a C$_{1-4}$ alkyl group, and when n is not less than 2, a subset —CH$_2$CH$_2$— of (CH$_2$)$_n$ is optionally replaced by —CH=CH—;

R$^{2a}$, is a C$_{1-8}$ alkyl group, a C$_{2-8}$ alkenyl group or a C$_{2-8}$ alkynyl group, each of which is optionally substituted by substituent(s) selected from (a) hydroxy, (b) carboxy, (c) cyano, (d) optionally halogenated C$_{1-4}$ alkyloxy, (e) —O—(CH$_2$)$_n$—OH, (f) —O—(CH$_2$)$_n$—O—CO—NH$_2$, (g) —O—(CH$_2$)$_n$—O— (optionally halogenated C$_{1-4}$ alkyl), (h) —O—(CH$_2$)$_n$—SO$_2$— (optionally halogenated C$_{1-4}$ alkyl), (i) —O—(CH$_2$)$_n$—SO$_2$—C$_{6-18}$ aryl, (j) —O—(CH$_2$)$_n$—SO$_2$—(CH$_2$)$_n$—OH, (k) —O—(CH$_2$)$_n$—NR$^8$—CO—C$_{1-4}$ alkyl, (l) —O—(CH$_2$)$_n$—NR$^8$—CO—(CH$_2$)$_n$—SO$_2$—C$_{1-4}$ alkyl, (m) —O—(CH$_2$)$_n$—NR$^8$—SO$_2$— (optionally halogenated C$_{1-4}$ alkyl), (n) —CO—NR$^8$—(CH$_2$)$_n$—OH, (o) —CO—NR$^8$—(CH$_2$)$_n$—SO$_2$— (optionally halogenated C$_{1-4}$ alkyl), (p) —CO—NR$^8$—O—C$_{1-4}$ alkyl, (q) —NR$^6$R$^7$, (r) —NR$^8$—(CH$_2$)$_n$—OH, (s) —NR$^8$—(CH$_2$)$_n$—SO$_2$—C$_{1-4}$ alkyl, (t) —NR$^8$—CO— (optionally halogenated C$_{1-4}$ alkyl), (u) —NR$^8$—CO—(CH$_2$)$_n$—OH, (v) —NR$^8$—CO—(CH$_2$)$_n$—CN, (w) —NR$^8$—CO—(CH$_2$)$_n$—NR$^6$R$^7$, (x) —NR$^8$—CO—(CH$_2$)$_n$—O—C$_{1-4}$ alkyl, (y) —NR$^8$—CO—(CH$_2$)$_n$—SO— (optionally halogenated C$_{1-4}$ alkyl), (z) —NR$^8$—CO—(CH$_2$)$_n$—SO$_2$— (optionally halogenated C$_{1-4}$ alkyl), (aa) —NR$^8$—CO—(CH$_2$)$_n$—SO$_2$—C$_{3-8}$ cycloalkyl, (bb) —NR$^8$—CO—(CH$_2$)$_n$—NR$^8$—SO$_2$—C$_{1-4}$ alkyl, (cc) —NR$^8$—CO$_2$—(CH$_2$)$_n$—SO$_2$—C$_{1-4}$ alkyl, (dd) —NR$^8$—CO—NH—(CH$_2$)$_n$—SO$_2$—C$_{1-4}$ alkyl, (ee) —NR$^8$—CO—NH—O—C$_{1-4}$ alkyl, (ff) —NR$^8$—CO—NH—(CH$_2$)$_n$—O—C$_{1-4}$ alkyl, (gg) —NR$^8$—C(=NH)—NH—C$_{1-4}$ alkyl, (hh) —NR$^8$—SO$_2$—(CH$_2$)$_n$—SO$_2$—C$_{1-4}$ alkyl, (ii) —S—(CH$_2$)$_n$—OH, (jj) —SO—(CH$_2$)$_n$—OH, (kk) —SO$_2$—(CH$_2$)$_n$—OH, and (ll) —NR$^8$—CO— (optionally substituted heterocyclic group)

(preferably, said heterocyclic group is a 5- to 8-membered heterocyclic group having 1 to 3 hetero atoms selected from a nitrogen atom, an oxygen atom and an optionally oxidized sulfur atom, which is optionally substituted by substituent(s) selected from hydroxy, C$_{1-4}$ alkyl, optionally oxidized C$_{1-4}$ alkylthio, —CO—C$_{1-4}$ alkyl, —CO—O—C$_{1-4}$ alkyl, —CO—NH—C$_{1-4}$ alkyl, —CONH$_2$, —SO$_2$—C$_{1-4}$ alkyl, —SO$_2$—NH—C$_{1-4}$ alkyl, —SO$_2$NH$_2$ and the like), wherein n is an integer of 1 to 4, R$^6$ and R$^7$ are the same or different and each is a hydrogen atom or a C$_{1-4}$ alkyl group, R$^8$ is a hydrogen atom or a C$_{1-4}$ alkyl group, (CH$_2$)$_n$ is optionally substituted by optionally halogenated C$_{1-4}$ alkyl or hydroxy, and when n is not less than 2, a subset —CH$_2$CH$_2$— of (CH$_2$)$_n$ is optionally replaced by —CH=CH—; and R$^{3a}$ is a hydrogen atom or a C$_{1-6}$ alkyl group; or R$^{1a}$ and R$^{2a}$ are optionally bonded to form

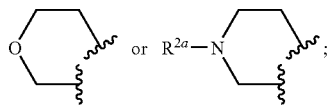

or

R$^{2a}$ and R$^{3a}$ are optionally bonded to form C$_{2-4}$ alkylene optionally substituted by an imino group is preferable.

As R$^8$, a hydrogen atom, methyl, ethyl and the like are preferable, and a hydrogen atom is particularly preferable.

As R$^{2a}$, a C$_{1-8}$ alkyl group, a C$_{2-8}$ alkenyl group or a C$_{2-8}$ alkynyl group, each of which is optionally substituted by substituent(s) selected from (a) hydroxy, (b) carboxy, (c) cyano, (d) optionally halogenated C$_{1-4}$ alkyloxy, (e) —O—(CH$_2$)$_n$—OH (wherein (CH$_2$)$_n$ is optionally substituted by hydroxy), (f) —O—(CH$_2$)$_n$—O—CO—NH$_2$, (g) —O—(CH$_2$)$_n$—O— (optionally halogenated C$_{1-4}$ alkyl), (h) —O—(CH$_2$)$_n$—SO$_2$— (optionally halogenated C$_{1-4}$ alkyl), (i) —O—(CH$_2$)$_n$—SO$_2$—C$_{6-18}$ aryl, (j) —O—(CH$_2$)$_n$—SO$_2$—(CH$_2$)$_n$—OH, (k) —O—(CH$_2$)$_n$—NR$^8$—CO—C$_{1-4}$ alkyl, (l) —O—(CH$_2$)$_n$—NR$^8$—CO—(CH$_2$)$_n$—SO$_2$—C$_{1-4}$ alkyl, (m) —O—(CH$_2$)$_n$—NR$^8$—SO$_2$— (optionally halogenated C$_{1-4}$ alkyl), (n) —CO—NR$^8$—(CH$_2$)$_n$—OH, (o) —CO—NR$^8$—(CH$_2$)$_n$—SO$_2$— (optionally halogenated C$_{1-4}$ alkyl), (p) —CO—NR$^8$—O—C$_{1-4}$ alkyl, (q) —NR$^6$R$^7$, (r) —NR$^8$—(CH$_2$)$_n$—OH, (s) —NR$^8$—(CH$_2$)$_n$—SO$_2$—C$_{1-4}$ alkyl, (t) —NR$^8$—CO— (optionally halogenated C$_{1-4}$ alkyl), (u) —NR$^8$—CO—(CH$_2$)$_n$—OH (wherein (CH$_2$)$_n$ is optionally substituted by optionally halogenated C$_{1-4}$ alkyl or hydroxy), (v) —NR$^8$—CO—(CH$_2$)$_n$—CN, (w) —NR$^8$—CO—(CH$_2$)$_n$—NR$^6$R$^7$ (when n is not less than 2, a subset —CH$_2$CH$_2$— of (CH$_2$)$_n$ is optionally replaced by —CH=CH—), (x) —NR$^8$—CO—(CH$_2$)$_n$—O—C$_{1-4}$ alkyl, (y) —NR$^8$—CO—(CH$_2$)$_n$—SO— (optionally halogenated C$_{1-4}$ alkyl), (z) —NR$^8$—CO—(CH$_2$)$_n$—SO$_2$— (optionally halogenated C$_{1-4}$ alkyl)

(wherein (CH$_2$)$_n$ is optionally substituted by C$_{1-4}$ alkyl), (aa) —NR$^8$—CO—(CH$_2$)$_n$—SO$_2$—C$_{3-8}$ cycloalkyl, (bb) —NR$^8$—CO—(CH$_2$)$_n$—NR$^8$—SO$_2$—C$_{1-4}$ alkyl, (cc) —NR$^8$—CO$_2$—(CH$_2$)$_n$—SO$_2$—C$_{1-4}$ alkyl, (dd) —NR$^8$—CO—NH—(CH$_2$)$_n$—SO$_2$—C$_{1-4}$ alkyl, (ee) —NR$^8$—CO—NH—O—C$_{1-4}$ alkyl, (ff) —NR$^8$—CO—NH—(CH$_2$)$_n$—O—C$_{1-4}$ alkyl, (gg) —NR$^8$—C(=NH)—NH—C$_{1-4}$ alkyl, (hh) —NR$^8$—SO$_2$—(CH$_2$)$_n$—SO$_2$—C$_{1-4}$ alkyl, (ii) —S—(CH$_2$)$_n$—OH, (jj) —SO—(CH$_2$)$_n$—OH, (kk) —SO$_2$—(CH$_2$)$_n$—OH, and (ll) —NR$^8$—CO— (optionally substituted heterocyclic group)

(preferably, said heterocyclic group is a 5- to 8-membered heterocyclic group having 1 to 3 hetero atoms selected from a nitrogen atom, an oxygen atom and an optionally oxidized sulfur atom, which is optionally substituted by substituent(s) selected from hydroxy, C$_{1-4}$ alkyl, optionally oxidized C$_{1-4}$ alkylthio, —CO—C$_{1-4}$ alkyl, —CO—O—C$_{1-4}$ alkyl, —CO—NH—C$_{1-4}$ alkyl, —CONH$_2$, —SO$_2$—C$_{1-4}$ alkyl, —SO$_2$—NH—C$_{1-4}$ alkyl, —SO$_2$NH$_2$ and the like), wherein n is an integer of 1 to 4, R$^6$ and R$^7$ are the same or different and each is a hydrogen atom or a C$_{1-4}$ alkyl group, and R$^8$ is a hydrogen atom or a C$_{1-4}$ alkyl group, is preferable.

As $R^8$, a hydrogen atom, methyl, ethyl and the like are preferable, and a hydrogen atom is particularly preferable.

As compound (Ia), moreover, a compound wherein $B^a$ is a benzene ring optionally substituted by 1 to 4 substituents selected from halogen and optionally halogenated $C_{1-4}$ alkyl;

$C^a$ is a phenyl group substituted by 1 to 5 substituents selected from (i) halogen, (ii) optionally halogenated $C_{1-4}$ alkyl, (iii) hydroxy-$C_{1-4}$ alkyl, (iv) heterocyclyl-$C_{1-24}$ alkyl (preferably, 5- to 8-membered heterocyclyl-$C_{1-4}$ alkyl, said 5- to 8-membered heterocycle has 1 to 3 hetero atoms selected from a nitrogen atom, an oxygen atom and an optionally oxidized sulfur atom, such as imidazolyl and the like), (v) optionally halogenated $C_{1-4}$ alkyloxy, (vi) cyano, and (vii) carbamoyl optionally substituted by $C_{1-8}$ alkyl;

$R^{1a}$ is a hydrogen atom;

$R^{2a}$ is a $C_{1-8}$ alkyl group, a $C_{2-8}$ alkenyl group or a $C_{2-8}$ alkynyl group, each of which is substituted by substituent(s) selected from (a) hydroxy, (b) optionally halogenated $C_{1-4}$ alkyloxy, (c) —O—$(CH_2)_n$—OH, (d) —O—$(CH_2)_n$—O—CO—$NH_2$, (e) —O—$(CH_2)_n$—O—$C_{1-4}$ alkyl, (f) —O—$(CH_2)_n$—$SO_2$— (optionally halogenated $C_{1-4}$ alkyl), (g) —O—$(CH_2)_n$—$SO_2$—$C_{6-18}$ aryl, (h) —O—$(CH_2)_n$—$SO_2$—$(CH_2)_n$—OH, (i) —O—$(CH_2)_n$—$NR^8$—$SO_2$— (optionally halogenated $C_{1-4}$ alkyl), (j) —CO—$NR^8$—$(CH_2)_n$—OH, (k) —CO—$NR^8$—$(CH_2)_n$—$SO_2$— (optionally halogenated $C_{1-4}$ alkyl), (l) —$NR^6R^7$, (m) —$NR^8$—$(CH_2)_n$—OH, (n) —$NR^8$—$(CH_2)_n$—$SO_2$—$C_{1-4}$ alkyl, (o) —$NR^8$—CO—$(CH_2)_n$—OH, (p) —$NR^8$—CO—$(CH_2)_n$—O—$C_{1-4}$ alkyl, (q) —$NR^8$—CO—$(CH_2)_n$—SO— (optionally halogenated $C_{1-4}$ alkyl), (r) —$NR^8$—CO—$(CH_2)_n$—$SO_2$— (optionally halogenated $C_{1-4}$ alkyl), (s) —$NR^8$—CO—$(CH_2)_n$—$SO_2$—$C_{3-8}$ cycloalkyl, (t) —$NR^8$—$CO_2$—$(CH_2)_n$—$SO_2$—$C_{1-4}$ alkyl, (u) —$NR^8$—CO—NH—$(CH_2)_n$—$SO_2$—$C_{1-4}$ alkyl, (v) —$NR^8$—$SO_2$—$(CH_2)_n$—$SO_2$—$C_{1-4}$ alkyl, (w) —S—$(CH_2)_n$—OH, (x) —SO—$(CH_2)_n$—OH, (y) —$SO_2$—$(CH_2)_n$—OH, and (z) —$NR^8$—CO— (optionally substituted heterocyclic group) (preferably, said heterocyclic group is a 5- to 8-membered heterocyclic group having 1 to 3 hetero atoms selected from a nitrogen atom, an oxygen atom and an optionally oxidized sulfur atom, which is optionally substituted by substituent(s) selected from hydroxy, $C_{1-4}$ alkyl, optionally oxidized $C_{1-4}$ alkylthio, —CO—$C_{1-4}$ alkyl, —CO—NH—$C_{1-4}$ alkyl, —$CONH_2$, —$SO_2$—$C_{1-4}$ alkyl, —$SO_2$—NH—$C_{1-4}$ alkyl, —$SO_2NH_2$ and the like), wherein n is an integer of 1 to 4, $R^6$ and $R^7$ are the same or different and each is a hydrogen atom or a $C_{1-4}$ alkyl group, $R^8$ is a hydrogen atom or a $C_{1-4}$ alkyl group, and $(CH_2)_n$ is optionally substituted by $C_{1-4}$ alkyl or hydroxy;

$R^{3a}$ is a hydrogen atom or a $C_{1-6}$ alkyl group; or $R^{1a}$ and $R^{2a}$ are optionally bonded to form

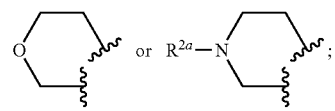

or $R^{2a}$ and $R^{3a}$ are optionally bonded to form $C_{2-4}$ alkylene, is preferable.

Of these, as $R^{2a}$, a $C_{1-8}$ alkyl group, a $C_{2-8}$ alkenyl group or a $C_{2-8}$ alkynyl group (particularly, a $C_{1-8}$-alkyl group), each of which is substituted by substituent(s) selected from (a) hydroxy, (b) optionally halogenated $C_{1-4}$ alkyloxy, (c) —O—$(CH_2)_n$—OH (wherein $(CH_2)_n$ is optionally substituted by hydroxy), (d) —O—$(CH_2)_n$—O—CO—$NH_2$, (e) —O—$(CH_2)_n$—O—$C_{1-4}$ alkyl, (f) —O—$(CH_2)_n$—$SO_2$— (optionally halogenated $C_{1-4}$ alkyl), (g) —O—$(CH_2)_n$—$SO_2$—$C_{6-18}$ aryl, (h) —O—$(CH_2)_n$—$SO_2$—$(CH_2)_n$—OH, (i) —O—$(CH_2)_n$—$NR^8$—$SO_2$— (optionally halogenated $C_{1-4}$ alkyl), (j) —CO—$NR^8$—$(CH_2)_n$—OH, (k) —CO—$NR^8$—$(CH_2)_n$—$SO_2$— (optionally halogenated $C_{1-4}$ alkyl), (l) —$NR^6R^7$, (m) —$NR^8$—$(CH_2)_n$—OH, (n) —$NR^8$—$(CH_2)_n$—$SO_2$—$C_{1-4}$ alkyl, (o) —$NR^8$—CO—$(CH_2)_n$—OH (wherein $(CH_2)_n$ is optionally substituted by $C_{1-4}$ alkyl), (p) —$NR^8$—CO—$(CH_2)_n$—O—$C_{1-4}$ alkyl, (q) —$NR^8$—CO—$(CH_2)_n$—SO— (optionally halogenated $C_{1-4}$ alkyl), (r) —$NR^8$—CO—$(CH_2)_n$—$SO_2$— (optionally halogenated $C_{1-4}$ alkyl)

(wherein $(CH_2)_n$ is optionally substituted by $C_{1-4}$ alkyl), (s) —$NR^8$—CO—$(CH_2)_n$—$SO_2$—$C_{3-8}$ cycloalkyl, (t) —$NR^8$—$CO_2$—$(CH_2)_n$—$SO_2$—$C_{1-4}$ alkyl, (u) —NR$^8$—CO—NH—(CH$_2$)$_n$—SO$_2$—C$_{1-4}$ alkyl, (v) —NR$^8$—SO$_2$—(CH$_2$)$_n$—SO$_2$—C$_{1-4}$ alkyl, (w) —S—(CH$_2$)$_n$—OH, (x) —SO—(CH$_2$)$_n$—OH, (y) —SO$_2$—(CH$_2$)N—OH, and (z) —NR$^8$—CO— (optionally substituted heterocyclic group)

(preferably, said heterocyclic group is a 5- to 8-membered heterocyclic group having 1 to 3 hetero atoms selected from a nitrogen atom, an oxygen atom and an optionally oxidized sulfur atom, which is optionally substituted by substituent(s) selected from hydroxy, C$_{1-4}$ alkyl, optionally oxidized C$_{1-4}$ alkylthio, —CO—C$_{1-4}$ alkyl, —CO—NH—C$_{1-4}$ alkyl, —CONH$_2$, —SO$_2$—C$_{1-4}$ alkyl, —SO$_2$—NH—C$_{1-4}$ alkyl, —SO$_2$NH$_2$ and the like), wherein n is an integer of 1 to 4, R$^6$ and R$^7$ are the same or different and each is a hydrogen atom or a C$_{1-4}$ alkyl group, R$^8$ is a hydrogen atom or a C$_{1-4}$ alkyl group, is preferable.

As R$^{2a}$, (i) a C$_{5-8}$ alkyl group substituted by hydroxy, (ii) a C$_{1-8}$ alkyl group substituted by substituent(s) selected from (a) halogenated C$_{1-4}$ alkyloxy, (b) —O—(CH$_2$)$_n$—OH, (c) —O—(CH$_2$)$_n$—O—CO—NH$_2$, (d) —O—(CH$_2$)$_n$—O— (optionally halogenated C$_{1-4}$ alkyl), (e) —O—(CH$_2$)$_n$—SO$_2$— (optionally halogenated C$_{1-4}$ alkyl), (f) —O—(CH$_2$)$_n$—SO$_2$—C$_{6-18}$ aryl, (g) —O—(CH$_2$)$_n$—NR$^8$—SO$_2$— (optionally halogenated C$_{1-4}$ alkyl), (h) —CO—NR$^8$—(CH$_2$)$_n$—OH, (i) —CO—NR$^8$—(CH$_2$)$_n$—SO$_2$— (optionally halogenated C$_{1-4}$ alkyl), (j) —NR$^8$—(CH$_2$)$_n$—SO$_2$—C$_{1-4}$ alkyl, (k) —NR$^8$—CO—(CH$_2$)$_n$—OH, (l) —NR$^8$—CO—(CH$_2$)$_n$—O—C$_{1-4}$ alkyl, (m) —NR$^8$—CO—(CH$_2$)$_n$—SO— (optionally halogenated C$_{1-4}$ alkyl), (n) —NR$^8$—CO—(CH$_2$)$_n$—SO$_2$— (optionally halogenated C$_{1-4}$ alkyl), (o) —NR$^8$—CO—(CH$_2$)$_n$—SO$_2$—C$_{3-8}$ cycloalkyl, (p) —NR$^8$—CO$_2$—(CH$_2$)$_n$—SO$_2$—C$_{1-4}$ alkyl, (q) —NR$^8$—CO—NH—(CH$_2$)$_n$—SO$_2$—C$_{1-4}$ alkyl, (r) —NR$^8$—SO$_2$—(CH$_2$)$_n$—SO$_2$—C$_{1-4}$ alkyl, (s) —S—(CH$_2$)$_n$—OH, (t) —SO—(CH$_2$)$_n$—OH, (u) —SO$_2$—(CH$_2$)$_n$—OH, and (v) —NR$^8$—CO— (optionally substituted heterocyclic group)

(preferably, said heterocyclic group is a 5- to 8-membered heterocyclic group having 1 to 3 hetero atoms selected from a nitrogen atom, an oxygen atom and an optionally oxidized sulfur atom, which is optionally substituted by substituent(s) selected from hydroxy, C$_{1-4}$ alkyl, optionally oxidized C$_{1-4}$ alkylthio, —CO—C$_{1-4}$ alkyl, —CO—NH—C$_{1-4}$ alkyl, —CONH$_2$, —SO$_2$—C$_{1-4}$ alkyl, —SO$_2$—NH—C$_{1-4}$ alkyl, —SO$_2$NH$_2$ and the like), wherein n is an integer of 1 to 4, R$^8$ is a hydrogen atom or a C$_{1-4}$ alkyl group, and (CH$_2$)$_n$ is optionally substituted by C$_{1-4}$ alkyl or hydroxy, (iii) a C$_{2-8}$ alkenyl group optionally substituted by hydroxy, or (iv) a C$_{2-8}$ alkynyl group optionally substituted by hydroxy is preferable, and particularly, as R$^{2a}$, (i) a C$_{5-8}$ alkyl group substituted by hydroxy, (ii) a C$_{1-8}$ alkyl group substituted by substituent(s) selected from (a) halogenated C$_{1-4}$ alkyloxy, (b) —O—(CH$_2$)$_n$—OH (wherein (CH$_2$)$_n$ is optionally substituted by hydroxy), (c) —O—(CH$_2$)$_n$—O—CO—NH$_2$, (d) —O—(CH$_2$)$_n$—O— (optionally halogenated C$_{1-4}$ alkyl), (e) —O—(CH$_2$)$_n$—SO$_2$— (optionally halogenated C$_{1-4}$ alkyl), (f) —O—(CH$_2$)$_n$—SO$_2$—C$_{6-18}$ aryl, (g) —O—(CH$_2$)$_n$—NR$^8$—SO$_2$— (optionally halogenated C$_{1-4}$ alkyl), (h) —CO—NR$^8$—(CH$_2$)$_n$—OH, (i) —CO—NR$^8$—(CH$_2$)$_n$—SO$_2$— (optionally halogenated C$_{1-4}$ alkyl), (j) —NR$^8$—(CH$_2$)$_n$—SO$_2$—C$_{1-4}$ alkyl, (k) —NR$^8$—CO—(CH$_2$)$_n$—OH (wherein (CH$_2$)$_n$ is optionally substituted by C$_{1-4}$ alkyl), (l) —NR$^8$—CO—(CH$_2$)$_n$—O—C$_{1-4}$ alkyl, (m) —NR$^8$—CO—(CH$_2$)$_n$—SO— (optionally halogenated C$_{1-4}$ alkyl), (n) —NR$^8$—CO—(CH$_2$)$_n$—SO$_2$— (optionally halogenated C$_{1-4}$ alkyl)

(wherein (CH$_2$)$_n$ is optionally substituted by C$_{1-4}$ alkyl), (o) —NR$^8$—CO—(CH$_2$)$_n$—SO$_2$—C$_{3-8}$ cycloalkyl, (p) —NR$^8$—CO$_2$—(CH$_2$)$_n$—SO$_2$—C$_{1-4}$ alkyl, (q) —NR$^8$—CO—NH—(CH$_2$)$_n$—SO$_2$—C$_{1-4}$ alkyl, (r) —NR$^8$—SO$_2$—(CH$_2$)$_n$—SO$_2$—C$_{1-4}$ alkyl, (s) —S—(CH$_2$)$_n$—OH, (t) —SO—(CH$_2$)$_n$—OH, (U) —SO$_2$—(CH$_2$)$_n$—OH, and (v) —NR$^8$—CO— (optionally substituted heterocyclic group)

(preferably, said heterocyclic group is a 5- to 8-membered heterocyclic group having 1 to 3 hetero atoms selected from a nitrogen atom, an oxygen atom and an optionally oxidized sulfur atom, which is optionally substituted by substituent(s) selected from hydroxy, C$_{1-4}$ alkyl, optionally oxidized C$_{1-4}$ alkylthio, —CO—C$_{1-4}$ alkyl, —CO—NH—C$_{1-4}$ alkyl, —CONH$_2$, —SO$_2$—C$_{1-4}$ alkyl, —SO$_2$—NH—C$_{1-4}$ alkyl, —SO$_2$NH$_2$ and the like), wherein n is an integer of 1 to 4, and R$^8$ is a hydrogen atom or a C$_{1-4}$ alkyl group, (iii) a C$_{2-8}$ alkenyl group optionally substituted by hydroxy, or (iv) a C$_{2-8}$ alkynyl group optionally substituted by hydroxy is preferable.

As R$^8$, a hydrogen atom, methyl, ethyl and the like are preferable, and a hydrogen atom is particularly preferable.

[Compound (Ib)]

A compound represented by the formula:

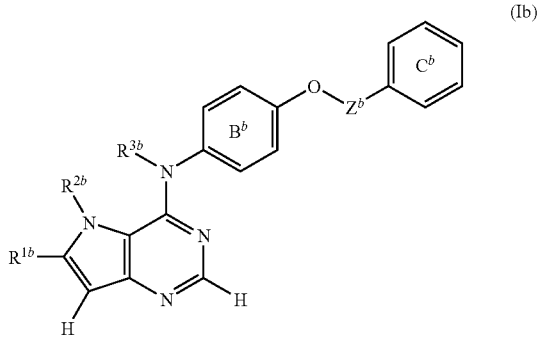

(Ib)

wherein R$^{1b}$ is a hydrogen atom or an optionally substituted group bonded via a carbon atom, a nitrogen atom or an oxygen atom, R$^{2b}$ is an optionally substituted group bonded via a carbon atom or a sulfur atom, or R$^{1b}$ and R$^{2b}$, or R$^{2b}$ and R$^{3b}$ are optionally bonded to form an optionally substituted ring structure, R$^{3b}$ is a hydrogen atom or an optionally substituted aliphatic hydrocarbon group, or R$^{3b}$ is optionally bonded to a carbon atom of the adjacent phenyl group to form an optionally substituted ring structure, B$^b$ is an optionally substituted benzene ring, C$^b$ is an optionally substituted C$_{6-18}$ aryl group, and Z$^b$ is an optionally substituted C$_{1-3}$ alkylene group.

As the "optionally substituted group bonded via a carbon atom, a nitrogen atom or an oxygen atom" for R$^{1b}$, those similar to the "optionally substituted group bonded via a carbon atom, a nitrogen atom or an oxygen atom" for R$^1$ can be used.

As R$^{1b}$, a hydrogen atom is preferable.

As the "optionally substituted group bonded via a carbon atom or a sulfur atom" for R$^{2b}$, those similar to the "optionally substituted group bonded via a carbon atom or a sulfur atom" for R$^2$ can be used.

As the "optionally substituted ring structure" formed by R$^{1b}$ and R$^{2b}$, or R$^{2b}$ and R$^{3b}$ bonded to each other, those similar to the "optionally substituted ring structure" formed by R$^1$ and R$^2$, or R$^2$ and R$^3$ bonded to each other can be used.

As the "optionally substituted aliphatic hydrocarbon group" for R$^{3b}$, those similar to the "optionally substituted aliphatic hydrocarbon group" for R$^3$ can be used.

As the "optionally substituted ring structure" formed by R$^{3b}$ and a carbon atom of the adjacent phenyl group, those similar to the "optionally substituted ring structure" formed by R$^3$ and a carbon atom of the adjacent phenyl group can be used.

As R$^{3b}$, a hydrogen atom is preferable.

As the "optionally substituted benzene ring" for B$^b$, those similar to the "optionally substituted benzene ring" for B$^a$ can be used.

As the substituent of the "optionally substituted benzene ring" for B$^b$, halogen and the like are preferable and, for example, chlorine and the like can be mentioned, and of these, halogen (e.g., chlorine) is preferable. As B$^b$, a benzene ring wherein the 1-position of the ring is the carbon atom bonded to N and the 3-position is substituted by chlorine and the like can be mentioned.

As the "optionally substituted C$_{6-18}$ aryl group" for C$^b$, those similar to the "optionally substituted C$_{6-18}$ aryl group" for C$^a$ can be used. As the "C$_{6-18}$ aryl group" of the "optionally substituted C$_{6-18}$ aryl group" for C$^b$, phenyl is preferable.

As the substituent of the "optionally substituted C$_{6-18}$ aryl group" for C$^b$, halogen and the like are preferable and, for example, fluorine and the like can be mentioned, and of these, halogen (e.g., fluorine) is preferable.

As C$^b$, for example, 3-fluorophenyl and the like can be mentioned.

As the "C$_{1-3}$ alkylene group" of the "optionally substituted C$_{1-3}$ alkylene group" for Z$^b$, methylene, ethylene, trimethylene and propylene can be used. Of these, methylene is preferable.

As the "substituent" of the "optionally substituted C$_{1-3}$ alkylene group" for Z$^b$, 1 to 3 substituents selected from halogen, hydroxy, C$_{1-4}$ alkyloxy, C$_{1-4}$ alkyl-carbonyl, carboxy, C$_{1-4}$ alkoxy-carbonyl, cyano, carbamoyl, sulfamoyl, nitro, amino, C$_{1-4}$ alkyl-carbonylamino, C$_{1-4}$ alkoxy-carbonylamino and C$_{1-4}$ alkyl-sulfonylamino can be used.

As R$^{2b}$, a C$_{1-8}$ alkyl group, a C$_{2-8}$ alkenyl group, a C$_{2-8}$ alkynyl group, a carbamoyl group, a C$_{1-8}$ alkyl-carbonyl group, a C$_{1-8}$ alkyl-sulfonyl group, a C$_{3-8}$ cycloalkyl group, a C$_{6-18}$ aryl group, a C$_{6-18}$ aryl-C$_{1-4}$ alkyl group, a C$_{6-18}$ aryl-carbonyl group, a C$_{6-18}$ aryl-C$_{1-4}$ alkyl-carbonyl group, a C$_{6-18}$ aryl-sulfonyl group, a heterocyclic group, a heterocyclyl-C$_{1-4}$ alkyl group, a heterocyclyl-carbonyl group or a heterocyclyl-C$_{1-4}$ alkyl-carbonyl group, each of which is optionally substituted by 1 to 5 substituents selected from (a) halogen, (b) oxo, (c) optionally halogenated C$_{1-4}$ alkyl, (d) —(CH$_2$)$_m$-Q, (e) —(CH$_2$)$_m$—Z$^1$— (optionally halogenated C$_{1-4}$ alkyl), (f) —(CH$_2$)$_m$—Z$^1$—C$_{3-8}$ cycloalkyl, (g) —(CH$_2$)$_m$—Z$^2$—(CH$_2$)$_n$-Q, (h) —(CH$_2$)$_m$—Z$^2$—(CH$_2$)$_n$—Z$^1$— (optionally halogenated C$_{1-4}$ alkyl), (i) —(CH$_2$)$_m$—Z$^2$—(CH$_2$)$_n$—Z$^1$—C$_{3-8}$ cycloalkyl, (j) —(CH$_2$)$_m$—Z$^1$— (optionally substituted heterocyclic group)

(preferably, said heterocyclic group is a 5- to 8-membered heterocyclic group having 1 to 3 hetero atoms selected from a nitrogen atom, an oxygen atom and an optionally oxidized sulfur atom), (k) —$(CH_2)_m$—$Z^2$—$C_{1-4}$ alkoxy, and (l) —$(CH_2)_m$—$Z^2$—$(CH_2)_n$—$Z^1$—$(CH_2)_n$—$Z^1$—$C_{1-4}$ alkyl wherein m is an integer of 0 to 4, n is an integer of 1 to 4, Q is hydroxy, carboxy, cyano, nitro, —$NR^6R^7$, —$CONR^6R^7$, —$OCONH_2$ or —$SO_2NR^6R^7$, $Z^1$ is —O—, —CO—, —C(OH)$R^8$—, —C(=N—$OR^8$)—, —S—, —SO—, —$SO_2$—, —N(COR$^8$)—, —N(CO$_2R^9$)—, —N(SO$_2R^9$)—, —CO—O—, —O—CO—, —CO—$NR^8$—, —$NR^8$—CO—, —$NR^8$—$CO_2$—, —$NR^8$—CO—NH—, —$NR^8$—$SO_2$—, or —$NR^8$—C(=NH)—NH—, $Z^2$ is —O—, —CO—, —C(OH)R—, —C(=N—OR)—, —S—, —SO—, —$SO_2$—, —$NR^8$—, —N(COR$^8$)—, —N(CO$_2R^9$)—, —N(SO$_2R^9$)—CO—O—, —O—CO—, —CO—$NR^8$—, —$NR^8$—CO—, —$NR^8$—$CO_2$—, —$NR^8$—CO—NH—, —$NR^8$—C(=NH)—NH—, —$NR^8$—$SO_2$—, or —$SO_2$—$NR^8$—, $(CH_2)_m$ and $(CH_2)_n$ are optionally substituted by 1 to 5 substituents selected from halogen, optionally halogenated $C_{1-4}$ alkyl and hydroxy, and when m or n is not less than 2, a subset —$CH_2CH_2$— of $(CH_2)_m$ and $(CH_2)_n$ is optionally replaced by —CH=CH— or —C≡C—, $R^6$ and $R^7$ are the same or different and each is a hydrogen atom or a $C_{1-4}$ alkyl group, or $R^6$ and $R^7$ are bonded to form, together with a nitrogen atom, a 3- to 8-membered saturated or unsaturated aliphatic heterocyclic group, $R^8$ is a hydrogen atom or $C_{1-4}$ alkyl, and $R^9$ is $C_{1-4}$ alkyl, is preferable.

As $R^{2b}$, optionally substituted $C_{1-8}$ alkyl group and the like are preferable and, for example, ethyl wherein the 2-position is substituted and the like can be mentioned. As the substituent of the optionally substituted $C_{1-8}$ alkyl group, (g) —$(CH_2)_m$—$Z^2$—$(CH_2)_n$-Q in the above-mentioned substituent group and the like are preferable, and particularly, that wherein m is 0, $Z^2$ is —O— and Q is hydroxy, namely, —O—$(CH_2)_n$—OH and the like are preferable. In the formula, n is preferably 2.

As the substituent of the optionally substituted $C_{1-8}$ alkyl group for $R^{2b}$, for example, —O—$CH_2$—$CH_2$—OH and the like can be mentioned.

As compound (Ib), a compound wherein $B^b$ is a benzene ring optionally substituted by halogen;

$C^b$ is a phenyl group optionally substituted by 1 to 5 substituents selected from halogen, optionally halogenated $C_{1-4}$ alkyl and cyano;

$R^{1b}$ is (i) a hydrogen atom, or (ii) a $C_{2-4}$ alkenyl group optionally substituted by hydroxy;

$R^{2b}$ is (i) a $C_{1-8}$ alkyl group optionally substituted by substituent(s) selected from (a) halogen, (b) hydroxy, (c) $C_{1-4}$ alkyloxy, (d) —O—$(CH_2)_n$—OH, (e) —O—$(CH_2)_n$—O—$C_{1-4}$ alkyl, (f) —CO—$NR^8$—$(CH_2)_n$—OH, (g) —$NR^6R^7$, and (h) —$NR^8$—$(CH_2)_n$—OH, wherein n is an integer of 1 to 4, $R^6$ and $R^7$ are the same or different and each is a hydrogen atom or a $C_{1-4}$ alkyl group, and $R^8$ is a hydrogen atom or a $C_{1-4}$ alkyl group, (ii) a $C_{6-18}$ aryl-$C_{1-4}$ alkyl group optionally substituted by substituent(s) selected from (a) $C_{1-4}$ alkyl optionally having hydroxy, (b) carboxy, (c) $C_{1-4}$ alkoxy-carbonyl, (d) 5- to 8-membered heterocyclyl-carbonyl having 1 to 3 hetero atoms selected from a nitrogen atom, an oxygen atom and a sulfur atom, which optionally has substituent(s) selected from hydroxy and $C_{1-4}$ alkyl, and (e) $C_{1-4}$ alkyl-carbamoyl optionally having substituent(s) selected from hydroxy and carbamoyl, (iii) a $C_{6-18}$ aryl-carbonyl group optionally substituted by $C_{1-4}$ alkoxy, (iv) a $C_{6-18}$ aryl-sulfonyl group optionally substituted by $C_{1-4}$ alkoxy, or (v) a 5- to 8-membered heterocyclyl-$C_{1-4}$ alkyl group having 1 to 3 hetero atoms selected from a nitrogen atom, an oxygen atom and a sulfur atom, which is optionally substituted by substituent(s) selected from (a) carboxy, and (b) $C_{1-4}$ alkoxy-carbonyl;

$R^{3b}$ is a hydrogen atom or a $C_{1-6}$ alkyl group; or $R^{2b}$ and $R^{3b}$ are optionally bonded to form $C_{2-4}$ alkylene; and $Z^b$ is a $C_{1-3}$ alkylene group, is preferable.

Moreover, as compound (Ib), a compound wherein $B^b$ is a benzene ring optionally substituted by halogen;

$C^b$ is a phenyl group optionally substituted by 1 to 5 substituents selected from halogen and optionally halogenated $C_{1-4}$ alkyl;

$R^{1b}$ is a hydrogen atom;

$R^{2b}$ is a $C_{1-8}$ alkyl group optionally substituted by substituent (s) selected from (a) hydroxy, (b) —O—$(CH_2)_n$—OH, (c) —O—$(CH_2)_n$—O—$C_{1-4}$ alkyl, (d) —CO—$NR^8$—$(CH_2)_n$—OH, (e) —$NR^6R^7$, and (f) —$NR^8$—$(CH_2)_n$—OH, wherein n is an integer of 1 to 4, $R^6$ and $R^7$ are the same or different and each is a hydrogen atom or a $C_{1-4}$ alkyl group, and $R^8$ is a hydrogen atom or a $C_{1-4}$ alkyl group;

$R^{3b}$ is a hydrogen atom or a $C_{1-6}$ alkyl group; and $Z^b$ is a $C_{1-3}$ alkylene group is preferable.

Particularly, as compound (Ib), a compound wherein $B^b$ is a benzene ring optionally substituted by halogen;

$C^b$ is a phenyl group optionally substituted by 1 to 5 substituents selected from halogen and optionally halogenated $C_{1-4}$ alkyl;

$R^{1b}$ is a hydrogen atom;

$R^{2b}$ is a $C_{1-8}$ alkyl group substituted by substituent(s) selected from (a) —O—$(CH_2)_n$—OH, (b) —O—$(CH_2)_n$—O—$C_{1-4}$ alkyl, and (c) —CO—$NR^8$—$(CH_2)_n$—OH, wherein n is an integer of 1 to 4, and $R^8$ is a hydrogen atom or a $C_{1-4}$ alkyl group;

$R^{3b}$ is a hydrogen atom or a $C_{1-6}$ alkyl group; and $Z^b$ is a methylene group is preferable.

As $R^8$, a hydrogen atom, methyl, ethyl and the like are preferable, and a hydrogen atom is particularly preferable.

[Compound (Ic)]

A compound represented by the formula:

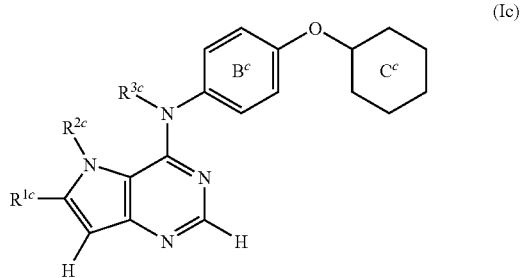

(Ic)

wherein $R^{1c}$ is a hydrogen atom or an optionally substituted group bonded via a carbon atom, a nitrogen atom or an oxygen atom, $R^{2c}$ is an optionally substituted group bonded via a carbon atom or a sulfur atom, or $R^{1c}$ and $R^{2c}$, or $R^{2c}$ and $R^{3c}$ are optionally bonded to form an optionally substituted ring structure, $R^{3c}$ is a hydrogen atom or an optionally substituted aliphatic hydrocarbon group, or $R^{3c}$ is optionally bonded to a carbon atom of the adjacent phenyl group to form an optionally substituted ring structure, $B^c$ is an optionally substituted benzene ring, and $C^c$ is an optionally substituted heterocyclic group.

As the "optionally substituted group bonded via a carbon atom, a nitrogen atom or an oxygen atom" for $R^{1c}$, those similar to the "optionally substituted group bonded via a carbon atom, a nitrogen atom or an oxygen atom" for $R^1$ can be used.

As the "optionally substituted group bonded via a carbon atom or a sulfur atom" for $R^{2c}$, those similar to the "optionally substituted group bonded via a carbon atom or a sulfur atom" for $R^2$ can be used.

As the "optionally substituted ring structure" formed by $R^{1c}$ and $R^{2c}$, or $R^{2c}$ and $R^{3c}$ bonded to each other, those similar to the "optionally substituted ring structure" formed by $R^1$ and $R^2$, or $R^2$ and $R^3$ bonded to each other can be used.

As the "optionally substituted aliphatic hydrocarbon group" for $R^{3c}$, those similar to the "optionally substituted aliphatic hydrocarbon group" for $R^3$ can be used.

As the "optionally substituted ring structure" formed by $R^{3c}$ and a carbon atom of the adjacent phenyl group, those similar to the "optionally substituted ring structure" formed by $R^3$ and a carbon atom of the adjacent phenyl group can be used.

As the "optionally substituted benzene ring" for $B^c$, those similar to the "optionally substituted benzene ring" for $B^a$ can be used.

As the "heterocyclic group" of the "optionally substituted heterocyclic group" for $C_c$, the aforementioned "heterocyclic group" can be used, and a 5- to 8-membered heterocyclic group having 1 to 3 hetero atoms selected from a nitrogen atom, an oxygen atom and an optionally oxidized sulfur atom can be particularly preferably used. Specifically, 5- or 6-membered aromatic monocyclic heterocyclic groups such as furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, triazinyl and the like, 3- to 8-membered (preferably 5- or 6-membered) saturated or unsaturated (preferably saturated) aliphatic heterocyclic groups such as oxiranyl, azetidinyl, oxetanyl, thietanyl, pyrrolidinyl, tetrahydrofuryl, thiolanyl, piperidyl, tetrahydropyranyl, morpholinyl, thiomorpholinyl, piperazinyl, dihydro-1,2,4-oxadiazolyl and the like can be used, and particularly, pyridyl, pyrimidinyl, piperidyl (particularly, 4-piperidyl) and the like are preferable.

As the "substituent" of the "optionally substituted heterocyclic group" for $C^c$, those similar to the "substituent" of the "optionally substituted $C_{6-18}$ aryl group" for $C^a$ can be used.

As $R^{2c}$, a $C_{1-8}$ alkyl group, a $C_{2-8}$ alkenyl group, a $C_{2-8}$ alkynyl group, a carbamoyl group, a $C_{1-8}$ alkyl-carbonyl group, a $C_{1-8}$ alkyl-sulfonyl group, a $C_{3-8}$ cycloalkyl group, a $C_{6-18}$ aryl group, a $C_{6-18}$ aryl-$C_{1-4}$ alkyl group, a $C_{6-18}$ aryl-carbonyl group, a $C_{6-18}$ aryl-$C_{1-4}$ alkyl-carbonyl group, a $C_{6-18}$ aryl-sulfonyl group, a heterocyclic group, a heterocyclyl-$C_{1-4}$ alkyl group, a heterocyclyl-carbonyl group or a heterocyclyl-$C_{1-4}$ alkyl-carbonyl group, each of which is optionally substituted by 1 to 5 substituents selected from the group consisting of (a) halogen, (b) oxo, (c) optionally halogenated $C_{1-4}$ alkyl, (d) —$(CH_2)_m$-Q, (e) —$(CH_2)_m$—$Z^1$— (optionally halogenated $C_{1-4}$ alkyl), (f) —$(CH_2)_m$—$Z^1$—$C_{3-8}$ cycloalkyl, (g) —$(CH_2)_m$—$Z^2$—$(CH_2)_n$-Q, (h) —$(CH_2)_m$—$Z^2$—$(CH_2)_n$—$Z^1$— (optionally halogenated $C_{1-4}$ alkyl), (i) —$(CH_2)_m$—$Z^2$—$(CH_2)_n$—$Z^1$—$C_{3-8}$ cycloalkyl, (j) —$(CH_2)_m$—$Z^1$— (optionally substituted heterocyclic group)

(preferably, said heterocyclic group is a 5- to 8-membered heterocyclic group having 1 to 3 hetero atoms selected from a nitrogen atom, an oxygen atom and an optionally oxidized sulfur atom), (k) —$(CH_2)_m$—$Z^2$—$C_{1-4}$ alkoxy, and (l) —$(CH_2)_m$—$Z^2$—$(CH_2)_n$—$Z^1$—$(CH_2)_n$—$Z^1$—$C_{1-4}$ alkyl wherein m is an integer of 0 to 4, n is an integer of 1 to 4, Q is hydroxy, carboxy, cyano, nitro, —$NR^6R^7$, —$CONR^6R^7$ or —$SO_2NR^6R^7$, $Z^1$ is —O—, —CO—, —C(OH)$R^8$—, —C(=N—OR)—, —S—, —SO—, —$SO_2$—, —N(COR$^8$)—, —N(CO$_2R^9$)—, —N(SO$_2R^9$)—, —CO—O—, —O—CO—, —CO—$NR^8$—, —$NR^8$—CO—, —$NR^8$—CO$_2$—, —$NR^8$—CO—NH—, —$NR^8$—SO$_2$—, or —$NR^8$—C(=NH)—NH—, $Z^2$ is —O—, —CO—, —C(OH)$R^8$—, —C(=N—OR$^8$)—, —S—, —SO—, —SO$_2$—, —$NR^8$—, —N(COR$^8$)—, —N(CO$_2R^9$)—, —N(SO$_2R^9$)—, —CO—O—, —O—CO—, —CO—$NR^8$—, —$NR^8$—CO—, —$NR^8$—CO$_2$—, —$NR^8$—CO—NH—, —$NR^8$—C(=NH)—NH—, —$NR^8$—SO$_2$—, or —SO$_2$—$NR^8$—, $(CH_2)_m$ and $(CH_2)_n$ are optionally substituted by 1 to 5 substituents selected from halogen, optionally halogenated $C_{1-4}$ alkyl and hydroxy, and when m or n is not less than 2, a subset —$CH_2CH_2$— of $(CH_2)_m$ and $(CH_2)_n$ is optionally replaced by —CH=CH—, $R^6$ and $R^7$ are the same or different and each is a hydrogen atom or a $C_{1-4}$ alkyl group, or $R^6$ and $R^7$ are bonded to form, together with a nitrogen atom, a 3- to 8-membered saturated or unsaturated aliphatic heterocyclic group, $R^8$ is a hydrogen atom or $C_{1-4}$ alkyl, and $R^9$ is $C_{1-4}$ alkyl, is preferable.

As compound (Ic), a compound wherein $B^c$ is a benzene ring optionally substituted by 1 to 4 substituents selected from halogen and optionally halogenated $C_{1-4}$ alkyl;

$C^c$ is a 5- to 8-membered heterocyclic group having 1 to 3 hetero atoms selected from a nitrogen atom, an oxygen atom and a sulfur atom (e.g., pyridyl, pyrimidyl, 4-piperidyl), which is optionally substituted by 1 to 5 substituents selected from (i) halogen, (ii) $C_{1-4}$ alkyl, (iii) $C_{1-4}$ alkyl-carbonyl, (iv) optionally halogenated $C_{1-4}$ alkoxy-carbonyl, (v) $C_{3-8}$ cycloalkyl-carbonyl, and (vi) a carbamoyl group optionally substituted by substituent(s) selected from (a) optionally halogenated $C_{1-8}$ alkyl, (b) $C_{3-8}$ cycloalkyl, and (c) $C_{6-18}$ aryl optionally substituted by substituent(s) selected from halogen, $C_{1-4}$ alkyl and $C_{1-4}$ alkyloxy;

$R^{1c}$ is (i) a hydrogen atom, (ii) a $C_{2-4}$ alkenyl group optionally substituted by hydroxy, or (iii) a 5- to 8-membered heterocyclic group having 1 to 3 hetero atoms selected from a nitrogen atom, an oxygen atom and a sulfur atom;

$R^{2c}$ is (i) a $C_{1-4}$ alkyl group optionally substituted by substituent(s) selected from (a) halogen, (b) hydroxy, (c) $C_{1-4}$ alkyloxy, (d) carboxy, (e) $C_{1-4}$ alkoxy-carbonyl, (f) —O—$(CH_2)_n$—OH, (g) —O—$(CH_2)_n$—O—$C_{1-4}$ alkyl, (h) —CO—$NR^8$—$(CH_2)_n$—OH, and (i) —$NR^8$—CO—$(CH_2)_n$—SO$_2$—$C_{1-4}$ alkyl wherein n is an integer of 1 to 4, and $R^8$ is a hydrogen atom or a $C_{1-4}$ alkyl group, or (ii) a $C_{6-18}$ aryl-$C_{1-4}$ alkyl group optionally substituted by $C_{1-4}$ alkyl optionally having hydroxy; and $R^{3c}$ is a hydrogen atom or a $C_{1-6}$ alkyl group; or $R^{2c}$ and $R^{3c}$ are optionally bonded to form $C_{2-4}$ alkylene, is preferable.

Moreover, as compound (Ic), a compound wherein $B^c$ is a benzene ring optionally substituted by 1 to 4 substituents selected from halogen and $C_{1-4}$ alkyl;

$C^c$ is a 5- to 8-membered heterocyclic group having 1 to 3 hetero atoms selected from a nitrogen atom, an oxygen atom and a sulfur atom, which is optionally substituted by 1 to 5 substituents selected from (i) $C_{1-4}$ alkyl, (ii) $C_{1-4}$ alkyl-carbonyl, (iii) optionally halogenated $C_{1-4}$ alkoxy-carbonyl, (iv) $C_{3-8}$ cycloalkyl-carbonyl, and (v) a carbamoyl group optionally substituted by substituent(s) selected from (a) optionally halogenated $C_{1-8}$ alkyl, (b) $C_{3-8}$ cycloalkyl, and (c) $C_{6-18}$ aryl optionally substituted by halogen;

$R^{1c}$ is a hydrogen atom;

$R^{2c}$ is a $C_{1-4}$ alkyl group optionally substituted by substituent(s) selected from (a) hydroxy, (b) $C_{1-4}$ alkyloxy, (c) —O—$(CH_2)_n$—OH, (d) —O—$(CH_2)_n$—O—$C_{1-4}$ alkyl, and (e) —$NR^8$—CO—$(CH_2)_n$—SO$_2$—$C_{1-4}$ alkyl wherein n is an integer of 1 to 4, and $R^8$ is a hydrogen atom or a $C_{1-4}$ alkyl group; and $R^{3c}$ is a hydrogen atom or a $C_{1-6}$ alkyl group, is preferable, particularly, a compound wherein $R^{2c}$ is a $C_{1-4}$ alkyl group optionally substituted by substituent(s) selected from (a) —O—(CH$_2$)$_n$—OH, and (b) —O—(CH$_2$)$_n$—O—C$_{1-4}$ alkyl, wherein n is an integer of 1 to 4, is preferable.

[Compound (Id)]

A compound represented by the formula

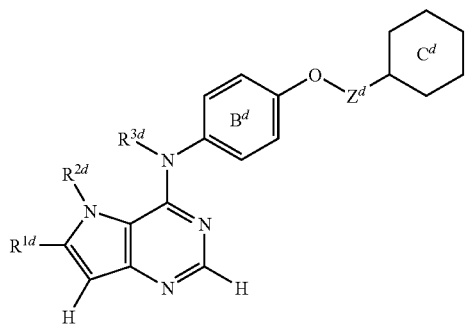

(Id)

wherein R$^{1d}$ is a hydrogen atom or an optionally substituted group bonded via a carbon atom, a nitrogen atom or an oxygen atom, R$^{2d}$ is an optionally substituted group bonded via a carbon atom or a sulfur atom, or R$^{1d}$ and R$^{2d}$, or R$^{2d}$ and R$^{3d}$ are optionally bonded to form an optionally substituted ring structure, R$^{3d}$ is a hydrogen atom or an optionally substituted aliphatic hydrocarbon group, or R$^{3d}$ is optionally bonded to a carbon atom of the adjacent phenyl group to form an optionally substituted ring structure, B$^d$ is an optionally substituted benzene ring, C$^d$ is an optionally substituted heterocyclic group, and Z$^d$ is an optionally substituted C$_{1-3}$ alkylene group.

As the "optionally substituted group bonded via a carbon atom, a nitrogen atom or an oxygen atom" for R$^{1d}$, those similar to the "optionally substituted group bonded via a carbon atom, a nitrogen atom or an oxygen atom" for R$^1$ can be used.

As the "optionally substituted group bonded via a carbon atom or a sulfur atom" for R$^{2d}$, those similar to the "optionally substituted group bonded via a carbon atom or a sulfur atom" for R$^2$ can be used.

As the "optionally substituted ring structure" formed by R$^{1d}$ and R$^{2d}$, or R$^{2d}$ and R$^{3d}$ bonded to each other, those similar to the "optionally substituted ring structure" formed by R$^1$ and R$^2$, or R$^2$ and R$^3$ bonded to each other can be used.

As the "optionally substituted aliphatic hydrocarbon group" for R$^{3d}$, those similar to the "optionally substituted aliphatic hydrocarbon group" for R$^3$ can be used.

As the "optionally substituted ring structure" formed by R$^{3d}$ and a carbon atom of the adjacent phenyl group, those similar to the "optionally substituted ring structure" formed by R$^3$ and a carbon atom of the adjacent phenyl group can be used.

As the "optionally substituted benzene ring" for B$^d$, those similar to the "optionally substituted benzene ring" for B$^a$ can be used.

As the "optionally substituted heterocyclic group" for C$^d$, those similar to the "optionally substituted heterocyclic group" for cc can be used.

As the "optionally substituted C$_{1-3}$ alkylene ring" for Z$^d$, those similar to the "optionally substituted C$_{1-3}$ alkylene ring" for Z$^b$ can be used.

As R$^{2d}$, a C$_{1-8}$ alkyl group, a C$_{2-8}$ alkenyl group, a C$_{2-8}$ alkynyl group, a carbamoyl group, a C$_{1-8}$ alkyl-carbonyl group, a C$_{1-8}$ alkyl-sulfonyl group, a C$_{3-8}$ cycloalkyl group, a C$_{6-18}$ aryl group, a C$_{6-18}$ aryl-C$_{1-4}$ alkyl group, a C$_{6-18}$ aryl-carbonyl group, a C$_{6-18}$ aryl-C$_{1-4}$ alkyl-carbonyl group, a C$_{6-18}$ aryl-sulfonyl group, a heterocyclic group, a heterocyclyl-C$_{1-4}$ alkyl group, a heterocyclyl-carbonyl group or a heterocyclyl-C$_{1-4}$ alkyl-carbonyl group, each of which is optionally substituted by 1 to 5 substituents selected from (a) halogen, (b) oxo, (c) optionally halogenated C$_{1-4}$ alkyl, (d) —(CH$_2$)$_m$-Q, (e) —(CH$_2$)$_m$—Z$^1$— (optionally halogenated C$_{1-4}$ alkyl), (f) —(CH$_2$)$_m$—Z$^1$—C$_{3-8}$ cycloalkyl, (g) —(CH$_2$)$_m$—Z$^2$—(CH$_2$)$_n$-Q, (h) —(CH$_2$)$_m$—Z$^2$—(CH$_2$)$_n$—Z$^1$— (optionally halogenated C$_{1-4}$ alkyl), (i) —(CH$_2$)$_m$—Z$^2$—(CH$_2$)$_n$—Z$^1$—C$_{3-8}$ cycloalkyl, (j) —(CH$_2$)$_m$—Z$^1$— (optionally substituted heterocyclic group)

(preferably, said heterocyclic group is a 5- to 8-membered heterocyclic group having 1 to 3 hetero atoms selected from a nitrogen atom, an oxygen atom and an optionally oxidized sulfur atom), (k) —(CH$_2$)$_m$—Z$^2$—C$_{1-4}$ alkoxy, and (l) —(CH$_2$)$_m$—Z$^2$—(CH$_2$)$_n$—Z$^1$—(CH$_2$)$_n$—Z$^1$—C$_{1-4}$ alkyl wherein m is an integer of 0 to 4, n is an integer of 1 to 4, Q is hydroxy, carboxy, cyano, nitro, —NR$^6$R$^7$, —CONR$^6$R$^7$ or —SO$_2$NR$^6$R$^7$, Z$^1$ is —O—, —CO—, —C(OH)R$^8$—, —C(=N—OR$^8$)—, —S—, —SO—, —SO$_2$—, —N(COR$^8$)—, —N(CO$_2$R$^9$)—, —N(SO$_2$R$^9$)—, —CO—O—, —O—CO—, —CO—NR$^8$—, —NR$^8$—CO—, —NR$^8$—CO$_2$—, —NR$^8$—CO—NH—, —NR$^8$—SO$_2$—, or —NR$^8$—C(=NH)—NH—, Z$^2$ is —O—, —CO—, —C(OH)R$^8$—, —C(=N—OR$^8$)—, —S—, —SO—, —SO$_2$—, —NR$^8$—, —N(COR$^8$)—, —N(CO$_2$R$^9$)—, —N(SO$_2$R$^9$)—, —CO—O—, —O—CO—, —CO—NR$^8$—, —NR$^8$—CO—, —NR$^8$—CO$_2$—, —NR$^8$—CO—NH—, —NR$^8$—C(=NH)—NH—, —NR$^8$—SO$_2$—, or —SO$_2$—NR$^8$—, (CH$_2$)$_m$ and (CH$_2$)$_n$ are optionally substituted by 1 to 5 substituents selected from halogen, optionally halogenated C$_{1-4}$ alkyl and hydroxy, and when m or n is not less than 2, a subset —CH$_2$CH$_2$— of (CH$_2$)$_m$ and (CH$_2$)$_n$ is optionally replaced by —CH=CH—, R$^6$ and R$^7$ are the same or different and each is a hydrogen atom, or a C$_{1-4}$ alkyl group, or R$^6$ and R$^7$ are bonded to form, together with a nitrogen atom, a 3- to 8-membered saturated or unsaturated aliphatic heterocyclic group, R$^8$ is a hydrogen atom or C$_{1-4}$ alkyl, and R$^9$ is C$_{1-4}$ alkyl, is preferable.

As compound (Id), a compound wherein $B^d$ is a benzene ring optionally substituted by halogen;

$C^d$ is a 5- to 8-membered heterocyclic group having 1 to 3 hetero atoms selected from a nitrogen atom, an oxygen atom and a sulfur atom;

$R^{1d}$ is a hydrogen atom;

$R^{2d}$ is (i) $C_{1-4}$ alkyl optionally substituted by substituent(s) selected from (a) $C_{1-4}$ alkyloxy (b) —O—$(CH_2)_n$—OH, and (c) —$NR^8$—CO—$(CH_2)_n$—$SO_2$—$C_{1-4}$ alkyl wherein n is an integer of 1 to 4, and $R^8$ is a hydrogen atom or a $C_{1-4}$ alkyl group, or (ii) a 5- to 8-membered heterocyclyl-$C_{1-4}$ alkyl group having 1 to 3 hetero atoms selected from a nitrogen atom, an oxygen atom and a sulfur atom, which is optionally substituted by substituent(s) selected from (a) carboxy, and (b) $C_{1-4}$ alkoxy-carbonyl;

$R^{3d}$ is a hydrogen atom or a $C_{1-6}$ alkyl group; and $Z^d$ is a $C_{1-3}$ alkylene group, is preferable.

Moreover, as compound (Id), a compound wherein $B^d$ is a benzene ring optionally substituted by halogen;

$C^d$ is a 5- to 8-membered heterocyclic group having 1 to 3 hetero atoms selected from a nitrogen atom, an oxygen atom and a sulfur atom;

$R^{1d}$ is a hydrogen atom, $R^{2d}$ is a $C_{1-4}$ alkyl group optionally substituted by $C_{1-4}$ alkyloxy, $R^{3d}$ is a hydrogen atom or a $C_{1-6}$ alkyl group; and $Z^d$ is a methylene group, is preferable.

[Compound (Ie)]

A compound represented by the formula:

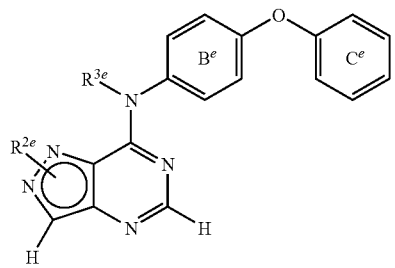

(Ie)

wherein $R^{2e}$ is an optionally substituted group bonded via a carbon atom or a sulfur atom, or $R^{2e}$ and $R^{3e}$ are optionally bonded to form an optionally substituted ring structure, $R^{3e}$ is a hydrogen atom or an optionally substituted aliphatic hydrocarbon group, or $R^{3e}$ is optionally bonded to a carbon atom of the adjacent phenyl group to form an optionally substituted ring structure, $B^e$ is an optionally substituted benzene ring, and $C^e$ is an optionally substituted $C_{6-18}$ aryl group.

As the "optionally substituted group bonded via a carbon atom or a sulfur atom" for $R^{2e}$, those similar to the "optionally substituted group bonded via a carbon atom or a sulfur atom" for $R^2$ can be used.

As the "optionally substituted ring structure" formed by $R^{2e}$ and $R^{3e}$ bonded to each other, those similar to the "optionally substituted ring structure" formed by $R^2$ and $R^3$ bonded to each other can be used.

As the "optionally substituted aliphatic hydrocarbon group" for $R^{3e}$, those similar to the "optionally substituted aliphatic hydrocarbon group" for $R^3$ can be used.

As the "optionally substituted ring structure" formed by $R^{3e}$ and a carbon atom of the adjacent phenyl group, those similar to the "optionally substituted ring structure" formed by $R^3$ and a carbon atom of the adjacent phenyl group can be used.

As the "optionally substituted benzene ring" for $B^e$, those similar to the "optionally substituted benzene ring" for $B^a$ can be used.

As the "optionally substituted $C_{6-18}$ aryl group" for $C^e$, those similar to the "optionally substituted $C_{6-18}$ aryl group" for $C^a$ can be used.

As $R^{2e}$, a $C_{1-8}$ alkyl group, a $C_{2-8}$ alkenyl group, a $C_{2-8}$ alkynyl group, a carbamoyl group, a $C_{1-8}$ alkyl-carbonyl group, a $C_{1-8}$ alkyl-sulfonyl group, a $C_{3-8}$ cycloalkyl group, a $C_{6-18}$ aryl group, a $C_{6-18}$ aryl-$C_{1-4}$ alkyl group, a $C_{6-18}$ aryl-carbonyl group, a $C_{6-18}$ aryl-$C_{1-4}$ alkyl-carbonyl group, a $C_{6-18}$ aryl-sulfonyl group, a heterocyclic group, a heterocyclyl-$C_{1-4}$ alkyl group, a heterocyclyl-carbonyl group or a heterocyclyl-$C_{1-4}$ alkyl-carbonyl group, each of which is optionally substituted by 1 to 5 substituents selected from (a) halogen, (b) oxo, (c) optionally halogenated $C_{1-4}$ alkyl, (d) —$(CH_2)_m$-Q, (e) —$(CH_2)_m$—$Z^1$— (optionally halogenated $C_{1-4}$ alkyl), (f) —$(CH_2)_m$—$Z^1$—$C_{3-8}$ cycloalkyl, (g) —$(CH_2)_m$—$Z^2$—$(CH_2)_n$-Q, (h) —$(CH_2)_m$—$Z^2$—$(CH_2)_n$—$Z^1$— optionally halogenated $C_{1-4}$ alkyl, (i) —$(CH_2)_m$—$Z^2$—$(CH_2)_n$—$Z^1$—$C_{3-8}$ cycloalkyl, (j) —$(CH_2)_m$—$Z^1$— (optionally substituted heterocyclic group)

(preferably, said heterocyclic group is a 5- to 8-membered heterocyclic group having 1 to 3 hetero atoms selected from a nitrogen atom, an oxygen atom and an optionally oxidized sulfur atom), (k) —$(CH_2)_m$—$Z^2$—$C_{1-4}$ alkoxy, and (l) —$(CH_2)_m$—$Z^2$—$(CH_2)_n$—$Z^1$—$(CH_2)_n$—$Z^1$—$C_{1-4}$ alkyl wherein m is an integer of 0 to 4, n is an integer of 1 to 4, Q is hydroxy, carboxy, cyano, nitro, —$NR^5R^7$, —$CONR^6R^7$ or —$SO_2NR^6R^7$, $Z^1$ is —O—, —CO—, —C(OH)$R^8$—, —C(=N—O$R^8$)—, —S—, —SO—, —SO$_2$—, —N(CO$R^8$)—, —N(CO$_2R^9$)—, —N(SO$_2R^9$)—, —CO—O—, —O—CO—, —CO—N$R^8$—, —N$R^8$—CO—, —N$R^8$—CO$_2$—, —N$R^8$—CO—NH—, —N$R^8$—SO$_2$—, or —N$R^8$—C(=NH)—NH—, $Z^2$ is —O—, —CO—, —C(OH)$R^8$—, —C(=N—O$R^8$)—, —S—, —SO—, —SO$_2$—, —N$R^8$—, —N(CO$R^8$)—, —N(CO$_2R^9$)—, —N(SO$_2R^9$)—, —CO—O—, —O—CO—, —CO—N$R^8$—, —N$R^8$—CO—, —N$R^8$—CO$_2$—, —N$R^8$—CO—NH—, —N$R^8$—C(=NH)—NH—, —N$R^8$—SO$_2$—, or —SO$_2$—N$R^8$—, $(CH_2)_m$ and $(CH_2)_n$ are optionally substituted by 1 to 5 substituents selected from halogen, optionally halogenated $C_{1-4}$ alkyl and hydroxy, and when m or n is not less than 2, a subset —CH$_2$CH$_2$— of $(CH_2)_m$ and $(CH_2)_n$ is optionally replaced by —CH=CH—, $R^6$ and $R^7$ are the same or different and each is a hydrogen atom or a $C_{1-4}$ alkyl group, or $R^6$ and $R^7$ are bonded to form, together with a nitrogen atom, a 3- to 8-membered saturated or unsaturated aliphatic heterocyclic group, $R^8$ is a hydrogen atom or $C_{1-4}$ alkyl, and $R^9$ is $C_{1-4}$ alkyl, is preferable.

As compound (Ie), a compound wherein $B^e$ is a benzene ring optionally substituted by halogen;

$C^e$ is a phenyl group optionally substituted by optionally halogenated $C_{1-4}$ alkyl; and $R^{2e}$ is a $C_{1-4}$ alkyl group optionally substituted by —O—$(CH_2)_n$—OH wherein n is an integer of 1 to 4, is preferable.

Moreover, as compound (Ie), a compound wherein $B^e$ is a benzene ring optionally substituted by halogen;

$C^e$ is a phenyl group optionally substituted by optionally halogenated $C_{1-4}$ alkyl; and $R^{2e}$ is a $C_{1-4}$ alkyl group substituted by —O—$(CH_2)_n$—OH wherein n is an integer of 1 to 4, is preferable.

[Compound (If)]

A compound represented by the formula:

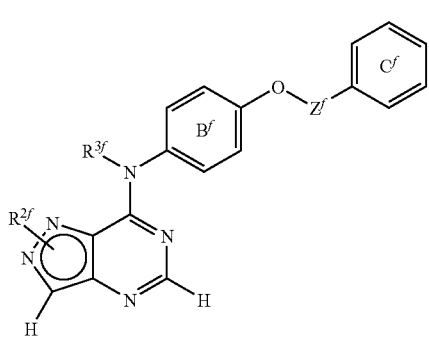

(If)

wherein $R^{2f}$ is an optionally substituted group bonded via a carbon atom or a sulfur atom, or $R^{2f}$ and $R^{3f}$ are optionally bonded to form an optionally substituted ring structure, $R^{3f}$ is a hydrogen atom or an optionally substituted aliphatic hydrocarbon group, or $R^{3f}$ is optionally bonded to a carbon atom of the adjacent phenyl group to form an optionally substituted ring structure, $B^f$ is an optionally substituted benzene ring, $C^f$ is an optionally substituted $C_{6-18}$ aryl group, and $Z^f$ is an optionally substituted $C_{1-3}$ alkylene group.

As the "optionally substituted group bonded via a carbon atom or a sulfur atom" for $R^{2f}$, those similar to the "optionally substituted group bonded via a carbon atom or a sulfur atom" for $R^2$ can be used.

As the "optionally substituted ring structure" formed by $R^{2f}$ and $R^{3f}$ bonded to each other, those similar to the "optionally substituted ring structure" formed by $R^2$ and $R^3$ bonded to each other can be used.

As the "optionally substituted aliphatic hydrocarbon group" for $R^{3f}$, those similar to the "optionally substituted aliphatic hydrocarbon group" for $R^3$ can be used.

As the "optionally substituted ring structure" formed by $R^{3f}$ and a carbon atom of the adjacent phenyl group, those similar to the "optionally substituted ring structure" formed by $R^3$ and a carbon atom of the adjacent phenyl group can be used.

As the "optionally substituted benzene ring" for $B^f$, those similar to the "optionally substituted benzene ring" for $B^a$ can be used.

As the "optionally substituted $C_{6-18}$ aryl group" for $C^f$, those similar to the "optionally substituted $C_{6-18}$ aryl group" for $C^a$ can be used.

As the "optionally substituted $C_{1-3}$ alkylene group" for $Z^f$, those similar to the "optionally substituted $C_{1-3}$ alkylene group" for $Z^b$ can be used.

As $R^{2f}$, a $C_{1-8}$ alkyl group, a $C_{2-8}$ alkenyl group, a $C_{2-8}$ alkynyl group, a carbamoyl group, a $C_{1-6}$ alkyl-carbonyl group, a $C_{1-8}$ alkyl-sulfonyl group, a $C_{3-8}$ cycloalkyl group, a $C_{6-18}$ aryl group, a $C_{6-18}$ aryl-$C_{1-4}$ alkyl group, a $C_{6-18}$ aryl-carbonyl group, a $C_{6-18}$ aryl-$C_{1-4}$ alkyl-carbonyl group, a $C_{6-18}$ aryl-sulfonyl group, a heterocyclic group, a heterocyclyl-$C_{1-4}$ alkyl group, a heterocyclyl-carbonyl group or a heterocyclyl-$C_{1-4}$ alkyl-carbonyl group, each of which is optionally substituted by 1 to 5 substituents selected from (a) halogen, (b) oxo, (c) optionally halogenated $C_{1-4}$ alkyl, (d) —$(CH_2)_m$-Q, (e) —$(CH_2)_m$—$Z^1$— (optionally halogenated $C_{1-4}$ alkyl), (f) —$(CH_2)_m$—$Z^1$—$C_{3-8}$ cycloalkyl, (g) —$(CH_2)_m$—$Z^2$—$(CH_2)_n$-Q, (h) —$(CH_2)_m$—$Z^2$—$(CH_2)_n$—$Z^1$— (optionally halogenated $C_{1-4}$ alkyl), (i) —$(CH_2)_m$—$Z_2$—$(CH_2)_n$—$Z^1$—$C_{3-8}$ cycloalkyl, (j) —$(CH_2)_m$—$Z^1$— (optionally substituted heterocyclic group)

(preferably, said heterocyclic group is a 5- to 8-membered heterocyclic group having 1 to 3 hetero atoms selected from a nitrogen atom, an oxygen atom and an optionally oxidized sulfur atom), (k) —$(CH_2)_m$—$Z^2$—$C_{1-4}$ alkoxy, and (l) —$(CH_2)_m$—$Z^2$ $(CH_2)_n$—$Z^1$—$(CH_2)_n$—$Z^1$—$C_{1-4}$ alkyl wherein m is an integer of 0 to 4, n is an integer of 1 to 4, Q is hydroxy, carboxy, cyano, nitro, —N$R^6R^7$, —CON$R^6R^7$ or —SO$_2$N$R^6R^7$, $Z^1$ is —O—, —CO—, C(OH)$R^8$—, C(=N—O$R^8$)—, —S—, —SO—, —SO$_2$—, —N(CO$R^8$)—, —N(CO$_2R^9$)—, —N(SO$_2R^9$)—, —CO—O—, —O—CO—, —CO—N$R^8$—, —N$R^8$—CO—, —N$R^8$—CO$_2$—, —N$R^8$—CO—NH—, —N$R^8$—SO$_2$—, or —N$R^8$—C(=NH)—NH—, $Z^2$ is —O—, —CO—, C(OH)$R^8$—, —C(=N—O$R^8$)—, —S—, —SO—, —SO$_2$—, —N$R^8$—, —N(CO$R^8$)—, —N(CO$_2R^9$)—, —N(SO$_2R^9$)—, —CO—O—, —O—CO—, —CO—N$R^8$—, —N$R^8$—CO—, —N$R^8$—CO$_2$—, —N$R^8$—CO—NH—, —N$R^8$—C(=NH)—NH—, —N$R^8$—SO$_2$—, or —SO$_2$—N$R^8$—, (CH$_2$)$_m$ and (CH$_2$)$_n$ are optionally substituted by 1 to 5 substituents selected from halogen, optionally halogenated $C_{1-4}$ alkyl and hydroxy, and when m or n is not less than 2, a subset —CH$_2$CH$_2$— of (CH$_2$)$_m$ and (CH$_2$)$_n$ is optionally replaced by —CH=CH—, $R^6$ and $R^7$ are the same or different and each is a hydrogen atom or a $C_{1-4}$ alkyl group, or $R^6$ and $R^7$ are bonded to form, together with a nitrogen atom, a 3- to 8-membered saturated or unsaturated aliphatic heterocyclic group, $R^e$ is a hydrogen atom or $C_{1-4}$ alkyl, and $R^9$ is $C_{1-4}$ alkyl, is preferable.

As compound (If), a compound wherein $B^f$ is a benzene ring optionally substituted by halogen;

$C^f$ is a phenyl group optionally substituted by halogen;

$R^{2f}$ is (i) a $C_{1-4}$ alkyl group optionally substituted by 1 to 5 substituents selected from the group consisting of (a) hydroxy, (b) —O—(CH$_2$)$_n$—OH, (c) —N$R^8$—(CH$_2$)$_n$—O—$C_{1-4}$ alkyl, (d) —N$R^8$—(CH$_2$)$_n$-heterocyclic group (preferably, said heterocyclic group is a 5- to 8-membered heterocyclic group having 1 to 3 hetero atoms selected from a nitrogen atom, an oxygen atom and a sulfur atom), and (e) —N$R^8$—(CH$_2$)$_n$—SO$_2$—$C_{1-4}$ alkyl, wherein n is an integer of 1 to 4, and $R^8$ is a hydrogen atom or a $C_{1-4}$ alkyl group, (ii) a $C_{6-18}$ aryl group optionally substituted by 1 to 5 substituents selected from the group consisting of (a) $C_{1-4}$ alkyl optionally substituted by substituent(s) selected from hydroxy, —N$R^8$—(CH$_2$)$_n$—OH, —N$R^8$—(CH$_2$)$_n$—O—$C_{1-4}$ alkyl, —N$R^8$—(CH$_2$)$_n$-heterocyclic group (preferably, said heterocyclic group is a 5- to 8-membered heterocyclic group having 1 to 3 hetero atoms selected from a nitrogen atom, an oxygen atom and a sulfur atom) and —N$R^8$—(CH$_2$)$_n$—SO$_2$—$C_{1-4}$ alkyl, and (b) —CO—N$R^8$—(CH$_2$)$_n$—O—$C_{1-4}$ alkyl, wherein n is an integer of 1 to 4, and $R^8$ is a hydrogen atom or a $C_{1-4}$ alkyl group, or (iii) a $C_{6-18}$ aryl-$C_{1-4}$ alkyl group optionally substituted by 1 to 5 substituents selected from the group consisting of (a) carboxy, (b) $C_{1-4}$ alkoxy-carbonyl, and (c) —CO—N$R^8$—(CH$_2$)$_n$—O—$C_{1-4}$ alkyl, wherein n is an integer of 1 to 4, and $R^8$ is a hydrogen atom or a $C_{1-4}$ alkyl group, $R^{3f}$ is a hydrogen atom or a $C_{1-6}$ alkyl group; and $Z^f$ is a $C_{1-3}$ alkylene group; or $R^{2f}$ and $R^{3f}$ are optionally bonded to form $C_{2-4}$ alkylene, is preferable.

As $R^8$, a hydrogen atom, methyl, ethyl and the like are preferably, and a hydrogen atom is particularly preferable.

Moreover, as compound (If), a compound wherein $B^f$ is a benzene ring optionally substituted by halogen;

$C^f$ is a phenyl group optionally substituted by halogen;

$R^{2f}$ is a $C_{1-4}$ alkyl group optionally substituted by 1 to 5 substituents selected from the group consisting of (a) hydroxy, and (b) —O—(CH$_2$)$_n$—OH wherein n is an integer of 1 to 4;

$R^{3f}$ is a hydrogen atom or a $C_{1-6}$ alkyl group;

$Z^f$ is methylene, is preferable, and particularly, a compound wherein $R^{2f}$ is a $C_{1-4}$ alkyl group substituted by —O—(CH$_2$)$_n$—OH wherein n is an integer of 1 to 4, is preferable.

[Compound (Ig)]

A compound represented by the formula:

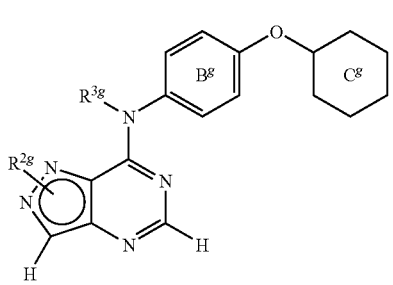

(Ig)

wherein $R^{2g}$ is an optionally substituted group bonded via a carbon atom or a sulfur atom, or $R^{2g}$ and $R^{3g}$ are optionally bonded to form an optionally substituted ring structure, $R^{3g}$ is a hydrogen atom or an optionally substituted aliphatic hydrocarbon group, or $R^{3g}$ is optionally bonded to a carbon atom of the adjacent phenyl group to form an optionally substituted ring structure, $B^g$ is an optionally substituted benzene ring, and $C^g$ is an optionally substituted heterocyclic group.

As the "optionally substituted group bonded via a carbon atom or a sulfur atom" for $R^{2g}$, those similar to the "optionally substituted group bonded via a carbon atom or a sulfur atom" for $R^2$ can be used.

As the "optionally substituted ring structure" formed by $R^{2g}$ and $R^{3g}$ bonded to each other, those similar to the "optionally substituted ring structure" formed by $R^2$ and $R^3$ bonded to each other can be used.

As the "optionally substituted aliphatic hydrocarbon group" for $R^{3g}$, those similar to the "optionally substituted aliphatic hydrocarbon group" for $R^3$ can be used.

As the "optionally substituted ring structure" formed by $R^{3g}$ and a carbon atom of the adjacent phenyl group, those similar to the "optionally substituted ring structure" formed by $R^3$ and a carbon atom of the adjacent phenyl group can be used.

As the "optionally substituted benzene ring" for $B^g$, those similar to the "optionally substituted benzene ring" for $B^a$ can be used.

As the "optionally substituted heterocyclic group" for $C^g$, those similar to the "optionally substituted heterocyclic group" for $C^c$ can be used.

As $R^{2g}$, a $C_{1-8}$ alkyl group, a $C_{2-8}$ alkenyl group, a $C_{2-8}$ alkynyl group, a carbamoyl group, a $C_{1-8}$ alkyl-carbonyl group, a $C_{1-8}$ alkyl-sulfonyl group, a $C_{3-8}$ cycloalkyl group, a $C_{6-18}$ aryl group, a $C_{6-18}$ aryl-$C_{1-4}$ alkyl group, a $C_{6-18}$ aryl-carbonyl group, a $C_{6-18}$ aryl-$C_{1-4}$ alkyl-carbonyl group, a $C_{6-18}$ aryl-sulfonyl group, a heterocyclic group, a heterocyclyl-$C_{1-4}$ alkyl group, a heterocyclyl-carbonyl group or a heterocyclyl-$C_{1-4}$ alkyl-carbonyl group, each of which is optionally substituted by 1 to 5 substituents selected from the group consisting of (a) halogen, (b) oxo, (c) optionally halogenated $C_{1-4}$ alkyl, (d) —$(CH_2)_m$-Q, (e) —$(CH_2)_m$—$Z^1$— (optionally halogenated $C_{1-4}$ alkyl), (f) —$(CH_2)_m$—$Z^1$—$C_{3-8}$ cycloalkyl, (g) —$(CH_2)_m$—$Z^2$—$(CH_2)_n$-Q, (h) —$(CH_2)_m$—$Z^2$—$(CH_2)_n$—$Z^1$— (optionally halogenated $C_{1-4}$ alkyl), (i) —$(CH_2)_m$—$Z^2$—$(CH_2)_n$—$Z^1$—$C_{3-8}$ cycloalkyl, (j) —$(CH_2)_m$—$Z^1$— (optionally substituted heterocyclic group)

(preferably, said heterocyclic group is a 5- to 8-membered heterocyclic group having 1 to 3 hetero atoms selected from a nitrogen atom, an oxygen atom and an optionally oxidized sulfur atom), (k) —$(CH_2)_m$—$Z^2$—$C_{1-4}$ alkoxy, and (l) —$(CH_2)_m$—$Z^2$—$(CH_2)_n$—$Z^1$—$(CH_2)_n$—$Z^1$—$C_{1-4}$ alkyl wherein m is an integer of 0 to 4, n is an integer of 1 to 4, Q is hydroxy, carboxy, cyano, nitro, —$NR^6R^7$, —$CONR^6R^7$ or —$SO_2NR^6R^7$, $Z^1$ is —O—, —CO—, —C(OH)$R^8$—, —C(=N—O$R^8$)—, —S—, —SO—, —SO$_2$—, —N(CO$R^8$)—, —N(CO$_2R^9$)—, —N(SO$_2R^9$)—, —CO—O—, —O—CO—, —CO—$NR^8$—, —$NR^8$—CO—, —$NR^8$—CO$_2$—, —$NR^8$—CO—NH—, —$NR^8$—SO$_2$—, or —$NR^8$—C(=NH)—NH—, $Z^2$ is —O—, —CO—, —C(OH)$R^8$—, —C(=N—O$R^8$)—, —S—, —SO—, —SO$_2$—, —$NR^8$—, —N(CO$R^8$)—, —N(CO$_2R^9$)—, —N(SO$_2R^9$)—, —CO—O—, —O—CO—, —CO—$NR^8$—, —$NR^8$—CO—, —$NR^8$—CO$_2$—, —$NR^8$—CO—NH—, —$NR^8$—C(=NH)—NH—, —$NR^8$—SO$_2$—, or —SO$_2$—$NR^8$—, $(CH_2)_m$ and $(CH_2)_n$ are optionally substituted by 1 to 5 substituents selected from halogen, optionally halogenated $C_{1-4}$ alkyl and hydroxy, and when m or n is not less than 2, a subset —$CH_2CH_2$— of $(CH_2)_m$ and $(CH_2)_n$ is optionally replaced by —CH=CH—.

$R^6$ and $R^7$ are the same or different and each is a hydrogen atom or a $C_{1-4}$ alkyl group, or $R^6$ and $R^7$ are bonded to form, together with a nitrogen atom, a 3- to 8-membered saturated or unsaturated aliphatic heterocyclic group, $R^8$ is a hydrogen atom or $C_{1-4}$ alkyl, and $R^9$ is $C_{1-4}$ alkyl, is preferable.

As compound (Ig), a compound wherein $B^g$ is a benzene ring optionally substituted by $C_{1-4}$ alkyl;

$C^g$ is a 5- to 8-membered heterocyclic group having 1 to 3 hetero atoms selected from a nitrogen atom, an oxygen atom and a sulfur atom, which is optionally substituted by $C_{1-4}$ alkyl;

$R^{2g}$ is (i) a $C_{1-4}$ alkyl group optionally substituted by hydroxy, (ii) a $C_{6-18}$ aryl group optionally substituted by substituent(s) selected from (a) nitro, (b) amino, (c) —CO—$NR^8$—$(CH_2)_n$—O—$C_{1-4}$ alkyl, (d) —$NR^8$—CO—$(CH_2)_n$—O—$C_{1-4}$ alkyl, (e) —$NR^8$—CO—$(CH_2)_n$—$NR^6R^7$, (f) —$NR^8$—CO—$(CH_2)_n$—COOH, (g) —$NR^8$—CO$(CH_2)_n$—CO$_2$—$C_{1-4}$ alkyl, and (h) —$NR^8$—CO—$(CH_2)_m$—$(CH_2)_n$—O—$C_{1-4}$ alkyl, wherein m is an integer of 0 to 4, n is an integer of 1 to 4, $R^6$ and $R^7$ are the same or different and each is a hydrogen atom or a $C_{1-4}$ alkyl group, and $R^8$ is a hydrogen atom or a $C_{1-4}$ alkyl group, or (iii) a $C_{6-18}$ aryl-$C_{1-4}$ alkyl group optionally substituted by substituent(s) selected from (a) carboxy, (b) $C_{1-4}$ alkoxy-carbonyl, and (c) —CO—$NR^8$—$(CH_2)_n$—O—$C_{1-4}$ alkyl, wherein n is an integer of 1 to 4, and $R^8$ is a hydrogen atom or a $C_{1-4}$ alkyl group;

$R^{3g}$ is a hydrogen atom or a $C_{1-6}$ alkyl group; or $R^{2g}$ and $R^{3g}$ are optionally bonded to form $C_{2-4}$ alkylene, is preferable.

As compound (Ig), a compound wherein $R^{2g}$ is (i) a $C_{6-18}$ aryl group optionally substituted by substituent(s) selected from (a) nitro, (b) amino, (c) —CO—$NR^8$—$(CH_2)_n$—O—$C_{1-4}$ alkyl, (d) —$NR^8$—CO—$(CH_2)_n$—O—$C_{1-4}$ alkyl, (e) —$NR^8$—CO—$(CH_2)_n$—$NR^6R^7$, (f) —$NR^8$—CO—$(CH_2)_n$—COOH, (g) —$NR^8$—CO—$(CH_2)_n$—$CO_2$—$C_{1-4}$ alkyl, and (h) —$NR^8$—CO—$(CH_2)_m$—$(CH_2)_n$—O—$C_{1-4}$ alkyl, wherein m is an integer of 0 to 4, n is an integer of 1 to 4, $R^6$ and $R^7$ are the same or different and each is a hydrogen atom or a $C_{1-4}$ alkyl group, and $R^8$ is a hydrogen atom or a $C_{1-4}$ alkyl group, or (ii) a $C_{6-18}$ aryl-$C_{1-4}$ alkyl group substituted by substituent(s) selected from (a) carboxy, (b) $C_{1-4}$ alkoxy-carbonyl, and (c) —CO—$NR^8$—$(CH_2)_n$—O—$C_{1-4}$ alkyl, wherein n is an integer of 1 to 4, and $R^8$ is a hydrogen atom or a $C_{1-4}$ alkyl group, is preferable.

As $R^8$, a hydrogen atom, methyl, ethyl and the like are preferable, and a hydrogen atom is particularly preferable.

[Compound (Ih)]

A compound (I) selected from the following (A) to (H).

(A) A compound (I) wherein W is $C(R^1)$;

A is a phenyloxy-$C_{6-18}$ aryl group wherein the phenyloxy moiety is optionally substituted by 1 to 5 substituents selected from (i) halogen, (ii) optionally halogenated $C_{1-4}$ alkyl, (iii) hydroxy-$C_{1-4}$ alkyl, (iv) heterocyclyl-$C_{1-4}$ alkyl (preferably, 5- to 8-membered heterocyclyl-$C_{1-4}$ alkyl, said 5- to 8-membered heterocyclyl has 1 to 3 hetero atoms selected from a nitrogen atom, an oxygen atom and an optionally oxidized sulfur atom, such as imidazolyl, triazolyl and the like), (v) optionally halogenated $C_{1-4}$ alkyloxy, (vi) $C_{1-4}$ alkyl-carbonyl, (vii) cyano, (viii) carbamoyl optionally substituted by $C_{1-8}$ alkyl, and (ix) $C_{1-4}$ alkoxy-carbonyl, and the $C_{6-18}$ aryl moiety is optionally further substituted by 1 to 4 substituents selected from halogen, $C_{1-4}$ alkyl, hydroxy-$C_{1-4}$ alkyl, $C_{1-4}$ alkyloxy, carboxy and $C_{1-4}$ alkoxy-carbonyl;

$X^1$ is —$NR^{3'}$— wherein $R^{3'}$ is a hydrogen atom or a $C_{1-6}$ alkyl group;

$R^1$ is (i) a hydrogen atom, (ii) a cyano group, or (iii) a $C_{1-4}$ alkyl group or a $C_{2-4}$ alkenyl group, each of which is optionally substituted by —$NR^8$—CO—$(CH_2)_n$—$NR^6R^7$ wherein n is an integer of 1 to 4, $R^6$ and $R^7$ are the same or different and each is a hydrogen atom or a $C_{1-4}$ alkyl group, $R^8$ is a hydrogen atom or a $C_{1-4}$ alkyl group, and when n is not less than 2, a subset —$CH_2CH_2$— of $(CH_2)_n$ is optionally replaced by —CH=CH—;

$R^2$ is (i) a hydrogen atom or (ii) a $C_{1-8}$ alkyl group, a $C_{2-8}$ alkenyl group or a $C_{2-8}$ alkynyl group, each of which is optionally substituted by substituent(s) selected from (a) hydroxy, (b) carboxy, (c) cyano, (d) optionally halogenated $C_{1-4}$ alkyloxy, (e) —O—$(CH_2)_n$—OH, (f) —O—$(CH_2)_n$—O—CO—$NH_2$, (g) —O—$(CH_2)_n$—O— (optionally halogenated $C_{1-4}$ alkyl), (h) —O—$(CH_2)_n$—$SO_2$— (optionally halogenated $C_{1-4}$ alkyl), (i) —O—$(CH_2)_n$—$SO_2$—$C_{6-18}$ aryl, (j) —O—$(CH_2)_n$—$SO_2$—$(CH_2)_n$—OH, (k) —O—$(CH_2)_n$—$NR^8$—CO—$C_{1-4}$ alkyl, (l) —O—$(CH_2)_n$—$NR^8$—CO—$(CH_2)_n$—$SO_2$—$C_{1-4}$ alkyl, (m) —O—$(CH_2)_n$—$NR^8$—$SO_2$— (optionally halogenated $C_{1-4}$ alkyl), (n) —CO—$NR^8$—$(CH_2)_n$—OH, (o) —CO—$NR^8$—$(CH_2)_n$—$SO_2$— (optionally halogenated $C_{1-4}$ alkyl), (p) —CO—$NR^8$—O—$C_{1-4}$ alkyl, (q) —$NR^6R^7$, (r) —$NR^8$—$(CH_2)_n$—OH, (s) —$NR^8$—$(CH_2)_n$—$SO_2$—$C_{1-4}$ alkyl, (t) —$NR^8$—CO— (optionally halogenated $C_{1-4}$ alkyl), (u) —$NR^8$—CO—$(CH_2)_n$—OH, (v) —$NR^8$—CO—$(CH_2)_n$—CN, (w) —$NR^8$—CO—$(CH_2)_n$—$NR^6R^7$, (x) —$NR^8$—CO—$(CH_2)_n$—O—$C_{1-4}$ alkyl, (y) —$NR^8$—CO—$(CH_2)_n$—SO— (optionally halogenated $C_{1-4}$ alkyl), (z) —$NR^8$—CO—$(CH_2)_n$—$SO_2$— (optionally halogenated $C_{1-4}$ alkyl), (aa) —$NR^8$—CO—$(CH_2)_n$—$SO_2$—$C_{3-8}$ cycloalkyl, (bb) —$NR^8$—CO—$(CH_2)_n$—$NR^8$—$SO_2$—$C_{1-4}$ alkyl, (cc) —$NR^8$—$CO_2$—$(CH_2)_n$—$SO_2$—$C_{1-4}$ alkyl, (dd) —$NR^8$—CO—NH—$(CH_2)_n$—$SO_2$—$C_{1-4}$ alkyl, (ee) —$NR^8$—CO—NH—O—$C_{1-4}$ alkyl, (ff) —$NR^8$—CO—NH—$(CH_2)_n$—O—$C_{1-4}$ alkyl, (gg) —$NR^8$—C(=NH)—NH—$C_{1-4}$ alkyl, (hh) —$NR^8$—$SO_2$—$(CH_2)_n$—$SO_2$—$C_{1-4}$ alkyl, (ii) —S—$(CH_2)_n$—OH, (jj) —SO—$(CH_2)_n$—OH, (kk) —$SO_2$—$(CH_2)_n$—OH, and (ll) —$NR^8$—CO— (optionally substituted heterocyclic group)

(preferably, said heterocyclic group is a 5- to 8-membered heterocyclic group having 1 to 3 hetero atoms selected from a nitrogen atom, an oxygen atom and an optionally oxidized sulfur atom, which is optionally substituted by substituent(s)

selected from hydroxy, $C_{1-4}$ alkyl, optionally oxidized $C_{1-4}$ alkylthio, —CO—$C_{1-4}$ alkyl, —CO—O—$C_{1-4}$ alkyl, —CO—NH—$C_{1-4}$ alkyl, —CONH$_2$, —SO$_2$—$C_{1-4}$ alkyl, —SO$_2$—NH—$C_{1-4}$ alkyl, —SO$_2$NH$_2$ and the like), wherein n is an integer of 1 to 4, $R^6$ and $R^7$ are the same or different and each is a hydrogen atom or a $C_{1-4}$ alkyl group, $R^8$ is a hydrogen atom or a $C_{1-4}$ alkyl group, $(CH_2)_n$ is optionally substituted by optionally halogenated $C_{1-4}$ alkyl or hydroxy, and when n is not less than 2, and a subset —CH$_2$CH$_2$— of $(CH_2)_n$ is optionally replaced by —CH=CH—; or $R^1$ and $R^2$ are optionally bonded to form

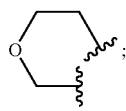

or $R^2$ and $R^{3'}$ are optionally bonded to form $C_{2-4}$ alkylene optionally substituted by an imino group, particularly preferably, $R^2$ is a $C_{1-8}$ alkyl group, a $C_{2-8}$ alkenyl group or a $C_{2-8}$ alkynyl group (particularly, a $C_{1-8}$ alkyl group), each of which is optionally substituted by substituent (s) selected from (a) hydroxy, (b) carboxy, (c) cyano, (d) optionally halogenated $C_{1-4}$ alkyloxy, (e) —O—(CH$_2$)$_n$—OH (wherein $(CH_2)_n$ is optionally substituted by hydroxy), (f) —O—(CH$_2$)$_n$—O—CO—NH$_2$, (g) —O—(CH$_2$)$_n$—O— (optionally halogenated $C_{1-4}$ alkyl), (h) —O—(CH$_2$)$_n$—SO$_2$— (optionally halogenated $C_{1-4}$ alkyl), (i) —O—(CH$_2$)$_n$—SO$_2$—$C_{6-18}$ aryl, (j) —O—(CH$_2$)$_n$—SO$_2$—(CH$_2$)$_n$—OH, (k) —O—(CH$_2$)$_n$—NR$^8$—CO—$C_{1-4}$ alkyl, (l) —O—(CH$_2$)$_n$—NR$^8$—CO—(CH$_2$)$_n$—SO$_2$—$C_{1-4}$ alkyl, (m) —O—(CH$_2$)$_n$—NR$^8$—SO$_2$— (optionally halogenated $C_{1-4}$ alkyl), (n) —CO—NR$^8$—(CH$_2$)$_n$—OH, (o) —CO—NR$^8$—(CH$_2$)$_n$—SO$_2$— (optionally halogenated $C_{1-4}$ alkyl), (p) —CO—NR$^8$—O—$C_{1-4}$ alkyl, (q) —NR$^6$R$^7$, (r) —NR$^8$—(CH$_2$)$_n$—OH, (s) —NR$^8$—(CH$_2$)$_n$—SO$_2$—$C_{1-4}$ alkyl, (t) —NR$^8$—CO— (optionally halogenated $C_{1-4}$ alkyl), (u) —NR$^8$—CO—(CH$_2$)$_n$—OH (wherein $(CH_2)_n$ is optionally substituted by optionally halogenated $C_{1-4}$ alkyl or hydroxy), (v) —NR$^8$—CO—(CH$_2$)$_n$—CN, (w) —NR$^8$—CO—(CH$_2$)$_n$—NR$^6$R$^7$ (when n is not less than 2, a subset —CH$_2$CH$_2$— of $(CH_2)_n$ is optionally replaced by —CH=CH—), (x) —NR$^8$—CO—(CH$_2$)$_n$—O—$C_{1-4}$ alkyl, (y) —NR$^8$—CO—(CH$_2$)$_n$—SO— (optionally halogenated $C_{1-4}$ alkyl), (z) —NR$^8$—CO—(CH$_2$)$_n$—SO$_2$— (optionally halogenated $C_{1-4}$ alkyl)

(wherein $(CH_2)_n$ is optionally substituted by $C_{1-4}$ alkyl), (aa) —NR$^8$—CO—(CH$_2$)$_n$—SO$_2$—$C_{3-8}$ cycloalkyl, (bb) —NR$^8$—CO—(CH$_2$)$_n$—NR$^8$—SO$_2$—$C_{1-4}$ alkyl, (cc) —NR$^8$—CO$_2$—(CH$_2$)$_n$—SO$_2$—$C_{1-4}$ alkyl, (dd) —NR$^8$—CO—NH—(CH$_2$)$_n$—SO$_2$—$C_{1-4}$ alkyl, (ee) —NR$^8$—CO—NH—O—$C_{1-4}$ alkyl, (ff) —NR$^8$—CO—NH—(CH$_2$)$_n$—O—$C_{1-4}$ alkyl, (gg) —NR$^8$—C(=NH)—NH—$C_{1-4}$ alkyl, (hh) —NR$^8$—SO$_2$—(CH$_2$)$_n$—SO$_2$—$C_{1-4}$ alkyl, (ii) —S—(CH$_2$)$_n$—OH, (jj) —SO—(CH$_2$)$_n$—OH (kk) —SO$_2$—(CH$_2$)$_n$—OH, and (ll) —NR$^8$—CO— (optionally substituted heterocyclic group)

(preferably, said heterocyclic group is a 5- to 8-membered heterocyclic group having 1 to 3 hetero atoms selected from a nitrogen atom, an oxygen atom and an optionally oxidized sulfur atom, which is optionally substituted by substituent(s) selected from hydroxy, $C_{1-4}$ alkyl, optionally oxidized $C_{1-4}$ alkylthio, —CO—$C_{1-4}$ alkyl, —CO—O—$C_{1-4}$ alkyl, —CO—NH—$C_{1-4}$ alkyl, —CONH$_2$, —SO$_2$—$C_{1-4}$ alkyl, —SO$_2$—NH—$C_{1-4}$ alkyl, —SO$_2$NH$_2$ and the like), wherein n is an integer of 1 to 4, $R^6$ and $R^7$ are the same or different and each is a hydrogen atom or a $C_{1-4}$ alkyl group, and $R^8$ is a hydrogen atom or a $C_{1-4}$ alkyl group.

(B) A compound (I) wherein W is C($R^1$);

A is a phenyl-$C_{1-3}$ alkyloxy-$C_{6-18}$ aryl group wherein the phenyl moiety is optionally substituted by 1 to 5 substituents selected from halogen, optionally halogenated $C_{1-4}$ alkyl and cyano, and the $C_{6-18}$ aryl moiety is optionally further substituted by 1 to 4 substituents selected from halogen, $C_{1-4}$ alkyl optionally having hydroxy and $C_{1-4}$ alkyloxy;

$X^1$ is —NR$^3$— wherein $R^3$ is a hydrogen atom or a $C_{1-6}$ alkyl group;

$R^1$ is (i) a hydrogen atom, or (ii) a $C_{1-4}$ alkyl group or a $C_{2-4}$ alkenyl group, each of which is optionally substituted by substituent(s) selected from (a) hydroxy, (b) amino, (c) —NR$^8$—CO—(CH$_2$)$_n$—NR$^6$R$^7$, and (d) —NR$^8$—CO—(CH$_2$)$_n$—O—$C_{1-4}$ alkyl wherein n is an integer of 1 to 4, and $R^6$ and $R^7$ are the same or different and each is a hydrogen atom or a $C_{1-4}$ alkyl group, and when n is not less than 2, a subset —$CH_2$—$CH_2$— of $(CH_2)_n$ is optionally replaced by —CH═CH—, (iii) a $C_{6-18}$ aryl group optionally substituted by substituent(s) selected from (a) amino, (b) carboxy, and (c) —$NR^8$—CO—$(CH_2)_n$—O—$C_{1-4}$ alkyl, wherein n is an integer of 1 to 4, and $R^8$ is a hydrogen atom or a $C_{1-4}$ alkyl group, or (iv) a 5- to 8-membered heterocyclic group having 1 to 3 hetero atoms selected from a nitrogen atom, an oxygen atom and a sulfur atom;

$R^2$ is (i) a hydrogen atom, (ii) a $C_{1-8}$ alkyl group optionally substituted by substituent(s) selected from (a) halogen, (b) hydroxy, (c) $C_{1-4}$ alkyloxy, (d) —O—$(CH_2)_n$—OH, (e) —O—$(CH_2)_n$—O—$C_{1-4}$ alkyl, (f) —CO—$NR^8$—$(CH_2)_n$—OH, (g) —$NR^6R^7$, and (h) —$NR^8$—$(CH_2)_n$—OH, wherein n is an integer of 1 to 4, $R^6$ and $R^7$ are the same or different and each is a hydrogen atom or a $C_{1-4}$ alkyl group, and $R^8$ is a hydrogen atom or a $C_{1-4}$ alkyl group, (iii) a $C_{6-18}$ aryl-$C_{1-4}$ alkyl group optionally substituted by substituent(s) selected from (a) $C_{1-4}$ alkyl optionally having hydroxy, (b) carboxy, (c) $C_{1-4}$ alkoxy-carbonyl, (d) 5- to 8-membered heterocyclyl-carbonyl having 1 to 3 hetero atoms selected from a nitrogen atom, an oxygen atom and a sulfur atom, which optionally has substituent(s) selected from hydroxy and $C_{1-4}$ alkyl, and (e) $C_{1-4}$ alkyl-carbamoyl optionally having substituent(s) selected from hydroxy and carbamoyl, (iv) a $C_{6-18}$ aryl-carbonyl group optionally substituted by $C_{1-4}$ alkoxy, (v) a $C_{6-18}$ aryl-sulfonyl group optionally substituted by $C_{1-4}$ alkoxy, or (vi) a 5- to 8-membered heterocyclyl-$C_{1-4}$ alkyl group having 1 to 3 hetero atoms selected from a nitrogen atom, an oxygen atom and a sulfur atom, which is optionally substituted by substituent(s) selected from (a) carboxy, and (b) $C_{1-4}$ alkoxy-carbonyl; or $R^2$ and $R^{3'}$ are optionally bonded to form $C_{2-4}$ alkylene.

(C) A compound (I) wherein W is $C(R^1)$;

A is a 5- to 8-membered heterocyclyloxy-$C_{6-18}$ aryl group containing 1 to 3 hetero atoms selected from a nitrogen atom, an oxygen atom and a sulfur atom, wherein the heterocyclyloxy moiety is optionally substituted by 1 to 5 substituents selected from (i) halogen, (ii) $C_{1-4}$ alkyl, (iii) $C_{1-4}$ alkyl-carbonyl, (iv) optionally halogenated $C_{1-4}$ alkoxy-carbonyl, (v) $C_{3-8}$ cycloalkyl-carbonyl, and (vi) a carbamoyl group optionally substituted by substituent(s) selected from (a) optionally halogenated $C_{1-8}$ alkyl, (b) $C_{3-8}$ cycloalkyl, and (c) $C_{6-18}$ aryl optionally substituted by substituent(s) selected from halogen, $C_{1-4}$ alkyl and $C_{1-4}$ alkyloxy, and the $C_{6-18}$ aryl moiety is optionally further substituted by 1 to 4 substituents selected from halogen and optionally halogenated $C_{1-4}$ alkyl;

$X^1$ is —$NR^{3'}$— wherein $R^{3'}$ is a hydrogen atom or a $C_{1-6}$ alkyl group;

$R^1$ is (i) a hydrogen atom, (ii) a $C_{1-4}$ alkyl group or a $C_{2-4}$ alkenyl group, each of which is optionally substituted by substituent(s) selected from (a) hydroxy, (b) amino, (c) —$NR^8$—CO—$(CH_2)_n$—$NR^6R^7$, and (d) —$NR^8$—CO—$(CH_2)_n$—O—$C_{1-4}$ alkyl, wherein n is an integer of 1 to 4, $R^6$ and $R^7$ are the same or different and each is a hydrogen atom or a $C_{1-4}$ alkyl group, $R^8$ is a hydrogen atom or a $C_{1-4}$ alkyl group, and when n is not less than 2, a subset —$CH_2CH_2$— of $(CH_2)_n$ is optionally replaced by —CH═CH—, (iii) a $C_{6-18}$ aryl group optionally substituted by substituent(s) selected from (a) $C_{1-4}$ alkyl optionally substituted by substituent(s) selected from hydroxy, —$NR^8$—$(CH_2)_n$—$SO_2$—$C_{1-4}$ alkyl and —$NR^8$—CO—$(CH_2)_n$—O—$C_{1-14}$ alkyl, (b) amino, (c) $C_{1-4}$ alkyloxy, (d) carboxy, and (e) —$NR^8$—CO—$(CH_2)_n$—O—$C_{1-4}$ alkyl, wherein n is an integer of 1 to 4, and $R^8$ is a hydrogen atom or a $C_{1-4}$ alkyl group, or (iv) a 5- to 8-membered heterocyclic group having 1 to 3 hetero atoms selected from a nitrogen atom, an oxygen atom and a sulfur atom;

$R^2$ is (i) a hydrogen atom, (ii) a $C_{1-4}$ alkyl group optionally substituted by substituent(s) selected from (a) halogen, (b) hydroxy, (c) $C_{1-4}$ alkyloxy, (d) carboxy, (e) $C_{1-4}$ alkoxy-carbonyl, (f) —O—$(CH_2)_n$—OH, (g) —O—$(CH_2)_n$—O—$C_{1-4}$ alkyl, (h) —CO—$NR^8$—$(CH_2)_n$—OH, and (i) —$NR^8$—CO—$(CH_2)_n$—$SO_2$—$C_{1-4}$ alkyl wherein n is an integer of 1 to 4, and $R^8$ is a hydrogen atom or a $C_{1-4}$ alkyl group, or (iii) a $C_{6-18}$ aryl-$C_{1-14}$ alkyl group optionally substituted by $C_{1-4}$ alkyl optionally having hydroxy; or $R^2$ and $R^3$ are optionally bonded to form $C_{2-4}$ alkylene.

(D) A compound (I) wherein W is $C(R^1)$;

A is 5- to 8-membered heterocyclyl-$C_{1-3}$ alkyloxy-$C_{6-18}$ aryl group containing 1 to 3 hetero atoms selected from a nitrogen atom, an oxygen atom and a sulfur atom;

wherein the $C_{6-18}$ aryl moiety is optionally further substituted by halogen;

$X^1$ is —$NR^{3'}$— wherein $R^{3'}$ is a hydrogen atom or a $C_{1-6}$ alkyl group;

$R^1$ is (i) a hydrogen atom or (ii) a 5- to 8-membered heterocyclic group having 1 to 3 hetero atoms selected from a nitrogen atom, an oxygen atom and a sulfur atom;

$R^2$ is (i) a hydrogen atom, (ii) $C_{1-4}$ alkyl optionally substituted by substituent(s) selected from (a) $C_{1-4}$ alkyloxy, (b) —O—$(CH_2)_n$—OH, and (c) —$NR^8$—CO—$(CH_2)_n$—$SO_2$—$C_{1-4}$ alkyl, wherein n is an integer of 1 to 4, and $R^8$ is a hydrogen atom or a $C_{1-4}$ alkyl group, or (iii) a 5- to 8-membered heterocyclyl-$C_{1-4}$ alkyl group having 1 to 3 hetero atoms selected from a nitrogen atom, an oxygen atom and a sulfur atom, which is optionally substituted by substituent(s) selected from (a) carboxy, and (b) $C_{1-4}$ alkoxy-carbonyl.

(E) A compound (I) wherein W is N;

A is a phenyloxy-$C_{6-18}$ aryl group wherein the phenyloxy moiety

A is optionally substituted by 1 to 5 substituents selected from optionally halogenated $C_{1-4}$ alkyl and cyano, and the $C_{6-18}$ aryl moiety is optionally further substituted by 1 to 4 substituents selected from halogen and $C_{1-4}$ alkyl;

$X^1$ is —$NR^{3'}$— wherein $R^{3'}$ is a hydrogen atom or a $C_{1-6}$ alkyl group;

$R^2$ is (i) a hydrogen atom or (ii) a $C_{1-4}$ alkyl group optionally substituted by —O—$(CH_2)_n$—OH wherein n is an integer of 1 to 4.

(F) A compound (I) wherein W is N;

A is a phenyl-$C_{1-3}$ alkyloxy-$C_{6-18}$ aryl group wherein the phenyl moiety is optionally substituted by 1 to 5 substituents selected from halogen and cyano, and the $C_{6-18}$ aryl moiety is optionally further substituted by 1 to 4 substituents selected from halogen and $C_{1-4}$ alkyl;

$X^1$ is —$NR^{3'}$— wherein $R^{3'}$ is a hydrogen atom or a $C_{1-6}$ alkyl group;

$R^2$ is (i) a hydrogen atom, (ii) a $C_{1-4}$ alkyl group optionally substituted by 1 to 5 substituents selected from the group consisting of (a) hydroxy, (b) —O—$(CH_2)_n$—OH, (c) —$NR^8$—$(CH_2)_n$—O—$C_{1-4}$ alkyl, (d) —$NR^8$—$(CH_2)_n$-heterocyclic group (preferably, said heterocyclic group is a 5- to 8-membered heterocyclic group having 1 to 3 hetero atoms selected from a nitrogen atom, an oxygen atom and a sulfur atom), and (e) —$NR^8$—$(CH_2)_n$—$SO_2$—$C_{1-4}$ alkyl, wherein n is an integer of 1 to 4, and $R^8$ is a hydrogen atom or a $C_{1-4}$ alkyl group, (iii) a $C_{6-18}$ aryl group optionally substituted by $C_{1-4}$ alkyl optionally substituted by substituent(s) selected from hydroxy, —$NR^8$—$(CH_2)_n$—OH, —$NR^8$—$(CH_2)_n$-heterocyclic group (preferably, said heterocyclic group is a 5- to 8-membered heterocyclic group having 1 to 3 hetero atoms selected from a nitrogen atom, an oxygen atom and a sulfur atom) and —$NR^8$—$(CH_2)_n$—$SO_2$—$C_{1-4}$ alkyl, or (iv) a $C_{6-18}$ aryl-$C_{1-4}$ alkyl group optionally substituted by 1 to 5 substituents selected from the group consisting of (a) carboxy, (b) $C_{1-4}$ alkoxy-carbonyl, and (c) —CO—$NR^8$—$(CH_2)_n$—O—$C_{1-4}$ alkyl, wherein n is an integer of 1 to 4, and $R^8$ is a hydrogen atom or a $C_{1-4}$ alkyl group; or $R^2$ and $R^{3'}$ are optionally bonded to form $C_{2-4}$ alkylene.

(G) A compound (I) wherein W is N;

A is a 5- to 8-membered heterocyclyloxy-$C_{6-18}$ aryl group containing 1 to 3 hetero atoms selected from a nitrogen atom, an oxygen atom and a sulfur atom, wherein the heterocyclyloxy moiety is optionally substituted by $C_{1-4}$ alkyl, and the $C_{6-18}$ aryl moiety is optionally further substituted by $C_{1-4}$ alkyl;

$X^1$ is —$NR^{3'}$— wherein $R^{3'}$ is a hydrogen atom or a $C_{1-6}$ alkyl group;

$R^2$ is (i) a hydrogen atom, (ii) a $C_{1-4}$ alkyl group optionally substituted by hydroxy, (iii) a $C_{6-18}$ aryl group optionally substituted by substituent(s) selected from (a) nitro, (b) amino, (c) —CO—$NR^8$—$(CH_2)_n$—O—$C_{1-4}$ alkyl, (d) —$NR^8$—CO—$(CH_2)_n$—O—$C_{1-4}$ alkyl, (e) —$NR^8$—CO—$(CH_2)_n$—$NR^6R^7$, (f) —$NR^8$—CO—$(CH_2)_n$—COOH, (g) —$NR^8$—CO—$(CH_2)_n$—$CO_2$—$C_{1-4}$ alkyl, and (h) —$NR^8$—CO—$(CH_2)_m$—O—$(CH_2)_n$—O—$C_{1-4}$ alkyl, wherein m is an integer of 0 to 4, n is an integer of 1 to 4, $R^6$ and $R^7$ are the same or different and each is a hydrogen atom or a $C_{1-4}$ alkyl group, and $R^8$ is a hydrogen atom or a $C_{1-4}$ alkyl group, or (iv) a $C_{6-18}$ aryl-$C_{1-4}$ alkyl group optionally substituted by substituent(s) selected from (a) carboxy, (b) $C_{1-4}$ alkoxy-carbonyl, and (c) —CO—$NR^8$—$(CH_2)_n$—O—$C_{1-4}$ alkyl, wherein n is an integer of 1 to 4, and $R^8$ is a hydrogen atom or a $C_{1-4}$ alkyl group; or $R^2$ and $R^{3'}$ are optionally bonded to form $C_{2-4}$ alkylene.

(H) A compound (I) wherein W is CH;

A is a $C_{6-18}$ aryl group optionally substituted by substituent(s) selected from (a) carboxy, (b) $C_{1-4}$ alkoxy-carbonyl, (c) a 5- to 8-membered heterocyclyl-carbonyl group containing 1 to 3 hetero atoms selected from a nitrogen atom, an oxygen atom and a sulfur atom (preferably, a 5- to 8-membered cyclic amino-carbonyl group optionally having 1 or 2 hetero atoms selected from a nitrogen atom, an oxygen atom and a sulfur atom), which is optionally substituted by $C_{6-18}$ aryl-$C_{1-4}$ alkyl, (d) a carbamoyl group optionally substituted by $C_{6-18}$ aryl-$C_{1-4}$ alkyl, and (e) a ureido group optionally substituted by $C_{6-18}$ aryl-$C_{1-4}$ alkyl;

$X^1$ is —$NR^{3'}$— wherein $R^{3'}$ is a hydrogen atom or a $C_{1-6}$ alkyl group; and $R^2$ is a hydrogen atom.

[Compound (II)]

A compound (I) wherein A is a $C_{6-18}$ aryl group substituted by substituent(s) selected from (i) a phenyloxy group substituted by 1 to 5 substituents selected from (a) halogen, (b) optionally halogenated $C_{1-4}$ alkyl, (c) hydroxy-$C_{1-4}$ alkyl, (d) heterocyclyl-$C_{1-4}$ alkyl (preferably, 5- to 8-membered heterocyclyl-$C_{1-4}$ alkyl, said 5- to 8-membered heterocyclyl has 1 to 3 hetero atoms selected from a nitrogen atom, an oxygen atom and an optionally oxidized sulfur atom, such as imidazolyl, triazolyl and the like), (e) optionally halogenated $C_{1-4}$ alkyloxy, (f) $C_{1-4}$ alkyl-carbonyl, (g) cyano, (h) carbamoyl optionally substituted by $C_{1-8}$ alkyl, and (i) $C_{1-4}$ alkoxy-carbonyl, (ii) a phenyl-$C_{1-3}$ alkyloxy group substituted by 1 to 5 substituents selected from (a) halogen, (b) optionally halogenated $C_{1-4}$ alkyl, (c) hydroxy-$C_{1-4}$ alkyl, (d) heterocyclyl-$C_{1-4}$ alkyl (preferably, 5- to 8-membered heterocyclyl-$C_{1-4}$ alkyl, said 5- to 8-membered heterocyclyl has 1 to 3 hetero atoms selected from a nitrogen atom, an oxygen atom and an optionally oxidized sulfur atom, such as imidazolyl, triazolyl and the like), (e) optionally halogenated $C_{1-4}$ alkyloxy, (f) $C_{1-4}$ alkyl-carbonyl, (g) cyano, (h) carbamoyl optionally substituted by $C_{1-8}$ alkyl, and (i) $C_{1-4}$ alkoxy-carbonyl, (iii) a 5- to 8-membered heterocyclyloxy group containing 1 to 3 hetero atoms selected from a nitrogen atom, an oxygen atom and a sulfur atom, which is substituted by 1 to 5 substituents selected from (a) halogen, (b) optionally halogenated $C_{1-4}$ alkyl, (c) hydroxy-$C_{1-4}$ alkyl, (d) heterocyclyl-$C_{1-4}$ alkyl (preferably, 5- to 8-membered heterocyclyl-$C_{1-4}$ alkyl, said 5- to 8-membered heterocyclyl has 1 to 3 hetero atoms selected from a nitrogen atom, an oxygen atom and an optionally oxidized sulfur atom, such as imidazolyl, triazolyl and the like), (e) optionally halogenated $C_{1-4}$ alkyloxy, (f) $C_{1-4}$ alkyl-carbonyl, (g) cyano, (h) carbamoyl optionally substituted by $C_{1-8}$ alkyl, and (i) $C_{1-4}$ alkoxy-carbonyl, and (iv) 5- to 8-membered heterocyclyl-$C_{1-3}$ alkyloxy containing 1 to 3 hetero atoms selected from a nitrogen atom, an oxygen atom and a sulfur atom, which is substituted by 1 to 5 substituents selected from (a) halogen, (b) optionally halogenated $C_{1-4}$ alkyl, (c) hydroxy-$C_{1-4}$ alkyl, (d) heterocyclyl-$C_{1-4}$ alkyl (preferably, 5- to 8-membered heterocyclyl-$C_{1-4}$ alkyl, said 5- to 8-membered heterocyclyl has 1 to 3 hetero atoms selected from a nitrogen atom, an oxygen atom and an optionally oxidized sulfur atom, such as imidazolyl, triazolyl and the like), (e) optionally halogenated $C_{1-4}$ alkyloxy, (f) $C_{1-4}$ alkyl-carbonyl, (g) cyano, (h) carbamoyl optionally substituted by $C_{1-8}$ alkyl, and (i) $C_{1-4}$ alkoxy-carbonyl;

wherein the $C_{6-18}$ aryl group is optionally further substituted by 1 to 4 substituents selected from halogen and optionally halogenated $C_{1-4}$ alkyl;

$R^1$ is a hydrogen atom;

$R^2$ is a $C_{1-8}$ alkyl group, a $C_{2-8}$ alkenyl group or a $C_{2-8}$ alkynyl group, each of which is substituted by substituent(s) selected from (a) hydroxy, (b) carboxy, (c) cyano, (d) optionally halogenated $C_{1-4}$ alkyloxy, (e) —O—$(CH_2)_n$—OH, (f) —O—$(CH_2)_n$—O—CO—$NH_2$, (g) —O—$(CH_2)_n$—O— (optionally halogenated $C_{1-4}$ alkyl), (h) —O—$(CH_2)_n$—$SO_2$— (optionally halogenated $C_{1-4}$ alkyl), (i) —O—$(CH_2)_n$—$SO_2$—$C_{6-18}$ aryl, (j) —O—$(CH_2)_n$—$SO_2$—$(CH_2)_n$—OH, (k) —O—$(CH_2)_n$—$NR^8$—CO—$C_{1-4}$ alkyl, (l) —O—$(CH_2)_n$—$NR^8$—CO—$(CH_2)_n$—$SO_2$—$C_{1-4}$ alkyl, (m) —O—$(CH_2)_n$—$NR^8$—$SO_2$— (optionally halogenated $C_{1-4}$ alkyl), (n) —CO—$NR^8$—$(CH_2)_n$—OH, (o) —CO—$NR^8$—$(CH_2)_n$—$SO_2$— (optionally halogenated $C_{1-4}$ alkyl), (p) —CO—$NR^8$—O—$C_{1-4}$ alkyl, (q) —$NR^6R^7$, (r) —$NR^8$—$(CH_2)_n$—OH, (s) —$NR^8$—$(CH_2)_n$—$SO_2$—$C_{1-4}$ alkyl, (t) —$NR^8$—CO— (optionally halogenated $C_{1-4}$ alkyl), (u) —$NR^8$—CO—$(CH_2)_n$—OH, (v) —$NR^8$—CO—$(CH_2)_n$—CN, (w) —$NR^8$—CO—$(CH_2)_n$—$NR^6R^7$, (x) —$NR^8$—CO—$(CH_1)$—O—$C_{1-4}$ alkyl, (y) —$NR^8$—CO—$(CH_1)$—SO— (optionally halogenated $C_{1-4}$ alkyl), (z) —$NR^8$—CO—$(CH_2)_n$—$SO_2$— (optionally halogenated $C_{1-4}$ alkyl), (aa) —$NR^8$—CO—$(CH_2)_n$—$SO_2$—$C_{3-8}$ cycloalkyl, (bb) —$NR^8$—CO—$(CH_2)_n$—$NR^8$—$SO_2$—$C_{1-4}$ alkyl, (cc) —$NR^8$—$CO_2$—$(CH_2)_n$—$SO_2$—$C_{1-4}$ alkyl, (dd) —$NR^8$—CO—NH—$(CH_2)_n$—$SO_2$—$C_{1-4}$ alkyl, (ee) —$NR^8$—CO—NH—O—$C_{1-4}$ alkyl, (ff) —$NR^8$—CO—NH—$(CH_2)_n$—O—$C_{1-4}$ alkyl, (gg) —$NR^8$—C(=NH)—NH—$C_{1-4}$ alkyl, (hh) —$NR^8$—$SO_2$—$(CH_2)_n$—$SO_2$—$C_{1-4}$ alkyl, (ii) —S—$(CH_2)_n$—OH, (jj) —SO—$(CH_2)_n$—OH, (kk) —$SO_2$—$(CH_2)_n$—OH, and (ll) —$NR^8$—CO— (optionally substituted heterocyclic group)

(preferably, said heterocyclic group is a 5- to 8-membered heterocyclic group having 1 to 3 hetero atoms selected from a nitrogen atom, an oxygen atom and an optionally oxidized sulfur atom, which is optionally substituted by substituent(s) selected from hydroxy, $C_{1-4}$ alkyl, optionally oxidized $C_{1-4}$ alkylthio, —CO—$C_{1-4}$ alkyl, —CO—O—$C_{1-4}$ alkyl, —CO—NH—$C_{1-4}$ alkyl, —$CONH_2$, —$SO_2$—$C_{1-4}$ alkyl, —$SO_2$—NH—$C_{1-4}$ alkyl, —$SO_2NH_2$ and the like), wherein n is an integer of 1 to 4, $R^6$ and $R^7$ are the same or different and each is a hydrogen atom or a $C_{1-4}$ alkyl group, $R^8$ is a hydrogen atom or a $C_{1-4}$ alkyl group, $(CH_2)_n$ is optionally substituted by optionally halogenated $C_{1-4}$ alkyl or hydroxy, and when n is not less than 2, a subset —$CH_2CH_2$— of $(CH_2)_n$ is optionally replaced by —CH=CH—;

$R^3$ is a hydrogen atom or a $C_{1-6}$ alkyl group; or $R^1$ and $R^2$ are optionally bonded to form

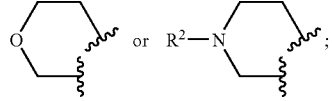

or $R^2$ and $R^3$ are optionally bonded to form $C_{2-4}$ alkylene optionally substituted by an imino group.

Particularly preferably, $R^2$ is a $C_{1-8}$ alkyl group, a $C_{2-8}$ alkenyl group or a $C_{2-8}$ alkynyl group (particularly, a $C_{1-8}$ alkyl group), each of which is optionally substituted by substituent(s) selected from (a) hydroxy, (b) carboxy, (c) cyano, (d) optionally halogenated $C_{1-4}$ alkyloxy, (e) —O—$(CH_2)_n$—OH (wherein $(CH_2)_n$ is optionally substituted by hydroxy), (f) —O—$(CH_2)_n$—O—CO—$NH_2$, (g) —O—$(CH_2)_n$—O— (optionally halogenated $C_{1-4}$ alkyl), (h) —O—$(CH_2)_n$—$SO_2$— (optionally halogenated $C_{1-4}$ alkyl), (i) —O—$(CH_2)_n$—$SO_2$—$C_{6-18}$ aryl, (j) —O—$(CH_2)_n$—$SO_2$—$(CH_2)_n$—OH, (k) —O—$(CH_2)_n$—$NR^8$—CO—$C_{1-4}$ alkyl, (l) —O—$(CH_2)_n$—$NR^8$—CO—$(CH_2)_n$—$SO_2$—$C_{1-4}$ alkyl, (m) —O—$(CH_2)_n$—$NR^8$—$SO_2$— (optionally halogenated $C_{1-4}$ alkyl), (n) —CO—$NR^8$—$(CH_2)_n$—OH, (o) —CO—$NR^8$—$(CH_2)_n$—$SO_2$— (optionally halogenated $C_{1-4}$ alkyl), (p) —CO—$NR^8$—O—$C_{1-4}$ alkyl, (q) —$NR^6R^7$, (r) —$NR^8$—$(CH_2)_n$—OH, (s) —$NR^8$—$(CH_2)_n$—$SO_2$—$C_{1-4}$ alkyl, (t) —$NR^8$—CO— (optionally halogenated $C_{1-4}$ alkyl), (u) —$NR^8$—CO—$(CH_2)_n$—OH (wherein $(CH_2)_n$ is optionally substituted by optionally halogenated $C_{1-4}$ alkyl or hydroxy), (v) —$NR^8$—CO—$(CH_2)_n$—CN, (w) —$NR^8$—CO—$(CH_2)_n$—$NR^6R^7$ (when n is not less than 2, a subset —$CH_2CH_2$— of $(CH_2)_n$ is optionally replaced by —CH=CH—), (x) —$NR^8$—CO—$(CH_2)_n$—O—$C_{1-4}$ alkyl, (y) —$NR^8$—CO—$(CH_2)_n$—SO— (optionally halogenated $C_{1-4}$ alkyl), (z) —$NR^8$—CO—$(CH_2)_n$—$SO_2$— (optionally halogenated $C_{1-4}$ alkyl)

(wherein $(CH_2)_n$ is optionally substituted by $C_{1-4}$ alkyl), (aa) —$NR^8$—CO—$(CH_2)_n$—$SO_2$—$C_{3-8}$ cycloalkyl, (bb) —$NR^8$—CO—$(CH_2)_n$—$NR^8$—$SO_2$—$C_{1-4}$ alkyl, (cc) —$NR^8$—$CO_2$—$(CH_2)_n$—$SO_2$—$C_{1-4}$ alkyl, (dd) —$NR^8$—CO—NH—$(CH_2)_n$—$SO_2$—$C_{1-4}$ alkyl, (ee) —$NR^8$—CO—NH—O—$C_{1-4}$ alkyl, (ff) —$NR^8$—CO—NH—$(CH_2)_n$—O—$C_{1-4}$ alkyl, (gg) —$NR^8$—C(=NH)—NH—$C_{1-4}$ alkyl, (hh) —$NR^8$—$SO_2$—$(CH_2)_n$—$SO_2$—$C_{1-4}$ alkyl, (ii) —S—$(CH_2)_n$—OH, (jj) —SO—$(CH_2)_n$—OH, (kk) —$SO_2$—$(CH_2)_n$—OH, and (ll) —$NR^8$—CO— (optionally substituted heterocyclic group)

(preferably, said heterocyclic group is a 5- to 8-membered heterocyclic group having 1 to 3 hetero atoms selected from a nitrogen atom, an oxygen atom and an optionally oxidized sulfur atom, which is optionally substituted by substituent(s) selected from hydroxy, $C_{1-4}$ alkyl, optionally oxidized $C_{1-4}$ alkylthio, —CO—$C_{1-4}$ alkyl, —CO—O—$C_{1-4}$ alkyl, —CO—NH—$C_{1-4}$ alkyl, —$CONH_2$, —$SO_2$—$C_{1-4}$ alkyl, —$SO_2$—NH—$C_{1-4}$ alkyl, —$SO_2NH_2$ and the like), wherein n is an integer of 1 to 4, $R^6$ and $R^7$ are the same or different and each is a hydrogen atom or a $C_{1-4}$ alkyl group, and $R^8$ is a hydrogen atom or a $C_{1-4}$ alkyl group.

[Compound (Ij)]

A compound (I) wherein

A is a $C_{6-18}$ aryl group substituted by substituent(s) selected from (i) a phenyloxy group substituted by 1 to 5 substituents selected from (a) halogen, (b) optionally halogenated $C_{1-4}$ alkyl, (c) hydroxy-$C_{1-4}$ alkyl, (d) heterocyclyl-$C_{1-4}$ alkyl (preferably, 5- to 8-membered heterocyclyl-$C_{1-4}$ alkyl, said 5- to 8-membered heterocyclyl has 1 to 3 hetero atoms selected from a nitrogen atom, an oxygen atom and an optionally oxidized sulfur atom, such as imidazolyl and the like), (e) optionally halogenated $C_{1-4}$ alkyloxy, (f) cyano, (g) carbamoyl optionally substituted by $C_{1-6}$ alkyl, and (h) $C_{1-4}$ alkoxy-carbonyl, (ii) a phenyl-$C_{1-3}$ alkyloxy group substituted by 1 to 5 substituents selected from (a) halogen, (b) optionally halogenated $C_{1-4}$ alkyl, (c) hydroxy-$C_{1-4}$ alkyl, (d) heterocyclyl-$C_{1-4}$ alkyl (preferably, 5- to 8-membered heterocyclyl-$C_{1-4}$ alkyl, said 5- to 8-membered heterocyclyl has 1 to 3 hetero atoms selected from a nitrogen atom, an oxygen atom and an optionally oxidized sulfur atom, such as imidazolyl and the like), (e) optionally halogenated $C_{1-4}$ alkyloxy, (f) cyano, (g) carbamoyl optionally substituted by $C_{1-8}$ alkyl, and (h) $C_{1-4}$ alkoxy-carbonyl, (iii) a 5- to 8-membered heterocyclyloxy group containing 1 to 3 hetero atoms selected from a nitrogen atom, an oxygen atom and a sulfur atom, which is substituted by 1 to 5 substituents selected from (a) halogen, (b) optionally halogenated $C_{1-4}$ alkyl, (c) hydroxy-$C_{1-4}$ alkyl, (d) heterocyclyl-$C_{1-4}$ alkyl (preferably, 5- to 8-membered heterocyclyl-$C_{1-4}$ alkyl, said 5- to 8-membered heterocyclyl has 1 to 3 hetero atoms selected from a nitrogen atom, an oxygen atom and an optionally oxidized sulfur atom, such as imidazolyl and the like), (e) optionally halogenated $C_{1-4}$ alkyloxy, (f) cyano, (g) carbamoyl optionally substituted by $C_{1-8}$ alkyl, and (h) $C_{1-4}$ alkoxy-carbonyl, and (iv) 5- to 8-membered heterocyclyl-$C_{1-3}$ alkyloxy containing 1 to 3 hetero atoms selected from a nitrogen atom, an oxygen atom and a sulfur atom, which is substituted by 1 to 5 substituents selected from (a) halogen, (b) optionally halogenated $C_{1-4}$ alkyl, (c) hydroxy-$C_{1-4}$ alkyl, (d) heterocyclyl-$C_{1-4}$ alkyl (preferably, 5- to 8-membered heterocyclyl-$C_{1-4}$ alkyl, said 5- to 8-membered heterocyclyl has 1 to 3 hetero atoms selected from a nitrogen atom, an oxygen atom and an optionally oxidized sulfur atom, such as imidazolyl and the like), (e) optionally halogenated $C_{1-4}$ alkyloxy, (f) cyano, (g) carbamoyl optionally substituted by $C_{1-8}$ alkyl, and (h) $C_{1-4}$ alkoxy-carbonyl;

wherein the $C_{6-18}$ aryl group is optionally further substituted by 1 to 4 substituents selected from halogen and optionally halogenated $C_{1-4}$ alkyl;

$R^1$ is a hydrogen atom;

$R^2$ is a $C_{1-8}$ alkyl group, a $C_{2-8}$ alkenyl group or a $C_{2-8}$ alkynyl group, each of which is substituted by substituent(s) selected from (a) hydroxy, (b) optionally halogenated $C_{1-4}$ alkyloxy, (c) —O—$(CH_2)_n$—OH, (d) —O—$(CH_2)_n$—O—CO—$NH_2$, (e) —O—$(CH_2)_n$—O—$C_{1-4}$ alkyl, (f) —O—$(CH_2)_n$—$SO_2$— (optionally halogenated $C_{1-4}$ alkyl), (g) —O—$(CH_2)_n$—$SO_2$—$C_{6-18}$ aryl, (h) —O—$(CH_2)_n$—$SO_2$—$(CH_2)_n$—OH, (i) —O—$(CH_2)_n$—$NR^8$—$SO_2$— (optionally halogenated $C_{1-4}$ alkyl), (j) —CO—$NR^8$—$(CH_2)_n$—OH, (k) —CO—$NR^8$—$(CH_2)_n$—$SO_2$— (optionally halogenated $C_{1-4}$ alkyl), (l) —$NR^6R^7$, (m) —$NR^8$—$(CH_2)_n$—OH, (n) —$NR^8$—$(CH_2)_n$—$SO_2$—$C_{1-4}$ alkyl, (o) —$NR^8$—CO—$(CH_2)_n$—OH, (p) —$NR^8$—CO—$(CH_2)_n$—O—$C_{1-4}$ alkyl, (q) —$NR^8$—CO—$(CH_2)_n$—SO— (optionally halogenated $C_{1-4}$ alkyl), (r) —$NR^8$—CO—$(CH_2)_n$—$SO_2$— (optionally halogenated $C_{1-4}$ alkyl), (s) —$NR^8$—CO—$(CH_2)_n$—$SO_2$—$C_{3-8}$ cycloalkyl, (t) —$NR^8$—$CO_2$—$(CH_2)_n$—$SO_2$—$C_{1-4}$ alkyl, (u) —$NR^8$—CO—NH—$(CH_2)_n$—$SO_2$—$C_{1-4}$ alkyl, (v) —$NR^8$—$SO_2$—$(CH_2)_n$—$SO_2$—$C_{1-4}$ alkyl, (w) —S—$(CH_2)_n$—OH, (x) —SO—$(CH_2)_n$—OH, (y) —$SO_2$—$(CH_2)_n$—OH, and (z) —$NR^8$—CO— (optionally substituted heterocyclic group)

(preferably, said heterocyclic group is a 5- to 8-membered heterocyclic group having 1 to 3 hetero atoms selected from a nitrogen atom, an oxygen atom and an optionally oxidized sulfur atom, which is optionally substituted by substituent(s) selected from hydroxy, $C_{1-4}$ alkyl, optionally oxidized $C_{1-4}$ alkylthio, —CO—$C_{1-4}$ alkyl, —CO—NH—$C_{1-4}$ alkyl, —$CONH_2$, —$SO_2$—$C_{1-4}$ alkyl, —$SO_2$—NH—$C_{1-4}$ alkyl, —$SO_2NH_2$ and the like), wherein n is an integer of 1 to 4, $R^6$ and $R^7$ are the same or different and each is a hydrogen atom or a $C_{1-4}$ alkyl group, $R^8$ is a hydrogen atom or a $C_{1-4}$ alkyl group, and $(CH_2)_n$ is optionally substituted by $C_{1-4}$ alkyl or hydroxy;

$R^3$ is a hydrogen atom or a $C_{1-6}$ alkyl group; or $R^1$ and $R^2$ are optionally bonded to form

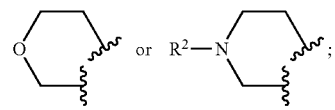

or $R^2$ and $R^3$ are optionally bonded to form $C_{2-4}$ alkylene.

Particularly preferably, $R^2$ is a $C_{1-8}$ alkyl group, a $C_{2-8}$ alkenyl group or a $C_{2-8}$ alkynyl group (particularly, a $C_{1-8}$ alkyl group), each of which is substituted by substituent(s) selected from (a) hydroxy, (b) optionally halogenated $C_{1-4}$ alkyloxy, (c) —O—$(CH_2)_n$—OH (wherein $(CH_2)_n$ is optionally substituted by hydroxy), (d) —O—$(CH_2)_n$—O—CO—$NH_2$, (e) —O—$(CH_2)_n$—O—$C_{1-4}$ alkyl, (f) —O—$(CH_2)_n$—$SO_2$— (optionally halogenated $C_{1-4}$ alkyl), (g) —O—$(CH_2)_n$—$SO_2$—$C_{6-18}$ aryl, (h) —O—$(CH_2)_n$—$SO_2$—$(CH_2)_n$—OH, (i) —O—$(CH_2)_n$—$NR^8$—$SO_2$— (optionally halogenated $C_{1-4}$ alkyl), (j) —CO—$NR^8$—$(CH_2)_n$—OH, (k) —CO—$NR^8$—$(CH_2)_n$—$SO_2$— (optionally halogenated $C_{1-4}$ alkyl), (l) —$NR^6R^7$, (m) —$NR^8$—$(CH_2)_n$—OH, (n) —$NR^8$—$(CH_2)_n$—$SO_2$—$C_{1-4}$ alkyl, (o) —$NR^8$—CO—$(CH_2)_n$—OH (wherein $(CH_2)_n$ is optionally substituted by $C_{1-4}$ alkyl), (p) —$NR^8$—CO—$(CH_2)_n$—O—$C_{1-4}$ alkyl, (q) —$NR^8$—CO—$(CH_2)_n$—SO— (optionally halogenated $C_{1-4}$ alkyl), (r) —$NR^8$—CO—$(CH_2)_n$—$SO_2$— (optionally halogenated $C_{1-4}$ alkyl)

(wherein $(CH_2)_n$ is optionally substituted by $C_{1-4}$ alkyl), (s) —$NR^8$—CO—$(CH_2)_n$—$SO_2$—$C_{3-8}$ cycloalkyl, (t) —$NR^8$—$CO_2$—$(CH_2)_n$—$SO_2$—$C_{1-4}$ alkyl, (u) —$NR^8$—CO—NH—$(CH_2)_n$—$SO_2$—$C_{1-4}$ alkyl, (v) —$NR^8$—$SO_2$—$(CH_2)_n$—$SO_2$—$C_{1-4}$ alkyl, (w) —S—$(CH_2)_n$—OH, (x) —SO—$(CH_2)_n$—OH, (y) —$SO_2$—$(CH_2)_n$—OH, and (z) —$NR^8$—CO— (optionally substituted heterocyclic group)

(preferably, said heterocyclic group is a 5- to 8-membered heterocyclic group having 1 to 3 hetero atoms selected from a nitrogen atom, an oxygen atom and an optionally oxidized sulfur atom, which is optionally substituted by substituent(s) selected from hydroxy, $C_{1-4}$ alkyl, optionally oxidized $C_{1-4}$ alkylthio, —CO—$C_{1-4}$ alkyl, —CO—NH—$C_{1-4}$ alkyl, —$CONH_2$, —$SO_2$—$C_{1-4}$ alkyl, —$SO_2$—NH—$C_{1-4}$ alkyl, —$SO_2NH_2$ and the like), wherein n is an integer of 1 to 4, $R^6$ and $R^7$ are the same or different and each is a hydrogen atom or a $C_{1-4}$ alkyl group, and $R^8$ is a hydrogen atom or a $C_{1-4}$ alkyl group, and the like is preferable.

[Compound (Ik)]

A compound (I) wherein $R^2$ is (i) a $C_{5-8}$ alkyl group substituted by hydroxy, (ii) a $C_{1-8}$ alkyl group substituted by substituent(s) selected from (a) halogenated $C_{1-4}$ alkyloxy, (b) —O—$(CH_2)_n$—OH, (c) —O—$(CH_2)_n$—O—CO—$NH_2$, (d) —O—$(CH_2)_n$—O— (optionally halogenated $C_{1-4}$ alkyl), (e) —O—$(CH_2)_n$—$SO_2$— (optionally halogenated $C_{1-4}$ alkyl), (f) —O—$(CH_2)_n$—$SO_2$—$C_{6-18}$ aryl, (g) —O—$(CH_2)_n$—$NR^8$—$SO_2$— (optionally halogenated $C_{1-4}$ alkyl), (h) —CO—$NR^8$—$(CH_2)_n$—OH, (i) —CO—$NR^8$—$(CH_2)_n$—$SO_2$— (optionally halogenated $C_{1-4}$ alkyl), (j) —$NR^8$—$(CH_2)_n$—$SO_2$—$C_{1-4}$ alkyl, (k) —$NR^8$—CO—$(CH_2)_n$—OH, (l) —$NR^8$—CO—$(CH_2)_n$—O—$C_{1-4}$ alkyl, (m) —$NR^8$—CO—$(CH_2)_n$—SO— (optionally halogenated $C_{1-4}$ alkyl), (n) —$NR^8$—CO—$(CH_2)_n$—$SO_2$— (optionally halogenated $C_{1-4}$ alkyl), (o) —$NR^8$—CO—$(CH_2)_n$—$SO_2$—$C_{3-8}$ cycloalkyl, (p) —$NR^8$—$CO_2$—$(CH_2)_n$—$SO_2$—$C_{1-4}$ alkyl, (q) —$NR^8$—CO—NH—$(CH_2)_n$—$SO_2$—$C_{1-4}$ alkyl, (r) —$NR^8$—$SO_2$—$(CH_2)_n$—$SO_2$—$C_{1-4}$ alkyl, (s) —S—$(CH_2)_n$—OH, (t) —SO—$(CH_2)_n$—OH, (u) —$SO_2$—$(CH_2)_n$—OH, and (v) —$NR^8$—CO— (optionally substituted heterocyclic group)

(preferably, said heterocyclic group is a 5- to 8-membered heterocyclic group having 1 to 3 hetero atoms selected from a nitrogen atom, an oxygen atom and an optionally oxidized sulfur atom, which is optionally substituted by substituent(s) selected from hydroxy, $C_{1-4}$ alkyl, optionally oxidized $C_{1-4}$ alkylthio, —CO—$C_{1-4}$ alkyl, —CO—NH—$C_{1-4}$ alkyl, —$CONH_2$, —$SO_2$—$C_{1-4}$ alkyl, —$SO_2$—NH—$C_{1-4}$ alkyl, —$SO_2NH_2$ and the like), wherein n is an integer of 1 to 4, $R^8$ is a hydrogen atom or a $C_{1-4}$ alkyl group, and $(CH_2)_n$ is optionally substituted by $C_{1-4}$ alkyl, (iii) a $C_{2-8}$ alkenyl group optionally substituted by hydroxy, or (iv) a $C_{2-8}$ alkynyl group optionally substituted by hydroxy.

Particularly preferably, $R^2$ is (i) a $C_{5-8}$ alkyl group substituted by hydroxy, (ii) a $C_{1-8}$ alkyl group substituted by substituent(s) selected from (a) halogenated $C_{1-4}$ alkyloxy, (b) —O—$(CH_2)_n$—OH (wherein $(CH_2)_n$ is optionally substituted by hydroxy), (c) —O—$(CH_2)_n$—O—CO—$NH_2$, (d) —O—$(CH_2)_n$—O— (optionally halogenated $C_{1-4}$ alkyl), (e) —O—$(CH_2)_n$—$SO_2$— (optionally halogenated $C_{1-4}$ alkyl), (f) —O—$(CH_2)_n$—$SO_2$—$C_{6-18}$ aryl, (g) —O—$(CH_2)_n$—$NR^8$—$SO_2$— (optionally halogenated $C_{1-4}$ alkyl), (h) —CO—$NR^8$—$(CH_2)_n$—OH, (i) —CO—$NR^8$—$(CH_2)_n$—$SO_2$— (optionally halogenated $C_{1-4}$ alkyl), (j) —$NR^8$—$(CH_2)_n$—$SO_2$—$C_{1-4}$ alkyl, (k) —$NR^8$—CO—$(CH_2)_n$—OH (wherein $(CH_2)_n$ is optionally substituted by $C_{1-4}$ alkyl), (l) —$NR^8$—CO—$(CH_2)_n$—O—$C_{1-4}$ alkyl, (m) —$NR^8$—CO—$(CH_2)_n$—SO— (optionally halogenated $C_{1-4}$ alkyl), (n) —$NR^8$—CO—$(CH_2)_n$—$SO_2$— (optionally halogenated $C_{1-4}$ alkyl)

(wherein $(CH_2)_n$ is optionally substituted by $C_{1-4}$ alkyl), (o) —$NR^8$—CO—$(CH_2)_n$—$SO_2$—$C_{3-8}$ cycloalkyl, (p) —$NR^8$—$CO_2$—$(CH_2)_n$—$SO_2$—$C_{1-4}$ alkyl, (q) —$NR^8$—CO—NH—$(CH_2)_n$—$SO_2$—$C_{1-4}$ alkyl, (r) —$NR^8$—$SO_2$—$(CH_2)_n$—$SO_2$—$C_{1-4}$ alkyl, (s) —S—$(CH_2)_n$—OH, (t) —SO—$(CH_2)_n$—OH, (u) —$SO_2$—$(CH_2)_n$—OH, and (v) —$NR^8$—CO— (optionally substituted heterocyclic group)

(preferably, said heterocyclic group is a 5- to 8-membered heterocyclic group having 1 to 3 hetero atoms selected from a nitrogen atom, an oxygen atom and an optionally oxidized sulfur atom, which is optionally substituted by substituent(s) selected from hydroxy, $C_{1-4}$ alkyl, optionally oxidized $C_{1-4}$ alkylthio, —CO—$C_{1-4}$ alkyl, —CO—NH—$C_{1-4}$ alkyl, —CONH$_2$, —SO$_2$—$C_{1-4}$ alkyl, —SO$_2$—NH—$C_{1-4}$ alkyl, —SO$_2$NH$_2$ and the like), wherein n is an integer of 1 to 4, and $R^8$ is a hydrogen atom or a $C_{1-4}$ alkyl group, (iii) a $C_{2-8}$ alkenyl group optionally substituted by hydroxy, or (iv) a $C_{2-8}$ alkynyl group optionally substituted by hydroxy.

As the salts of the compound (I), for example, metal salt, ammonium salt, salts with organic base, salts with inorganic acid, salts with organic acid, salts with basic or acidic amino acid and the like can be mentioned. As preferable examples of the metal salt, for example, alkali metal salts such as sodium salt, potassium salt and the like; alkaline earth metal salts such as calcium salt, magnesium salt, barium salt and the like; aluminum salt and the like can be mentioned. As preferable examples of the salts with organic base, for example, salts with trimethylamine, triethylamine, pyridine, picoline, 2,6-lutidine, ethanolamine, diethanolamine, triethanolamine, tromethamine [tris(hydroxymethyl)methylamine], t-butylamine, cyclohexylamine, dicyclohexylamine, N,N'-dibenzylethylenediamine and the like can be mentioned. As preferable examples of salts with inorganic acid, for example, salts with hydrochloric acid, hydrobromic acid, nitric acid, sulfuric acid, phosphoric acid and the like can be mentioned. As preferable examples of the salts with organic acid, for example, salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like can be mentioned. As preferable examples of the salts with basic amino acid, for example, salts with arginine, lysine, ornithine and the like can be mentioned, and as preferable examples of the salts with acidic amino acid, for example, salts with aspartic acid, glutamic acid and the like can be mentioned.

Of these, pharmaceutically acceptable salts are preferable. For example, when a compound contains an acidic functional group, inorganic salts such as alkali metal salts (e.g., sodium salt, potassium salt etc.), alkaline earth metal salts (e.g., calcium salt, magnesium salt, barium salt etc.) and the like, ammonium salt and the like, and when a compound contains a basic functional group, for example, salts with inorganic acid such as hydrochloric acid, hydrobromic acid, nitric acid, sulfuric acid, phosphoric acid and the like, or salts with organic acid such as acetic acid, phthalic acid, fumaric acid, oxalic acid, tartaric acid, maleic acid, citric acid, succinic acid, methanesulfonic acid, p-toluenesulfonic acid and the like can be mentioned.

As compound (I), preferred is a compound wherein A is an aryl group substituted by a group of the formula —$Y^2$—B and optionally further substituted, wherein $Y^2$ is a single bond, —O—, —OCH$_2$—, —NH— or —S—, and B is an aryl group, a heterocyclic group, a $C_{3-8}$ cycloalkyl group, a carbamoyl group, a ureido group, a $C_{6-18}$ aryl-carbonyl group or a $C_{6-18}$ aryl-$C_{1-4}$ alkyl-carbonyl group, each of which is optionally substituted.

As a preferable embodiment of compound (I), a compound wherein W is $C(R^1)$;

A is an aryl group substituted by a group of the formula —$Y^2$—B, and optionally further substituted, wherein $Y^2$ is a single bond, —O—, —OCH$_2$—, —NH— or —S—, and B is an aryl group, a heterocyclic group, a $C_{3-8}$ cycloalkyl group, a carbamoyl group, a ureido group, a $C_{6-18}$ aryl-carbonyl group or a $C_{6-18}$ aryl-$C_{1-4}$ alkyl-carbonyl group, each of which is optionally substituted;

$R^1$ is a hydrogen atom or a group of the formula —$X^2$—$R^4$ wherein $X^2$ is a single bond, —NH— or —O—, and $R^4$ is a hydrogen atom or a $C_{1-8}$ alkyl group, a $C_{2-8}$ alkenyl group, a $C_{2-8}$ alkynyl group, a carbamoyl group, a $C_{1-8}$ alkyl-carbonyl group, a $C_{3-8}$ cycloalkyl group, a $C_{6-18}$ aryl group, a $C_{6-18}$ aryl-$C_{1-4}$ alkyl group, a $C_{6-18}$ aryl-carbonyl group, a $C_{6-18}$ aryl-$C_{1-4}$ alkyl-carbonyl group, a heterocyclic group, a heterocyclyl-$C_{1-4}$ alkyl group, a heterocyclyl-carbonyl group or a heterocyclyl-$C_{1-4}$ alkyl-carbonyl group, each of which is optionally substituted;

$R^2$ is a hydrogen atom or a $C_{1-8}$ alkyl group, a $C_{2-8}$ alkenyl group, a $C_{2-8}$ alkynyl group, a carbamoyl group, a $C_{1-8}$ alkyl-carbonyl group, a $C_{1-8}$ alkyl-sulfonyl group, a $C_{3-8}$ cycloalkyl group, a $C_{6-18}$ aryl group, a $C_{6-18}$ aryl-$C_{1-4}$ alkyl group, a $C_{6-18}$ aryl-carbonyl group, a $C_{6-18}$ aryl-$C_{1-4}$ alkyl-carbonyl group, a $C_{6-18}$ aryl-sulfonyl group, a heterocyclic group, a heterocyclyl-$C_{1-4}$ alkyl group, a heterocyclyl-carbonyl group or a heterocyclyl-$C_{1-4}$ alkyl-carbonyl group, each of which is optionally substituted; and $X^1$ is —$NR^3$— wherein $R^3$ is a hydrogen atom or an optionally substituted aliphatic hydrocarbon group, can be mentioned.

As another preferably embodiment of compound (I), a compound wherein

W is N;

$X^1$ is —$NR^3$— wherein $R^3$ is a hydrogen atom or an optionally substituted aliphatic hydrocarbon group;

A is an aryl group substituted by a group of the formula —$Y^2$—B, and optionally further substituted, wherein $Y^2$ is a single bond, —O—, —OCH$_2$—, —NH— or —S—, and B is an aryl group, a heterocyclic group, a $C_{3-8}$ cycloalkyl group, a carbamoyl group, a ureido group, a $C_{6-18}$ aryl-carbonyl group or a $C_{6-18}$ aryl-$C_{1-4}$ alkyl-carbonyl group, each of which is optionally substituted;

$R^2$ is a hydrogen atom or a $C_{1-8}$ alkyl group, a $C_{2-8}$ alkenyl group, a $C_{2-8}$ alkynyl group, a carbamoyl group, a $C_{1-8}$ alkyl-carbonyl group, a $C_{1-8}$ alkyl-sulfonyl group, a $C_{3-8}$ cycloalkyl group, a $C_{6-18}$ aryl group, a $C_{6-18}$ aryl-$C_{1-4}$ alkyl group, a $C_{6-18}$ aryl-carbonyl group, a $C_{6-18}$ aryl-$C_{1-4}$ alkyl-carbonyl group, a $C_{6-18}$ aryl-sulfonyl group, a heterocyclic group, a heterocyclyl-$C_{1-4}$ alkyl group, a heterocyclyl-carbonyl group or a heterocyclyl-$C_{1-4}$ alkyl-carbonyl group, each of which is optionally substituted, can be mentioned.

As another preferable embodiment of compound (I), a compound wherein W is N;

$X^1$ is —$NR^3$—;

A is an aryl group substituted by a group of the formula —$Y^2$—B, and optionally further substituted, wherein $Y^2$ is a single bond, —O—, —OCH$_2$—, —NH— or —S—, and B is an aryl group, a heterocyclic group, a $C_{3-8}$ cycloalkyl group, a carbamoyl group, a ureido group, a $C_{6-18}$ aryl-carbonyl group or a $C_{6-18}$ aryl-$C_{1-4}$ alkyl-carbonyl group, each of which is optionally substituted;

and $R^2$ and $R^3$ are bonded to form an optionally substituted ring structure, can be mentioned.

As compound (I), (i) 2-{2-[4-({3-chloro-4-[(3-fluorobenzyl)oxy]phenyl}amino)-5H-pyrrolo[3,2-d]pyrimidin-5-yl]ethoxy}ethanol, (ii) 2-{2-[4-({3-chloro-4-[3-(trifluoromethyl)phenoxy]phenyl}amino)-5H-pyrrolo[3,2-d]pyrimidin-5-yl]ethoxy}ethanol, (iii) N-{2-[4-({3-chloro-4-[3-(trifluoromethyl)phenoxy]phenyl}amino)-5H-pyrrolo[3,2-d]pyrimidin-5-yl]ethyl}-3-hydroxy-3-methylbutanamide, (iv) N-{2-[4-({3-chloro-4-[3-(trifluoromethyl)phenoxy]phenyl}amino)-5H-pyrrolo[3,2-d]pyrimidin-5-yl]ethyl}-2-(methylsulfonyl)acetamide, (v) N-{2-[4-({3-chloro-4-[3-(trifluoromethyl)phenoxy]phenyl}amino)-5H-pyrrolo[3,2-d]pyrimidin-5-yl]ethyl}-2-methyl-2-(methylsulfonyl)propanamide, (vi) 5-{2-[2-(tert-butylsulfonyl)ethoxy]ethyl}-N-{3-chloro-4-[3-(trifluoromethyl)phenoxy]phenyl}-5H-pyrrolo[3,2-d]pyrimidin-4-amine, (vii) 2-(methylsulfonyl)-N-{2-[4-({3-methyl-4-[3-(trifluoromethoxy)phenoxy]phenyl}amino)-5H-pyrrolo[3,2-d]pyrimidin-5-yl]ethyl}acetamide, (viii) N-[2-(4-{[3-chloro-4-(3-chlorophenoxy)phenyl]amino}-5H-pyrrolo[3,2-d]pyrimidin-5-yl)ethyl]-2-(methylsulfonyl)acetamide, and (ix) N-{2-[4-({3-chloro-4-[3-(trifluoromethoxy)phenoxy]phenyl}amino)-5H-pyrrolo[3,2-d]pyrimidin-5-yl]ethyl}-2-(methylsulfonyl)acetamide and the like are preferable. Particularly, N-{2-[4-({3-chloro-4-[3-(trifluoromethyl)phenoxy]phenyl}amino)-5H-pyrrolo[3,2-d]pyrimidin-5-yl]ethyl}-3-hydroxy-3-methylbutanamide is preferable.

Compound (I) and a salt thereof can be produced according to the method described in WO2005/118588.

When compound (I) has isomers such as optical isomer, stereoisomer, positional isomer, rotational isomer and the like, and any isomers and mixtures are encompassed in the compound (I). For example, when compound (I) has an optical isomer, an optical isomer separated from a racemate is also encompassed in the compound (I). These isomers can be obtained as independent products by a synthesis means or a separation means (concentration, solvent extraction, column chromatography, recrystallization and the like) known per se.

The compound (I) may be a crystal, and both a single crystal and crystal mixtures are encompassed in the compound (I). Crystals can be produced by crystallization according to crystallization methods known per se.

The compound (I) may be a solvate (e.g., hydrate etc.) or a non-solvate, both of which are encompassed in the compound (I).

A compound labeled with an isotope (e.g., $^3$H, $^{14}$C, $^{35}$S, $^{125}$I and the like) is also encompassed in the compound (I).

A prodrug of the compound (I) or a salt thereof (hereinafter referred to as compound (I)) means a compound which is converted to the compound (I) with a reaction due to an enzyme, an gastric acid, etc. under the physiological condition in the living body, that is, a compound which is converted to the compound (I) with oxidation, reduction, hydrolysis, etc. according to an enzyme; a compound which is converted to the compound (I) by hydrolysis etc. due to gastric acid, etc. A prodrug for compound (I) may be a compound obtained by subjecting an amino group in compound (I) to an acylation, alkylation or phosphorylation (e.g., a compound obtained by subjecting an amino group in compound (I) to an eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation and tert-butylation, etc.); a compound obtained by subjecting a hydroxy group in compound (I) to an acylation, alkylation, phosphorylation or boration (e.g., a compound obtained by subjecting an hydroxy group in compound (I) to an acetylation, palmitoylation, propanoylation, pivaloylation, succinylation, fumarylation, alanylation, dimethylaminomethylcarbonylation, etc.); a compound obtained by subjecting a carboxyl group in compound (I) to an esterification or amidation (e.g., a compound obtained by subjecting a carboxyl group in compound (I) to an ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification and methylamidation, etc.) and the like. Any of these compounds can be produced from compound (I) by a method known per se.

A prodrug for compound (I) may also be one which is converted into compound (I) under a physiological condition, such as those described in IYAKUHIN no KAIHATSU (Development of Pharmaceuticals), Vol. 7, Design of Molecules, p. 163-198, Published by HIROKAWA SHOTEN (1990).

The above-mentioned HER2 inhibitor has a tyrosine kinase inhibitory activity, and can be used for the prophylaxis or treatment of a tyrosine kinase dependent disease in a mammal, particularly for the prophylaxis or treatment of a tyrosine kinase dependent disease in patients coexpressing HER2 and HER3. Tyrosine kinase-dependent diseases include diseases characterized by increased cell proliferation due to abnormal tyrosine kinase enzyme activity. Furthermore, the compound of the present invention specifically inhibits HER2 kinase and/or EGFR kinase and is therefore also useful as a therapeutic agent for suppressing the growth of HER2 and/or EGFR kinase-expressing cancer, or a preventive agent for the transition of hormone-dependent cancer to hormone-independent cancer. In addition, the compound is useful as a pharmaceutical agent because it shows low toxicity (e.g., acute toxicity, chronic toxicity, genetic toxicity, reproductive toxicity, cardiotoxicity, drug interaction, carcinogenicity and the like), high water solubility, and is superior in stability, pharmacokinetics (absorption, distribution, metabolism, excretion and the like) and drug efficacy expression.

That is, a HER2 inhibitor is useful as a therapeutic agent for suppressing the growth of a cancer expressing HER2 and/or EGFR kinase in patients coexpressing HER2 and HER3, and also as a prophylactic agent for preventing the transfer of hormone dependent cancer to hormone independent cancer. In addition, having low toxicity (e.g., acute toxicity, chronic toxicity, genetic toxicity, reproductive toxicity, cardiotoxicity, drug interaction, carcinogenicity and the like), high water solubility, and being superior in the stability, pharmacokinetics (absorption, distribution, metabolism, excretion and the like) and drug efficacy expression, the HER2 inhibitor is useful as a pharmaceutical agent.

That is, the HER2 inhibitor can be used as a safe agent for the prophylaxis or treatment of a disease caused by abnormal cell growth such as various cancers (particularly breast cancer (e.g., invasive ductal carcinoma, ductal cancer in situ, inflammatory breast cancer, etc.), prostate cancer (e.g., hormone-dependent prostate cancer, hormone-independent prostate cancer, etc.), pancreatic cancer (e.g., pancreatic duct cancer, etc.), gastric cancer (e.g., papillary adenocarcinoma, mucinous adenocarcinoma, adenosquamous cancer, etc.), lung cancer (e.g., non-small cell lung cancer, small cell lung cancer, malignant mesothelioma, etc.), colon cancer (e.g., gastrointestinal stromal tumor, etc.), rectal cancer (e.g., gastrointestinal stromal tumor, etc.), colorectal cancer (e.g., familial colorectal cancer, hereditary nonpolyposis colorectal cancer, gastrointestinal stromal tumor, etc.), small intestinal cancer (e.g., non-Hodgkin lymphoma, gastrointestinal stromal tumor, etc.), esophagus cancer, duodenal cancer, cancer of tongue, cancer of pharynx (e.g., nasopharyngeal carcinoma, oropharyngeal carcinoma, hypopharyngeal carcinoma, etc.), salivary gland cancer, brain tumor (e.g., pineal astrocytoma, pilocytic astrocytoma, diffuse astrocytoma, anaplastic astrocytoma, etc.), schwannoma, liver cancer (e.g., primary liver cancer, extrahepatic bile duct cancer, etc.), kidney cancer (e.g., renal cell carcinoma, transitional cell cancer of renal pelvis and ureter, etc.), bile duct cancer, endometrial cancer, cancer of the uterine cervix, ovarian cancer (e.g., ovarian epithelial cancer, extragonadal germ cell tumor, ovarian germ cell tumor, ovarial low malignant potential tumor, etc.), urinary bladder cancer, urethral cancer, skin cancer (e.g., ocular melanoma, Merkel cell carcinoma, etc.), hemangioma, malignant lymphoma, malignant melanoma, thyroid cancer (e.g., medullary thyroid cancer, etc.), parathyroid cancer, nasal cancer, paranasal cancer, bone tumor (e.g., osteosarcoma, Ewing's tumor, uterus sarcoma, soft tissue sarcoma, etc.), vascular fibroma, retinoblastoma, penile cancer, testis tumor, solid cancer in childhood (e.g., Wilms' tumor, childhood kidney tumor, etc.), Kaposi's sarcoma, Kaposi's sarcoma derived from AIDS, maxillary sinus tumor, fibrous histiocytoma, leiomyosarcoma, rhabdomyosarcoma, leukemia (e.g., acute myeloid leukemia, acute lymphoblastic leukemia, etc.), etc.), atherosclerosis, angiogenesis (e.g., angiogenesis associated with growth of solid cancer or sarcoma, angiogenesis associated with tumor metastasis, and angiogenesis associated with diabetic retinopathy, etc.), viral disease (HIV infection, etc.) and the like in patients coexpressing HER2 and HER3.

The tyrosine kinase-dependent disease further includes cardiovascular diseases associated with abnormal tyrosine kinase enzyme activity. Accordingly, the HER2 inhibitor can also be used as an agent for the prophylaxis or treatment of cardiovascular diseases such as restenosis.

The HER2 inhibitor is useful as an anti-cancer agent for the prophylaxis or treatment of cancer patients coexpressing HER2 and HER3, particularly those having breast cancer, prostate cancer, lung cancer, pancreatic cancer, kidney cancer, colorectal cancer, small intestinal cancer, esophagus cancer, gastric cancer and the like.

HER2 inhibitor shows low toxicity and can be used as a pharmaceutical agent as it is, or as a pharmaceutical composition in admixture with a commonly known pharmaceutically acceptable carrier, etc. in mammals (e.g., humans, horses, bovines, dogs, cats, rats, mice, rabbits, pigs, monkeys, and the like).

For administration of the HER2 inhibitor of the present invention as a pharmaceutical agent for mammals such as humans, it can be administered orally in the form of, for example, tablets, capsules (including soft capsules and microcapsules), powders, granules and the like, or parenterally in the form of injections, suppositories, pellets and the like. Examples of the "parenteral administration" include intravenous administration, intramuscular administration, subcutaneous administration, intra-tissue administration, intranasal administration, intradermal administration, instillation administration, intracerebral administration, intrarectal administration, intravaginal administration, intraperitoneal administration, intratumoral administration, administration to the juxtaposition of tumor and administration directly to the lesion.

The dose of the HER2 inhibitor varies depending on the administration route, symptoms and the like. For example, when it is administered orally as an anticancer agent to a patient (body weight 40 to 80 kg) with breast cancer or prostate cancer, its dose is, for example, 0.5 to 100 mg/kg body weight per day, preferably 1 to 50 mg/kg body weight per day, and more preferably 1 to 25 mg/kg body weight per day. This amount may be administered once or in 2 or 3 divided portions daily.

The HER2 inhibitor can be safely administered orally or parenterally (e.g., topical, rectal, intravenous administrations, etc.) as a single agent, or a pharmaceutical composition containing a pharmacologically acceptable carrier such as tablet (including sugar-coated tablet, film-coated tablet), powder, granule, capsule, liquid, emulsion, suspension, injection, suppository, sustained release preparation, plaster and the like, according to a conventional method (e.g., a method described in the Japanese Pharmacopoeia, etc.).

Moreover, a combination of (1) administration of an effective amount of the HER2 inhibitor in the present invention and (2) 1 to 3 kinds selected from the group consisting of (i) administration of an effective amount of other anticancer agents, (ii) administration of an effective amount of hormonal therapeutic agents and (iii) non-drug therapy can prevent and/or treat cancer more effectively. The non-drug therapy is exemplified by surgery, radiotherapy, gene therapy, thermotherapy, cryotherapy, laser cauterization, and the like, and two or more of these may be combined.

In the present specification, as examples of the "hormonal therapeutic agents" there may be mentioned fosfestrol, diethylstylbestrol, chlorotrianisene, medroxyprogesterone acetate, megestrol acetate, chlormadinone acetate, cyproterone acetate, danazol, dienogest, asoprisnil, allylestrenol, gestrinone, nomegestrol, Tadenan, mepartricin, raloxifene, ormeloxifene, levormeloxifene, anti-estrogens (e.g., tamoxifen citrate, toremifene citrate, and the like), ER down-regulator (e.g., fulvestrant and the like), human menopausal gonadotrophin, follicle stimulating hormone, pill preparations, mepitiostane, testrolactone, aminoglutethimide, LH-RH agonists (e.g., goserelin acetate, buserelin, leuprorelin, and the like), droloxifene, epitiostanol, ethinylestradiol sulfonate, aromatase inhibitors (e.g., fadrozole hydrochloride, anastrozole, retrozole, exemestane, vorozole, formestane, and the like), anti-androgens (e.g., flutamide, bicartamide, nilutamide, and the like), 5α-reductase inhibitors (e.g., finasteride, dutasteride, epristeride, and the like), adrenocortichormone drugs (e.g., dexamethasone, prednisolone, betamethasone, triamcinolone, and the like), androgen synthesis inhibitors (e.g., abiraterone, and the like), and retinoid and drugs that retard retinoid metabolism (e.g., liarozole, and the like), etc. and LH-RH agonists (e.g., goserelin acetate, buserelin, leuprorelin) are preferable.

In the present specification, as the "anti-cancer agent", for example, chemotherapeutic agent, immunotherapeutic agent, a pharmaceutical agent that inhibits the action of cell growth factor and a receptor thereof and the like can be mentioned.

As examples of said "chemotherapeutic agents", there may be mentioned alkylating agents, antimetabolites, anticancer antibiotics, plant-derived anticancer agents, and the like.

As examples of "alkylating agents", there may be mentioned nitrogen mustard, nitrogen mustard-N-oxide hydrochloride, chlorambutyl, cyclophosphamide, ifosfamide, thiotepa, carboquone, improsulfan tosylate, busulfan, nimustine hydrochloride, mitobronitol, melphalan, dacarbazine, ranimustine, sodium estramustine phosphate, triethylenemelamine, carmustine, lomustine, streptozocin, pipobroman, etoglucid, carboplatin, cisplatin, miboplatin, nedaplatin, oxaliplatin, altretamine, ambamustine, dibrospidium hydrochloride, fotemustine, prednimustine, pumitepa, ribomustin, temozolomide, treosulphan, trophosphamide, zinostatin stimalamer, adozelesin, cystemustine, bizelesin, and the like.

As examples of "antimetabolites", there may be mentioned mercaptopurine, 6-mercaptopurine riboside, thioinosine, methotrexate, enocitabine, cytarabine, cytarabine ocfosfate, ancitabine hydrochloride, 5-FU drugs (e.g., fluorouracil, tegafur, UFT, doxifluridine, carmofur, gallocitabine, emitefur, and the like), aminopterine, leucovorin calcium, tabloid, butocine, folinate calcium, levofolinate calcium, cladribine, emitefur, fludarabine, gemcitabine, hydroxycarbamide, pentostatin, piritrexim, idoxuridine, mitoguazone, thiazophrine, ambamustine and the like.

As examples of "anticancer antibiotics", there may be mentioned actinomycin-D, actinomycin-C, mitomycin-C, chromomycin-A3, bleomycin hydrochloride, bleomycin sulfate, peplomycin sulfate, daunorubicin hydrochloride, doxorubicin hydrochloride, aclarubicin hydrochloride, pirarubicin hydrochloride, epirubicin hydrochloride, neocarzinostatin, mithramycin, sarcomycin, carzinophilin, mitotane, zorubicin hydrochloride, mitoxantrone hydrochloride, idarubicin hydrochloride, and the like.

As examples of "plant-derived anticancer agents", there may be mentioned etoposide, etoposide phosphate, vinblastine sulfate, vincristine sulfate, vindesine sulfate, teniposide, paclitaxel (Taxol (trademark)), docetaxel, vinorelbine, and the like.

As examples of said "immunotherapeutic agents (BRM)", there may be mentioned picibanil, krestin, sizofuran, lentinan, ubenimex, interferons, interleukins, macrophage colony-stimulating factor, granulocyte colony-stimulating factor, erythropoietin, lymphotoxin, BCG vaccine, *Corynebacterium parvum*, levamisole, polysaccharide K, procodazole, and the like.

As the "cell growth factor" in said "pharmaceutical agents inhibiting the action of cell growth factors or cell growth factor receptors", there may be mentioned any substances that promote cell proliferation, which are normally peptides having a molecular weight of not more than 20,000 that are capable of exhibiting their activity at low concentrations by binding to a receptor, including (1) EGF (epidermal growth factor) or substances possessing substantially the same activity as it [e.g., EGF, heregulin, and the like], (2) insulin or substances possessing substantially the same activity as it [e.g., insulin, IGF (insulin-like growth factor)-1, IGF-2, and the like], (3) FGF (fibroblast growth factor) or substances possessing substantially the same activity as it [e.g., acidic FGF, basic FGF, KGF (keratinocyte growth factor), FGF-10, and the like], (4) other cell growth factors [e.g., CSF (colony stimulating factor), EPO (erythropoietin), IL-2 (interleukin-2), NGF (nerve growth factor), PDGF (platelet-derived growth factor), TGFβ (transforming growth factor β), HGF (hepatocyte growth factor), VEGF (vascular endothelial growth factor), and the like], and the like.

As examples of said "cell growth factor receptors", there may be mentioned any receptors capable of binding to the aforementioned cell growth factors, including EGF receptor, heregulin receptor (HER2), insulin receptor, IGF receptor, FGF receptor-1 or FGF receptor-2, and the like.

As examples of said "pharmaceutical agent that inhibits the action of cell growth factor", HER2 antibody (trastuzumab (Herceptin (trademark)) etc.), imatinib mesylate, ZD1839 or EGFR antibody (cetuximab (Erbitux (trademark)) etc.), antibody to VEGF (e.g., bevacizumab (Avastin (trademark))), VEGFR antibody, VEGFR inhibitor, EGFR inhibitor (erlotinib (Tarceva (trademark)), gefitinib (Iressa (trademark)) etc.) can be mentioned.

In addition to the aforementioned drugs, L-asparaginase, aceglatone, procarbazine hydrochloride, protoporphyrin-cobalt complex salt, mercuric hematoporphyrin-sodium, topoisomerase I inhibitors (e.g., irinotecan, topotecan, and the like), topoisomerase II inhibitors (e.g., sobuzoxane, and the like), differentiation inducers (e.g., retinoid, vitamin D, and the like), angiogenesis inhibitors (e.g., thalidomide, SU11248, and the like), α-blockers (e.g., tamsulosin hydrochloride, naftopidil, urapidil, alfuzosin, terazosin, prazosin, silodosin, and the like) serine/threonine kinase inhibitor, endothelin receptor antagonist (e.g., atrasentan, and the like), proteasome inhibitor (e.g., bortezomib, and the like), Hsp 90 inhibitor (e.g., 17-AAG, and the like), spironolactone, minoxidil, 11α-hydroxyprogesterone, bone resorption inhibiting/metastasis suppressing agent (e.g., zoledronic acid, alendronic acid, pamidronic acid, etidronic acid, ibandronic acid, clodronic acid) and the like can be used.

Of those mentioned above, a hormonal therapeutic agent or anti-cancer agent (hereinafter to be abbreviated as a concomitant drug), HER2 antibody (trastuzumab (Herceptin (trademark)) etc.), EGFR antibody (cetuximab (Erbitux (trademark)) etc.), EGFR inhibitor (erlotinib (Tarceva (trademark)), gefitinib (Iressa (trademark)) etc.), VEGFR inhibitor or a chemotherapeutic agent (paclitaxel (Taxol (trade name) etc.) is preferable.

Particularly, trastuzumab (Herceptin (trademark)), cetuximab (Erbitux (trademark)), erlotinib (Tarceva (trademark)), gefitinib (Iressa (trademark)), paclitaxel (Taxol (trademark)) and the like are preferable.

When (1) a HER2 inhibitor and (2) a concomitant drug are used in combination, the administration time of the HER2 inhibitor and the concomitant drug is not restricted, and the HER2 inhibitor and the concomitant drug can be administered to an administration subject simultaneously, or may be administered at staggered times. The dosage of the concomitant drug may be determined according to the dose clinically used, and can be appropriately selected depending on an administration subject, administration route, disease, combination and the like.

The administration mode of the HER2 inhibitor and the concomitant drug is not particularly restricted, and it is sufficient that the HER2 inhibitor and the concomitant drug are combined in administration. Examples of such administration mode include the following methods:

(1) The HER2 inhibitor and the concomitant drug are simultaneously produced to give a single preparation which is administered. (2) The HER2 inhibitor and the concomitant drug are separately produced to give two kinds of preparations which are administered simultaneously by the same administration route. (3) The HER2 inhibitor and the concomitant drug are separately produced to give two kinds of preparations which are administered by the same administration route only at the different times. (4) The HER2 inhibitor and the concomitant drug are separately produced to give two kinds of preparations which are administered simultaneously by different administration routes. (5) The HER2 inhibitor and the concomitant drug are separately produced to give two kinds of preparations which are administered by different administration routes at different times (e.g., the compound of the present invention and the concomitant drug are administered in this order, or in the reverse order).

A combination of a HER2 inhibitor and a concomitant drug is useful as a therapeutic agent suppressing growth of cancer expressing HER2 and/or EGFR kinase, and as an agent for preventing hormone dependent cancer and hormone dependent cancer from transferring to hormone independent cancer. In addition, the combination drug is useful as a pharmaceutical agent since it shows low toxicity (e.g., acute toxicity, chronic toxicity, genetic toxicity, reproductive toxicity, cardiotoxicity, drug interaction, carcinogenicity and the like), high water solubility, and superior stability, pharmacokinetics (absorption, distribution, metabolism, excretion and the like) and drug efficacy expression.

That is, a combination of a HER2 inhibitor and a concomitant drug can be used as a safe agent for the prophylaxis or treatment of diseases due to abnormal cell proliferation such as various cancers (particularly, breast cancer (e.g., invasive ductal carcinoma, ductal cancer in situ, inflammatory breast cancer etc.), prostate cancer (e.g., hormone-dependent prostate cancer, hormone-independent prostate cancer etc.), pancreatic cancer (e.g., pancreatic duct cancer etc.), gastric cancer (e.g., papillary adenocarcinoma, mucinous adenocarcinoma, adenosquamous carcinoma etc.), lung cancer (e.g., non-small cell lung cancer, small cell lung cancer, malignant mesothelioma etc.), colon cancer (e.g., gastrointestinal stromal tumor etc.), rectal cancer (e.g., gastrointestinal stromal tumor etc.), colorectal cancer (e.g., familial colorectal cancer, hereditary nonpolyposis colorectal cancer, gastrointestinal stromal tumor etc.), small intestinal cancer (e.g., non-Hodgkin lymphoma, gastrointestinal stromal tumor, etc.), esophagus cancer, duodenal cancer, cancer of tongue, cancer of pharynx (e.g., nasopharyngeal carcinoma, oropharyngeal carcinoma, hypopharyngeal carcinoma etc.), salivary gland cancer, brain tumor (e.g., pineal astrocytoma, pilocytic astrocytoma, diffuse astrocytoma, anaplastic astrocytoma etc.), schwannoma, liver cancer (e.g., primary liver cancer, extrahepatic bile duct cancer etc.), kidney cancer (e.g., renal cell carcinoma, transitional cell cancer of renal pelvis and ureter etc.), bile duct cancer, endometrial cancer, cancer of the uterine cervix, ovarian cancer (e.g., ovarian epithelial cancer, extragonadal germ cell tumor, ovarian germ cell tumor, ovarian low malignant potential tumor etc.), urinary bladder cancer, urethral cancer, skin cancer (e.g., ocular melanoma, Merkel cell carcinoma etc.), hemangioma, malignant lymphoma, malignant melanoma, thyroid cancer (e.g., medullary thyroid carcinoma etc.), parathyroid cancer, nasal cancer, paranasal cancer, bone tumors (e.g., osteosarcoma, Ewing's tumor, uterus sarcoma, soft tissue sarcoma etc.), vascular fibroma, retinoblastoma, penile cancer, testis tumor, solid cancer in childhood (e.g., Wilms' tumor, childhood kidney tumor, etc.), Kaposi's sarcoma, Kaposi's sarcoma derived from AIDS, maxillary sinus tumor, fibrous histiocytoma, leiomyosarcoma, rhabdomyosarcoma, leukemia (e.g., acute myeloid leukemia, acute lymphoblastic leukemia etc.) etc.), atherosclerosis, angiogenesis (e.g., angiogenesis associated with growth of solid cancer and sarcoma, angiogenesis associated with tumor metastasis, angiogenesis associated with diabetic retinopathy, etc.), and viral diseases (HIV infection etc.) and the like.

The tyrosine kinase dependent disease further includes cardiovascular diseases related to abnormal tyrosine kinase enzyme activity. Accordingly, a combination drug of a HER2 inhibitor and a concomitant drug can also be used as an agent for the prophylaxis or treatment of cardiovascular disease such as restenosis.

A combination drug of a HER2 inhibitor and a concomitant drug is useful as an anti-cancer agent for the prophylaxis or treatment of cancer, particularly breast cancer, prostate cancer, lung cancer, pancreatic cancer, kidney cancer, colorectal cancer, small intestinal cancer, esophagus cancer and gastric cancer and the like for a patient coexpressing HER2 and HER3.

A combination drug of a HER2 inhibitor and a concomitant drug shows low toxicity and can be directly used as it is as a pharmaceutical agent or as a pharmaceutical composition containing a pharmaceutically acceptable carrier known per se etc. for a mammal (e.g., human, horse, bovine, dog, cat, rat, mouse, rabbit, swine, monkey etc.)

A combination drug of a HER2 inhibitor and a concomitant drug can be safely administered orally or parenterally (e.g., topical, rectal, intravenous administration etc.), for example, as a pharmaceutical composition obtained by mixing a HER2 inhibitor and/or the above-mentioned concomitant drug with a pharmacologically acceptable carrier according to a method known per se, such as tablet (including sugar-coated tablet, film-coated tablet), powder, granule, capsule (including soft capsule), liquid, injection, suppository, sustained-release preparation and the like. Injection can be administered intravenously, intramuscularly, subcutaneously, or by intraorgan administration or direct administration to the lesion.

As the pharmacologically acceptable carrier that may be used for the production of a combination drug of a HER2 inhibitor and a concomitant drug, various organic or inorganic carrier substances conventionally used as a preparation material can be mentioned. For example, excipient, lubricant, binder and disintegrant for solid preparations, solvent, solubilizing agents, suspending agent, isotonicity agent, buffer and soothing agent for liquid preparations and the like can be mentioned. Where necessary, conventional additives such as preservatives, antioxidants, colorants, sweetening agents, adsorbing agents, wetting agents and the like can be used as appropriate in suitable amounts.

The mixing ratio of the HER2 inhibitor and the concomitant drug in the combination drug of the present invention can be appropriately selected according to the subject of administration, administration route, disease and the like.

For example, while the content of the HER2 inhibitor in the combination drug of the HER2 inhibitor and the concomitant drug varies depending on the form of the preparation, it is generally about 0.01 to 100 wt %, preferably about 0.1 to 50 wt %, more preferably about 0.5 to about 20 wt %, relative to the whole preparation.

While the content of the concomitant drug in the combination drug of the HER2 inhibitor and the concomitant drug varies depending on the form of the preparation, it is generally about 0.01 to 100 wt %, preferably about 0.1 to 50 wt %, more preferably about 0.5 to about 20 wt %, relative to the whole preparation.

While the content of the additive such as a carrier in the combination drug of a HER2 inhibitor and a concomitant drug of the present invention varies depending on the form of the preparation, it is generally about 1 to 99.99 wt %, preferably about 10 to about 90 wt %, relative to the whole preparation.

When a HER2 inhibitor and a concomitant drug are separately made into preparations, similar contents can be employed.

These preparations can be produced by a method known per se, which is generally used for a preparation step.

While the dose of the combination drug of a HER2 inhibitor and a concomitant varies depending on the kind of HER2 inhibitor, age, body weight, symptom, dosage form, administration method, administration period and the like, for example, it is generally, as a HER2 inhibitor and a concomitant drug, each within the range of about 0.1 mg-about 500 mg, preferably about 1 mg-about 100 mg, for oral administration, and each about 0.01 mg-about 100 mg, more preferably about 0.1 mg-about 10 mg for parenteral administration, for one patient (adult, body weight about 60 kg). The dose can be administered in 1-3 portions a day. Of course, since the dose as described above varies depending on various conditions, amounts smaller than the above-mentioned dosage may sometimes be sufficient, further, amounts over that range sometimes have to be administered.

The amount of the concomitant drug can be set at any value unless side effects are problematical. The daily dosage in terms of the concomitant drug differs depending on the severity of the symptom, age, sex, body weight, sensitivity difference of the subject, administration period, interval, and nature, pharmacy, kind of the pharmaceutical preparation, kind of effective ingredient, and the like, and not particularly restricted, and the amount of a drug is, in the case of oral administration for example, usually from about 0.001 to 2000 mg, preferably from about 0.01 to 500 mg, further preferably from about 0.1 to 100 mg, per 1 kg/body weight of a mammal, and this is usually administered once to 3 times in division a day.

For administration of the combination drug of a HER2 inhibitor and a concomitant drug, a HER2 inhibitor may be administered after administration of the concomitant drug or the concomitant drug may be administered after administration of a HER2 inhibitor, though they may be administered simultaneously. When administered at a time interval, the interval varies depending on the effective ingredient, dosage form and administration method, and, for example, when the concomitant drug is administered first, a method in which a HER2 inhibitor is administered within time range of from 1 minute to 3 days, preferably from 10 minutes to 1 day, more preferably from 15 minutes to 1 hour, after administration of the concomitant drug is exemplified. When a HER2 inhibitor is administered first, a method in which the concomitant drug is administered within time range of from 1 minute to 1 day, preferably from 10 minutes to 6 hours, more preferably from 15 minutes to 1 hour after administration of a HER2 inhibitor is exemplified.

As the preferable administration method, for example, about 0.001-200 mg/kg of a concomitant drug formulated as an oral administration preparation is administered by oral administration and, about 15 min later, about 0.005-100 mg/kg of a HER2 inhibitor formulated as an oral administration preparation is orally administered, for a daily dose.

EXAMPLES

While the present invention is explained in detail in the following Examples, the present invention is not limited to them. Compound X in the Examples means N-{2-[4-({3-chloro-4-[3-(trifluoromethyl)phenoxy]phenyl}amino)-5H-pyrrolo[3,2-d]pyrimidin-5-yl]ethyl}-3-hydroxy-3-methylbutanamide.

Example 1

Prediction Marker HER2/HER3 for Sensitivity to Compound X

Sulforhodamine B staining method was used for cell growth inhibitory assay. Each cell was plated on a 96 well plate (Nunc). The next day, compound X was serially diluted and added thereto. The cell lines used and the terms of incubation of the compound are indicated separately. To immobilize the cells, 25% glutaraldehyde solution (Wako, 50 μL) was added to the culture medium (200 μL) and the mixture was left standing at room temperature for 15 min.

The plate was then washed once with PBS (Invitrogen), 200 μL of PBS was added, 25 μL of 50% trichloroacetic acid (Wako) was added, and the mixture was left standing at 4° C. for 1 hr or longer. The plate was washed 5 times with tap water, redundant water was removed by slamming the plate against paper towels. A 1% (W/W) acetic acid solution (50 μL) containing 0.4% (w/v) Sulforhodamine B (SRB, Sigma) was added to each well and, 15 min later, the plate was washed 3 times with 1% acetic acid solution. The plate was thoroughly dried, 10 mM Tris solution was added, and the mixture was stirred well in a plate shaker, and the absorbance at 550 nm was measured (Bio-Rad, Benchmark Plus).

The number of cells at each compound concentration was calculated using a control without a drug as 100%. The cell lines used (in the order of cell name, compound incubation period) were PC-3 (2000 cells, 3 days), MDA-MB-231 (2000 cells, 3 days), MES-SA (3000 cells, 3 days), MES-SA/Dx-5 (3000 cells, 3 days), OV-90 (3000 cells, 5 days), SK-BR-3 (2000 cells, 5 days), Calu-3 (5000 cells, 7 days), UACC812 (10000 cells, 10 days), UACC893 (5000 cells, 15 days), T-47D (3000 cells, 3 days), Cs-Fb (3000 cells, 3 days), MRC-5 (3000 cells, 3 days), OE21 (2000 cells, 3 days), OE33 (2000 cells, 4 days), A2780 (5000 cells, 3 days), HCC4006 (3000 cells, 5 days), KYSE-30 (3000 cells, 3 days), A431 (2000 cells, 5 days), BT-474 (6000 cells, 5 days), ZR-75-1 (6000 cells, 3 days), A375 (3000 cells, 3 days), SK-OV-3 (3000 cells, 3 days), HT-29 (3000 cells, 3 days), HCT116 (1000 cells, 3 days), MDA-MB-361 (15000 cells, 10 days), MDA-MB-453 (3500 cells, 4 days), NCI-H1781 (15000 cells, 7 days), OE19 (2000 cells, 4 days), SK-BR-3 (2000 cells, 5 days), AU565 (2000 cells, 5 days), MDA-MB-175VII (5000 cells, 10 days), HCC1419 (3000 cells, 5 days), NCI-N87 (12000 cells, 5 days), MCF-7 (3000 cells, 3 days), HCC1954 (3000 cells, 3 days) and K562 (10000 cells, 5 days). The K562 cells, which are non-adherent cells, were measured using Cell counting kit-8 (Dojin).

Total RNA was extracted from each cell culture using an RNeasy mini kit (Qiagen). Total RNA (2 μg) was subjected to a Reverse Transcriptase reaction using a high capacity cDNA archive kit (Applied Biosystems) to give cDNA. The obtained cDNA was diluted 200-fold with Nuclease Free water, and 5 μL thereof was used for PCR reaction. The diluted cDNA solution, 2× TaqMan Universal PCR Master Mix (Applied Biosystems), 20× Human GAPDH (Primers and Probe, Pre-Developed TaqMan Assay Reagent) and Nuclease Free water (Promega) were mixed. In another PCR tube, a sample was adjusted using mRNA expression of EGFR, HER2, HER3, HER4, PTEN or IGF-1R (TaqMan Gene Expression Assays, Applied Biosystems). PCR reaction and analysis were performed using GeneAmp 7700 (Applied Biosystems). The PCR reaction was performed 40 cycles under the conditions of 50° C.×2 min and 95° C.×10 min, then 95° C.×15 sec and 60° C.×1 min. For data analysis, ΔΔCt method was used for calculation with GAPDH as an internal control.

As a result, a negative correlation was observed between the expression level of HER2 or HER3 and the cell growth inhibitory $IC_{50}$ value (FIG. 1). Table 1 shows a list of the correlation coefficient of cell growth inhibitory $IC_{50}$ values of compound X in the cultured cell lines and EGFR, HER2, HER3, HER4, PTEN or IGF-1R gene expression level in each cell.

That is, it was found that a high expression level of HER2 or HER3 was associated with a growth inhibitory action of compound X.

TABLE 1

|  | r | p |
|---|---|---|
| HER3 | −0.73 | <0.001 |
| HER2 | −0.66 | <0.001 |
| HER4 | −0.40 | 0.036 |
| PTEN | −0.33 | 0.051 |
| IGF-1R | −0.16 | 0.348 |
| EGFR | 0.006 | 0.974 |

Example 2

Involvement of HER3 in Cell Growth

BT-474, SK-BR-3 or MCF-7 cells were plated in 96 well plate (Nunc) at 6000, 2000 or 3000 cells/well, respectively. The next day, non-silencing control RNA (Qiagen) or HER3 siRNA (SantaCruz) was transfected at a final concentration of 5 nM. For the transfection, Lipofectamine 2000 (Invitrogen) was used according to the protocol. Five days after the transfection, the cells were fixed, and a cell growth inhibitory assay was performed using SRB staining method.

Figure 2:
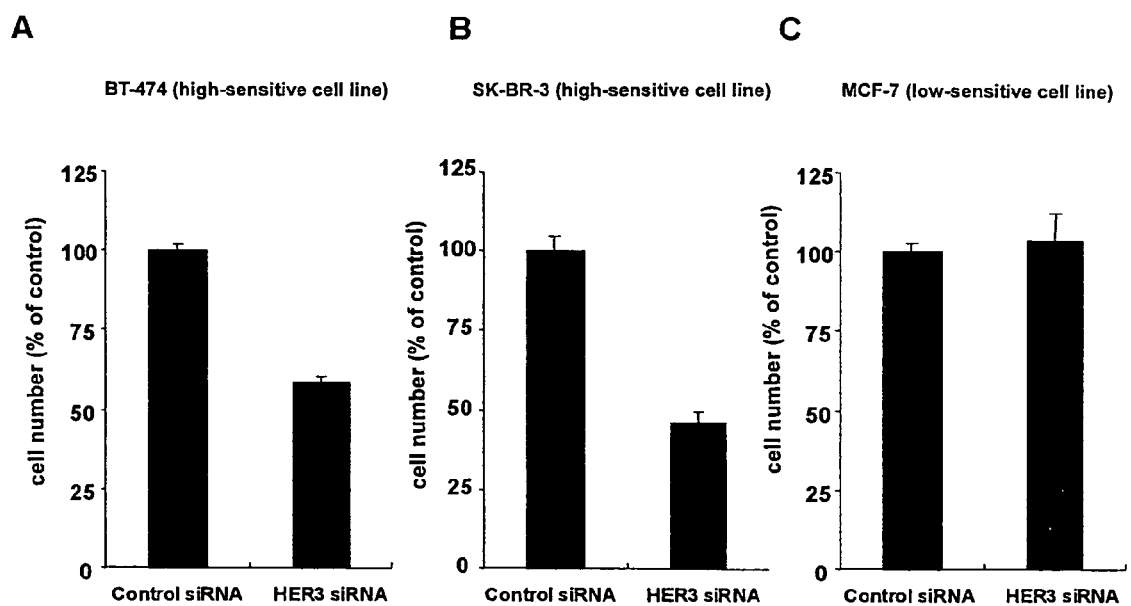
FIG. 2 shows an influence on the cell growth of the HER3 knockdown by the RNAi method, wherein the vertical axis shows the number of cells (% of control), and (A), (B) and (C) show the results in BT-474, SK-BR-3 and MCF-7 cells, respectively.

Cell growth was suppressed when HER3 expression was knocked down using RNAi method in compound X high-sensitive cells (FIGS. 2A and B). However, when HER3 expression was knocked down in the same manner in compound X low-sensitive cells, the cell growth was not suppressed (FIG. 2C). Therefore, it has been suggested that HER3 is important for promoting cell growth or maintaining cell life of compound X high-sensitive cells.

Formulation Example 1

Dose Per Tablet

| (1) compound X | 10.0 mg |
|---|---|
| (2) lactose | 60.0 mg |
| (3) cornstarch | 35.0 mg |
| (4) gelatin | 3.0 mg |
| (5) magnesium stearate | 2.0 mg |

A mixture of compound X (10.0 mg), lactose (60.0 mg) and cornstarch (35.0 mg) is granulated using 10 wt % aqueous gelatin solution (0.03 ml, 3.0 mg as gelatin) and passing through a sieve (1 mm mesh). The granules are dried at 40° C. and filtered again. The obtained granules are mixed with magnesium stearate (2.0 mg) and compressed. The obtained core tablet is coated with a sugar coating of a suspension of sucrose, titanium dioxide, talc and gum arabic, and glazed with beeswax to give a sugar-coated tablet.

Formulation Example 2

Dose Per Tablet

| (1) compound X | 10.0 mg |
|---|---|
| (2) lactose | 70.0 mg |
| (3) cornstarch | 50.0 mg |
| (4) solubilized starch | 7.0 mg |
| (5) magnesium stearate | 3.0 mg |

Compound X (10.0 mg) and magnesium stearate (3.0 mg) are granulated with an aqueous solution of solubilized starch (0.07 ml, 7.0 mg as solubilized starch), dried, and mixed with lactose (70.0 mg) and cornstarch (50.0 mg). The mixture is compressed to give a tablet.

What is claimed is:

1. A method for treating cancer, which comprises selecting a patient having cancer and coexpressing HER2 and HER3, and administering an effective amount of N-{2-[4-({3-chloro-4-[3-(trifluoromethyl)phenoxy]phenyl}amino)-5H-pyrrolo[3,2-d]pyrimidin-5-yl]ethyl}-3-hydroxy-3-methylbutanamide or a salt thereof to the patient.

2. The method of claim 1, wherein the cancer is breast cancer, prostate cancer, lung cancer, pancreatic cancer, kidney cancer, colorectal cancer, small intestinal cancer, esophagus cancer or gastric cancer.

* * * * *